(12) United States Patent
Holmes et al.

(10) Patent No.: US 7,084,245 B2
(45) Date of Patent: Aug. 1, 2006

(54) PEPTIDES THAT BIND TO THE ERYTHROPOIETIN RECEPTOR

(75) Inventors: Christopher P. Holmes, Saratoga, CA (US); Qun Yin, Palo Alto, CA (US); Guy Lalonde, Woodside, CA (US); Peter J. Schatz, Cupertino, CA (US); David Tumelty, Sunnyvale, CA (US); Balu Palani, Cupertino, CA (US); Genet Zemede, Santa Clara, CA (US)

(73) Assignee: Affymax, Inc., Palo Alto, CA (US)

( * ) Notice: Subject to any disclaimer, the term of this patent is extended or adjusted under 35 U.S.C. 154(b) by 0 days.

(21) Appl. No.: 10/844,968

(22) Filed: May 12, 2004

(65) Prior Publication Data

US 2005/0137329 A1    Jun. 23, 2005

Related U.S. Application Data

(60) Provisional application No. 60/469,993, filed on May 12, 2003, provisional application No. 60/470,244, filed on May 12, 2003.

(51) Int. Cl.
A01N 43/40 (2006.01)
A61K 38/00 (2006.01)

(52) U.S. Cl. .............................. 530/323; 514/9; 930/90

(58) Field of Classification Search ..................... None
See application file for complete search history.

(56) References Cited

U.S. PATENT DOCUMENTS

| | | | |
|---|---|---|---|
| 4,179,337 A | 12/1979 | Davis et al. | |
| 4,677,195 A | 6/1987 | Hewick et al. | |
| 5,278,065 A | 1/1994 | D'Andrea et al. | |
| 5,292,654 A | 3/1994 | Yoshimura et al. | |
| 5,378,808 A | 1/1995 | D'Andrea et al. | |
| 5,441,868 A | 8/1995 | Lin | |
| 5,547,933 A | 8/1996 | Lin | |
| 5,580,853 A | 12/1996 | Sytkowski | |
| 5,614,184 A | 3/1997 | Sytkowski et al. | |
| 5,618,698 A | 4/1997 | Lin | |
| 5,621,080 A | 4/1997 | Lin | |
| 5,654,276 A | 8/1997 | Barrett et al. | |
| 5,668,110 A | 9/1997 | Barrett et al. | |
| 5,677,280 A | 10/1997 | Barrett et al. | |
| 5,683,983 A | 11/1997 | Barrett et al. | |
| 5,747,446 A | 5/1998 | Sytkowski | |
| 5,756,349 A | 5/1998 | Lin | |
| 5,767,078 A | 6/1998 | Johnson et al. | |
| 5,773,569 A | 6/1998 | Wrighton et al. | |
| 5,830,851 A | 11/1998 | Wrighton et al. | |
| 5,869,451 A | 2/1999 | Dower et al. | |
| 5,919,758 A | 7/1999 | Sytkowski | |
| 5,932,546 A | 8/1999 | Barrett et al. | |
| 5,955,422 A | 9/1999 | Lin | |
| 5,986,047 A | 11/1999 | Wrighton et al. | |
| 6,048,971 A | 4/2000 | Sytkowski et al. | |
| 6,077,939 A | 6/2000 | Wei et al. | |
| 6,083,913 A | 7/2000 | Dower et al. | |
| 6,103,879 A | 8/2000 | Chaovapong et al. | |
| 6,107,272 A | 8/2000 | Sytkowski | |
| 6,113,906 A | 9/2000 | Greenwald et al. | |
| 6,121,238 A | 9/2000 | Dower et al. | |
| 6,153,407 A | 11/2000 | Sytkowski et al. | |
| 6,221,608 B1 | 4/2001 | Middleton et al. | |
| 6,251,864 B1 | 6/2001 | Dower et al. | |
| 6,333,031 B1 | 12/2001 | Olsson et al. | |
| 6,340,742 B1 | 1/2002 | Burg et al. | |
| 6,465,430 B1 | 10/2002 | Dower et al. | |
| 6,489,293 B1 | 12/2002 | Sytkowski et al. | |
| 6,506,362 B1 | 1/2003 | Dower et al. | |
| 6,531,121 B1 | 3/2003 | Brines et al. | |
| 6,552,008 B1 | 4/2003 | Duffy et al. | |
| 6,583,272 B1 | 6/2003 | Bailon | |
| 6,660,843 B1 | 12/2003 | Feige et al. | |
| 2002/0015691 A1 | 2/2002 | Greenwald et al. | |
| 2002/0037841 A1 | 3/2002 | Papadimitriou et al. | |
| 2002/0052317 A1 | 5/2002 | Itri et al. | |
| 2002/0086816 A1 | 7/2002 | Brines et al. | |
| 2002/0115833 A1 | 8/2002 | Burg et al. | |
| 2002/0160013 A1 | 10/2002 | Olsson et al. | |
| 2002/0169128 A1 | 11/2002 | Sigounas et al. | |
| 2002/0177166 A1 | 11/2002 | Guthridge et al. | |
| 2003/0009018 A1 | 1/2003 | Maeda et al. | |
| 2003/0050269 A1 | 3/2003 | Escary | |
| 2003/0083251 A1 | 5/2003 | Westenfelder | |
| 2003/0083361 A1 | 5/2003 | Luengo et al. | |
| 2003/0104988 A1 | 6/2003 | Brines et al. | |

(Continued)

FOREIGN PATENT DOCUMENTS

WO    WO-WO 90/12874    11/1990

(Continued)

OTHER PUBLICATIONS

Johnson, et al., 1998, Biochemistry, 37, 3699-3710.*

(Continued)

*Primary Examiner*—Bruce R. Campell
*Assistant Examiner*—Satyanarayana R. Gudibande
(74) *Attorney, Agent, or Firm*—Darby & Darby

(57) ABSTRACT

The present invention relates to peptide compounds that are agonists of the erythropoietin receptor (EPO-R). The invention also relates to therapeutic methods using such peptide compounds to treat disorders associated with insufficient or defective red blood cell production. Pharmaceutical compositions, which comprise the peptide compounds of the invention, are also provided.

72 Claims, No Drawings

U.S. PATENT DOCUMENTS

| | | |
|---|---|---|
| 2003/0120045 A1 | 6/2003 | Bailon |
| 2003/0125262 A1 | 7/2003 | Kiessling et al. |
| 2003/0134798 A1 | 7/2003 | Brines et al. |
| 2003/0191291 A1 | 10/2003 | Kochendoerfer et al. |

FOREIGN PATENT DOCUMENTS

| | | |
|---|---|---|
| WO | WO-WO 92/16555 | 10/1992 |
| WO | WO-WO 96/40189 | 12/1996 |
| WO | WO-WO 96/40749 | 12/1996 |
| WO | WO-WO 96/40750 | 12/1996 |
| WO | WO-WO 96/40772 | 12/1996 |
| WO | WO-WO 98/25965 | 12/1997 |
| WO | WO-WO 00/24770 | 5/2000 |
| WO | WO-WO 00/24782 | 5/2000 |
| WO | WO-WO 00/33881 | 6/2000 |
| WO | WO-WO 01/38342 A2 | 5/2001 |
| WO | WO-WO 01/91780 A1 | 12/2001 |
| WO | WO-WO 02/065988 | 8/2002 |
| WO | WO-WO 2004/014424 | 2/2004 |
| WO | WO-WO-2004/100997 | 11/2004 |
| WO | WO-WO-2004/101600 | 11/2004 |
| WO | WO-WO-2004/101606 | 11/2004 |
| WO | WO-WO 2004/101611 A2 | 11/2004 |
| WO | WO-WO 2004/108070 | 12/2004 |

OTHER PUBLICATIONS

Wrighton, et al., Nature Biotechnology, 1997, 15, 1261-1265.*

Johnson, et al., Chemistry & Biology, 1997, 4, 939-950.*

Abuchowski, A., et al., "Effect of covalent attachment of polyethylene glycol on immunogenicity and circulating life of bovine liver catalase," J. Biol. Chem, vol. 252, pp. 3582-3586 (1977).

Beauchamp, C.O., et al., "A new procedure for the synthesis of polytheylene glycol-protein adducts; effects on function, receptor recognition, and clearance of superoxide dismutase, lactoferrin, and alpha 2-macroglobulin", Anal Biochem., vol. 131, pp. 25-33 (1983).

Chen, R.H., et al., "Properties of two urate oxidases modified by the covalent attachment of poly(ethylene glycol)", Biochem. Biophys. Acta., vol. 660, pp. 293-298 (1981).

Francis, G.E., et al., "PEGylation of cytokines and other therapeutic proteins and peptides: The importance of biological optimisation of coupling techniques", Int. J. Hematol, vol. 68, pp. 1-18 (1998).

Kita, Y., et al., "Characterization of a polyethylene glycol conjugate of recombinant human interferon-gamma", Dr. Des. Deliv. vol. 6, pp. 157-167 (1990).

Knauf, M.J., et al., "Relationship of effective molecular size to systemic clearance in rats of recombinant interleukin-2 chemically modified with water-soluble polymers", J. Biol. Chem., vol. 263, pp. 15064-15070 (1988).

Saifer, M.G., et al., "Plasma clearance and immunologic properties of long-acting superoxide dismutase prepared using 35,000 to 120,000 dalton poly-ethylene glycol", Adv. Exp. Med. Biol. vol. 366, pp. 377-387 (1994).

Somack, R., et al., "Preparation of long-acting superoxide dismutase using high molecular weight polyethylene glycol (41,000-72,000 daltons)", Free. Radic. Res. Commun. vols. 12-13, pp. 553-562 (1991); and.

Tsutsumi, Y. et al., "Polyethylene glycol modification of interleukin-6 enhances its thrombopoletic activity", J. Controlled Release, vol. 33, pp. 447 (1995).

Johnson et al., "Identification of a 13 amino acid peptide mimetic of erythropoietin and description of amino acids critical for the mimetic activity of EMP1", Biochemistry 37: 3699-3710 (1998).

Sasaki, et al., "Carbohydrate structure of erythropoietin expressed in Chinese hamster ovary cells by a human erythropoietin cDNA", Journal of Biological Chemistry 262:12059-12076 (1987).

Veronese, F. M., "Peptide and protein PEGylation: a review of problems and solutions", Biomaterials 22:405-417 (2001).

Wrighton et al., "Small peptides as potent mimetics of the protein hormone erythropoietin", Science 273:458-463 (1996).

Wrighton, N.C. et al., "Increased potency of an erythropoietin peptide mimetic through covalent dimerization", Nature Biotechnology15:1261-1265 (1997).

Woller, N.C. et al., "The lectin-binding propertiesof six generations of mannose-functionaled dendrimers", Organic Letters 4:7-10 (2002).

Johnson, D.L., et al., "Amino-terminal dimerization of an erythropoietin mimetic peptide results in increased erythripoietic activity", Chem. Biol., vol. 4, pp. 939-950 (1997).

Lee, J.W., et al., "Reduction of azides to primary amines in substrates bearing labile ester functionality. Synthesis of a PEG-solubilized, "Y"-shaped iminodiacetic acid reagent for preparation of folate-tethered drugs", Org. Lett., vol. 1, pp. 179-181 (1999).

Greenwald, R.B., et al. (2003) Effective drug delivery of PEGylated drug conjugates. *Adv. Drug Deliv. Rev.* 55:217-250.

Greenwald, R.B., et al. (2003) Controlled release of proteins from their poly(ethylene glycol) conjugates: drug delivery systems employing 1,6-elimination. *Bioconjug. Chem.* 14:395-403.

* cited by examiner

PEPTIDES THAT BIND TO THE ERYTHROPOIETIN RECEPTOR

CROSS-REFERENCE TO RELATED APPLICATIONS

Priority is claimed to U.S. provisional application Ser. Nos. 60/469,993 and 60/470,244 both filed on May 12, 2003. The contents of these priority applications are incorporated into the present disclosure by reference and in their entireties.

FIELD OF THE INVENTION

The present invention relates to peptide compounds that are agonists of the erythropoietin receptor (EPO-R). The invention also relates to therapeutic methods using such peptide compounds to treat disorders associated with insufficient or defective red blood cell production. Pharmaceutical compositions, which comprise the peptide compounds of the invention, are also provided.

BACKGROUND OF THE INVENTION

Erythropoietin (EPO) is a glycoprotein hormone of 165 amino acids, with a molecular weight of about 34 kilodaltons (kD) and preferred glycosylation sites on amino-acid positions 24, 38, 83, and 126. It is initially produced as a precursor protein with a signal peptide of 23 amino acids. EPO can occur in three forms: $\alpha$, $\beta$, and asialo. The $\alpha$ and $\beta$ forms differ slightly in their carbohydrate components, but have the same potency, biological activity, and molecular weight. The asialo form is an $\alpha$ or $\beta$ form with the terminal carbohydrate (sialic acid) removed. The DNA sequences encoding EPO have been reported [U.S. Pat. No. 4,703,008 to Lin].

EPO stimulates mitotic division and differentiation of erythrocyte precursor cells, and thus ensures the production of erythrocytes. It is produced in the kidney when hypoxic conditions prevail. During EPO-induced differentiation of erythrocyte precursor cells, globin synthesis is induced; heme complex synthesis is stimulated; and the number of ferritin receptors increases. These changes allow the cell to take on more iron and synthesize functional hemoglobin, which in mature erythrocytes binds oxygen. Thus, erythrocytes and their hemoglobin play a key role in supplying the body with oxygen. These changes are initiated by the interaction of EPO with an appropriate receptor on the cell surface of the erythrocyte precursor cells [See, e.g., Graber and Krantz (1978) Ann. Rev. Med. 29.51–66].

EPO is present in very low concentrations in plasma when the body is in a healthy state wherein tissues receive sufficient oxygenation from the existing number of erythrocytes. This normal low concentration is sufficient to stimulate replacement of red blood cells which are lost normally through aging.

The amount of EPO in the circulation is increased under conditions of hypoxia when oxygen transport by blood cells in the circulation is reduced. Hypoxia may be caused, for example, by substantial blood loss through hemorrhage, destruction of red blood cells by over-exposure to radiation, reduction in oxygen intake due to high altitude or prolonged unconsciousness, or various forms of anemia. In response to such hypoxic stress, elevated EPO levels increase red blood cell production by stimulating the proliferation of erythroid progenitor cells. When the number of red blood cells in circulation is greater than needed for normal tissue oxygen requirements, EPO levels in circulation are decreased.

Because EPO is essential in the process of red blood cell formation, this hormone has potentially useful applications in both the diagnosis and the treatment of blood disorders characterized by low or defective red blood cell production. Recent studies have provided a basis for the projection of EPO therapy efficacy for a variety of disease states, disorders, and states of hematologic irregularity, including: beta-thalassemia [see, Vedovato, et al. (1984) Acta. Haematol. 71:211–213]; cystic fibrosis [see, Vichinsky, et al. (1984) J. Pediatric 105:15–21]; pregnancy and menstrual disorders [see, Cotes, et al. (193) Brit. J. Ostet. Gyneacol. 90:304–311]; early anemia of prematurity [see, Haga, et al. (1983) Acta Pediatr. Scand. 72; 827–831]; spinal cord injury [see, Claus-Walker, et al. (1984) Arch. Phys. Med. Rehabil. 65:370–374]; space flight [see, Dunn, et al. (1984) Eur. J. Appl. Physiol. 52:178–182]; acute blood loss [see, Miller, et al. (1982) Brit. J. Haematol. 52:545–590]; aging [see, Udupa, et al. (1984) J. Lab. Clin. Med. 103:574–580 and 581–588 and Lipschitz, et al. (1983) Blood 63:502–509]; various neoplastic disease states accompanied by abnormal erythropoiesis [see, Dainiak, et al. (1983) Cancer 5:1101–1106 and Schwartz, et al. (1983) Otolaryngol. 109: 269–272]; and renal insufficiency [see, Eschbach. et al. (1987) N. Eng. J. Med. 316:73–78].

Purified, homogeneous EPO has been characterized [U.S. Pat. No. 4,677,195 to Hewick]. A DNA sequence encoding EPO was purified, cloned, and expressed to produce recombinant polypeptides with the same biochemical and immunological properties and natural EPO. A recombinant EPO molecule with oligosaccharides identical to those on natural EPO has also been produced [See, Sasaki, et al. (1987) J. Biol. Chem. 262:12059–12076].

The biological effect of EPO appears to be mediated, in part, through interaction with a cell membrane bound receptor. Initial studies, using immature erythroid cells isolated from mouse spleen, suggested that the EPO-binding cell surface proteins comprise two polypeptides having approximate molecular weights of 85,000 Daltons and 100,000 Daltons, respectively [Sawyer, et al. (1987) Proc. Natl. Acad. Sci. USA 84:3690–3694]. The number of EPO-binding sites was calculated to average from 800 to 1000 per cell surface. Of these binding sites, approximately 300 bound EPO with a $K_d$ of approximately 90 pM (picomolar), while the remaining bound EPO with a reduced affinity of approximately 570 pM [Sawyer, et al. (1987) J. Biol. Chem. 262:5554–5562]. An independent study suggested that EPO-responsive splenic erythroblasts, prepared from mice injected with the anemic strain (FVA) of the Friend leukemia virus, possess at total of approximately 400 high and a low affinity EPO binding sites with $K_d$ values of approximately 100 pM and 800 pM, respectively [Landschulz, et al. (1989) Blood 73:1476–1486].

Subsequent work indicated that the two forms of EPO receptor (EPO-R) were encoded by a single gene. This gene has been cloned [See, e.g., Jones, et al. (1990) Blood 76, 31–35; Noguchi, et al. (1991) Blood 78:2548–2556; Maouche, et al. (1991) Blood 78:2557–2563]. For example, the DNA sequences and encoded peptide sequences for murine and human EPO-R proteins are described in PCT Pub. No. WO 90/08822 to D'Andrea, et al. Current models suggest that binding of EPO to EPO-R results in the dimerization and activation of two EPO-R molecules, which results in subsequent steps of signal transduction [See, e.g., Watowich, et al. (1992) Proc. Natl. Acad. Sci. USA 89:2140–2144].

The availability of cloned genes for EPO-R facilitates the search for agonists and antagonists of this important receptor. The availability of the recombinant receptor protein allows the study of receptor-ligand interaction in a variety of random and semi-random peptide diversity generation systems. These systems include the "peptides on plasmids" system [described in U.S. Pat. No. 6,270;170]; the "peptides on phage" system [described in U.S. Pat. No. 5,432,018 and Cwirla, et al. (1990) Proc. Natl. Acad. Sci. USA 87:6378–6382]; the "encoded synthetic library" (ESL) system [described in U.S. patent application Ser. No. 946,239, filed Sep. 16, 1992]; and the "very large scale immobilized polymer synthesis" system [described in U.S. Pat. No. 5,143,854; PCT Pub. No. 90/15070; Fodor, et al. (1991) Science 251:767–773; Dower and Fodor (1991) Ann. Rep. Med. Chem. 26:271–180; and U.S. Pat. No. 5,424,186].

Peptides that interact to a least some exent with EPO-R have been identified and are described, for example in U.S. Pat. Nos. 5,773,569; 5,830,851; and 5,986,047 to Wrighton, et al.; PCT Pub. No. WO 96/40749 to Wrighton, et al.; U.S. Pat. No. 5,767,078 and PCT Pub. No. 96/40772 to Johnson and Zivin; PCT Pub. No. WO 01/38342 to Balu; and WO 01/91780 to Smith-Swintosky, et al. In particular, a group of peptides containing a peptide motif has been identified, members of which bind to EPO-R and stimulate EPO-dependent cell proliferation. Yet, peptides peptides identified to date that contain the motif stimulate EPO-dependent cell proliferation in vitro with EC50 values of about 20 nanomolar (nM) to about 250 nM. Thus, peptide concentrations of 20 nM to 250 nM are required to stimulate 50% of the maximal cell proliferation stimulated by EPO.

Given the immense potential of EPO-R agonists, both for studies of the important biological activities mediated by this receptor and for treatment of disease, there remains a need for the identification of peptide EPO-R agonists of enhanced potency and activity. The present invention provides such compounds.

The citation and/or discussion of cited references in this section and throughout the specification is provided merely to clarify the description of the present invention and is not an admission that any such reference is "prior art" to the present invention.

SUMMARY OF THE INVENTION

The present invention provides novel peptide compounds, which are EPO-R agonists of dramatically enhanced potency and activity. These peptide compounds are homodimers of peptide monomers having the amino acid sequence (AcG)GLYACHMGPIT(1-nal)VCQPLRK (SEQ ID NO: 1), or homodimers of peptide monomers having the amino acid sequence (AcG)GLYACHMGPIT(1-nal)VCQPLR(MeG)K (SEQ ID NO: 2), homodimers of peptide monomers having the amino acid sequence (AcG)GLYACHMGPIT(1-nal)VCQPLR(MeG) (SEQ ID NO: 3); where each amino acid is indicated by standard one letter abbreviation, "(AcG)" is N-acetylglycine, "(1-nal)" is 1-naphthylalanine, and "(MeG)" is N-methylglycine, also known as sarcosine. Each peptide monomer of a peptide dimer contains an intramolecular disulfide bond between the cysteine residues of the monomer.

The peptide monomers may be dimerized by covalent attachment to a branched tertiary amide linker. The tertiary amide linker can be depicted as:

—C$^1$O—CH$_2$—X—CH$_2$—C$^2$O— where: X is NCO—(CH$_2$)$_2$—N$^1$H—; C$^1$ of the linker forms an amide bond with the ε-amino group of the C-terminal lysine residue of the first peptide monomer; C$^2$ of the linker forms an amide bond with the ε-amino group of the C-terminal lysine residue of the second peptide monomer; and N$^1$ of X is attached via a carbamate linkage or an amide linkage to an activated polyethylene glycol (PEG) moiety, where the PEG has a molecular weight of about 20,000 to about 40,000 Daltons (the term "about" indicating that in preparations of PEG, some molecules will weigh more, some less, than the stated molecular weight).

Where each monomer of the homodimer has the amino acid sequence, (AcG)GLYACHMGPIT(1-nal)VCQPLRK (SEQ ID NO: 1) and N$^1$ of the linker is attached via a carbamate linkage to an activated polyethylene glycol (PEG) moiety, the novel peptide compounds of the invention may be represented as follows:

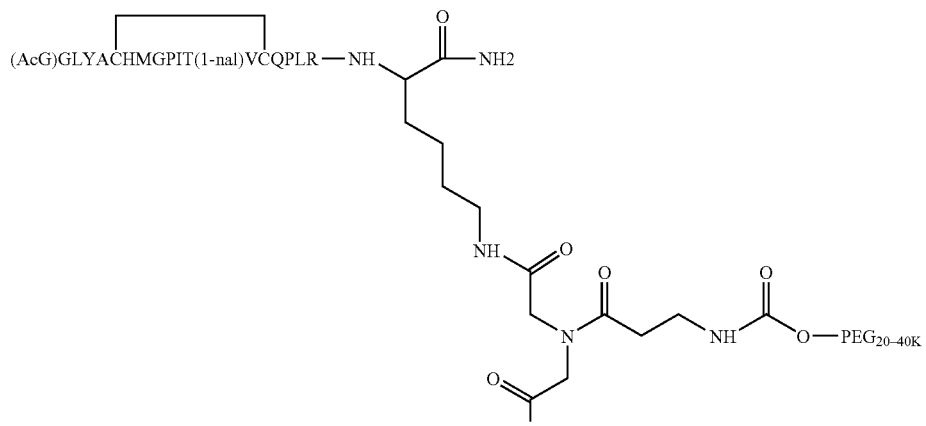

-continued

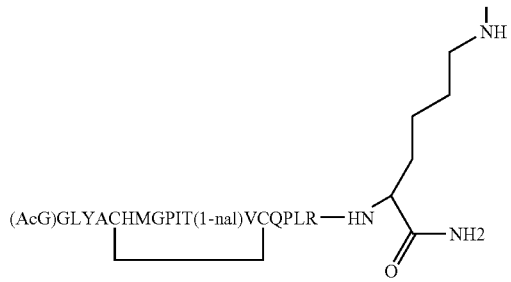

Where each monomer of the homodimer has the amino acid sequence, (AcG)GLYACHMGPIT(1-nal)VCQPLRK (SEQ ID NO: 1) and $N^1$ of the linker is attached via an amide linkage to an activated polyethylene glycol (PEG) moiety, the novel peptide compounds of the invention may be represented as follows:

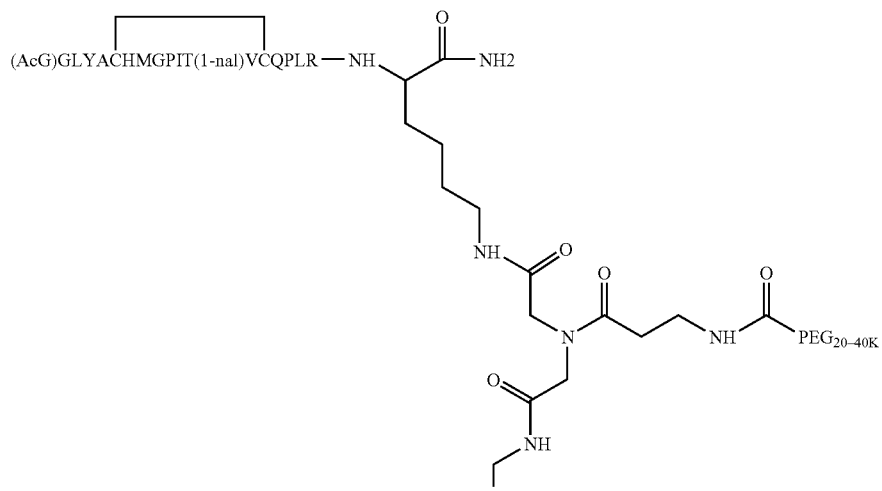

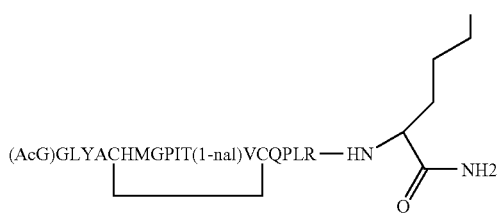

Where each monomer of the homodimer has the amino acid sequence, (AcG)GLYACHMGPIT(1-nal)VCQPLR(MeG)K (SEQ ID NO: 2) and $N^1$ of the linker is attached via a carbamate linkage to an activated polyethylene glycol (PEG) moiety, the novel peptide compounds of the invention may be represented as follows:

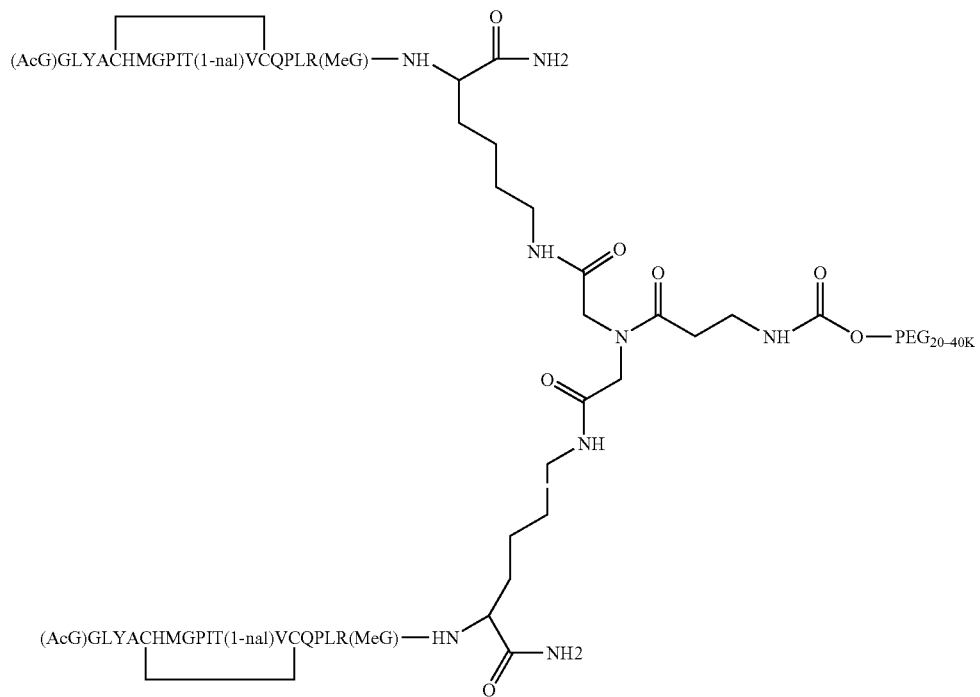

30

Where each monomer of the homodimer has the amino acid sequence, (AcG)GLYACHMGPIT(1-nal)VCQPLR(MeG)K (SEQ ID NO: 2) and $N^1$ of the linker is attached via an amide linkage to an activated polyethylene glycol (PEG) moiety, the novel peptide compounds of the invention may be represented as follows:

The peptide monomers may also be dimerized by covalent attachment to a branched tertiary amide linker. The tertiary amide linker can be depicted as:

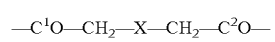

$-C^1O-CH_2-X-CH_2-C^2O-$

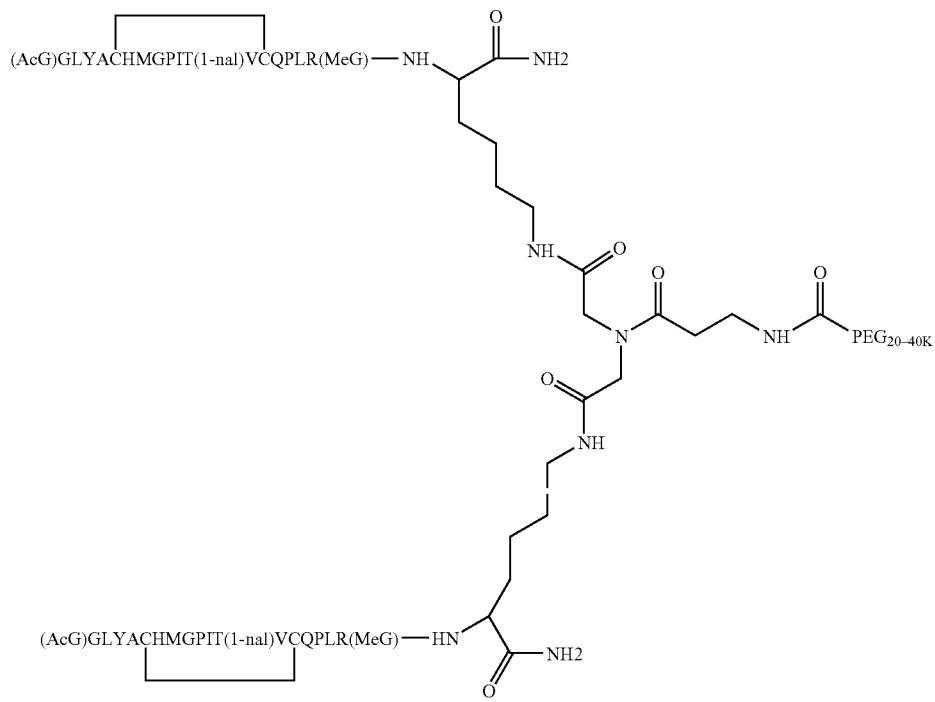

where: X is NCO—(CH$_2$)$_2$—NH—C$^3$O —; C$^1$ of the linker forms an amide bond with the ε-amino group of the C-terminal lysine residue of the first peptide monomer; and C$^2$ of the linker forms an amide bond with the ε-amino group of the C-terminal lysine residue of the second peptide monomer. The peptide dimers of the invention further comprise a spacer moiety of the following structure:

—N$^1$H—(CH$_2$)$_4$—C$^4$H—N$^2$H— where: C$^4$ of the spacer is covalently bonded to C$^3$ of X; N$^1$ of the spacer is covalently attached via a carbamate or an amide linkage to an activated polyethylene glycol (PEG) moiety; and N$^2$ of the spacer is covalently attached via a carbamate or an amide linkage to an activated PEG moiety, where PEG has a molecular weight of about 10,000 to about 50,000 Daltons (the term "about" indicating that in preparations of PEG, some molecules will weigh more, some less, than the stated molecular weight). Each PEG moiety may be, individually, 10,000 Daltons (10 kD), 20 kD, 30 kD, 40 kD, or 50 kD.

Where each monomer of the homodimer has the amino acid sequence, (AcG)GLYACHMGPIT(1-nal)VCQPLRK (SEQ ID NO: 1) and both N$^1$ and N$^2$ of the spacer are covalently attached via a carbamate linkage to an activated PEG moiety, the novel peptide compounds of the invention may be represented as follows:

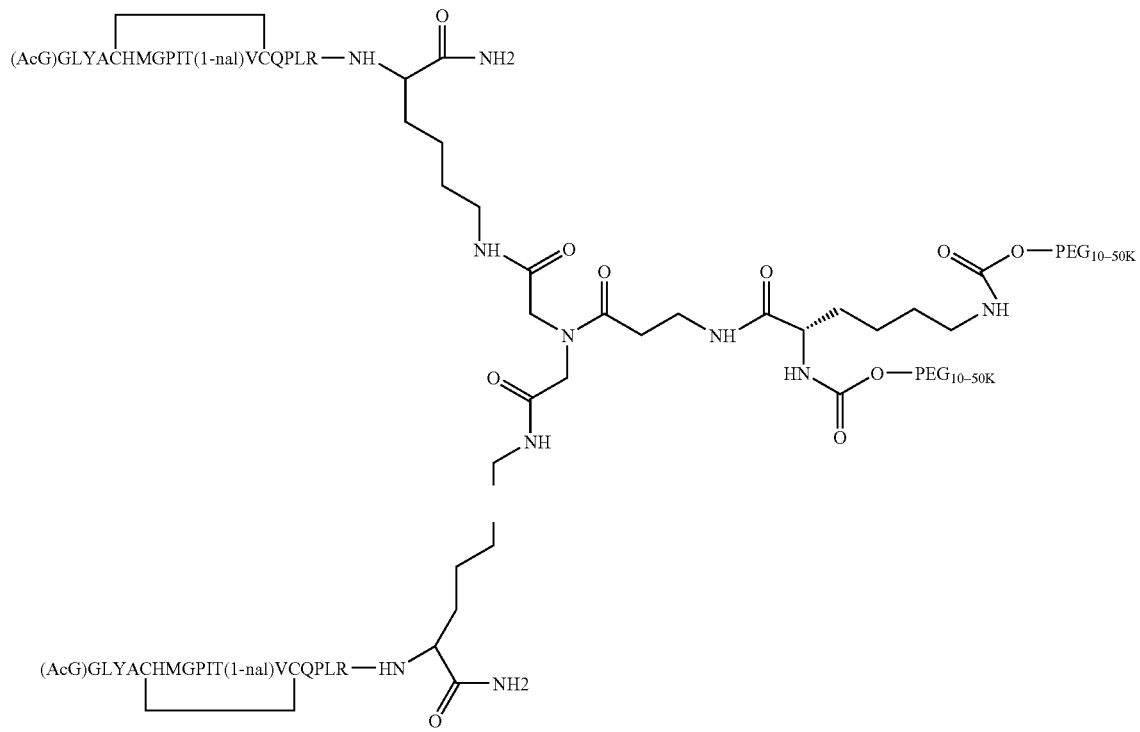

In preferred embodiments, the C-terminal lysine of the two peptide monomers is L-lysine. Also, those skilled in the art will appreciate from the above chemical structures that the lwo linear PEG moieities are joined by lysine (e.g., as mPEG$_2$-Lys-NHS or as mPEG$_2$-Lysinol-NPC), which is also preferably L-lysine and giving rise to the following stereochemistry.

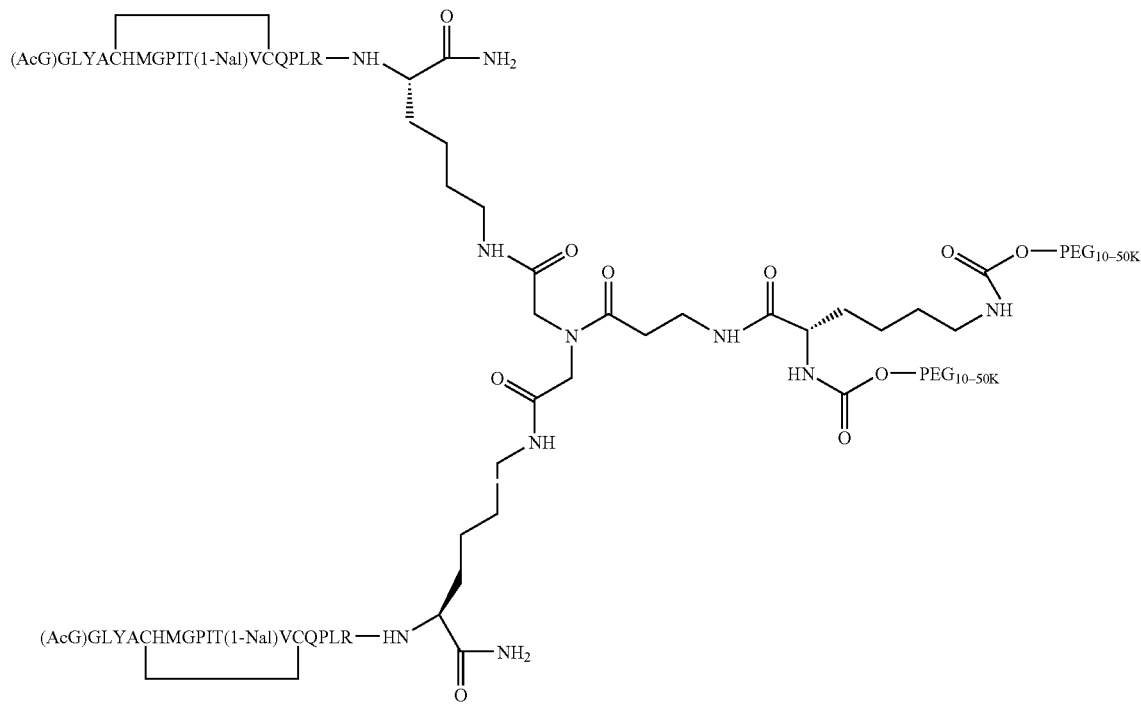

Alternatively, one or more of the lysine residues can be a D-lysine, giving rise to alternative stereochemistries which will be readily appreciate by those skilled in the art.

Where each monomer of the homodimer has the amino acid sequence, (AcG)GLYACHMGPIT(1-nal)VCQPLRK (SEQ ID NO: 1) and both $N^1$ and $N^2$ of the spacer are covalently attached via an amide linkage to an activated PEG moiety, the novel peptide compounds of the invention may be represented, as follows:

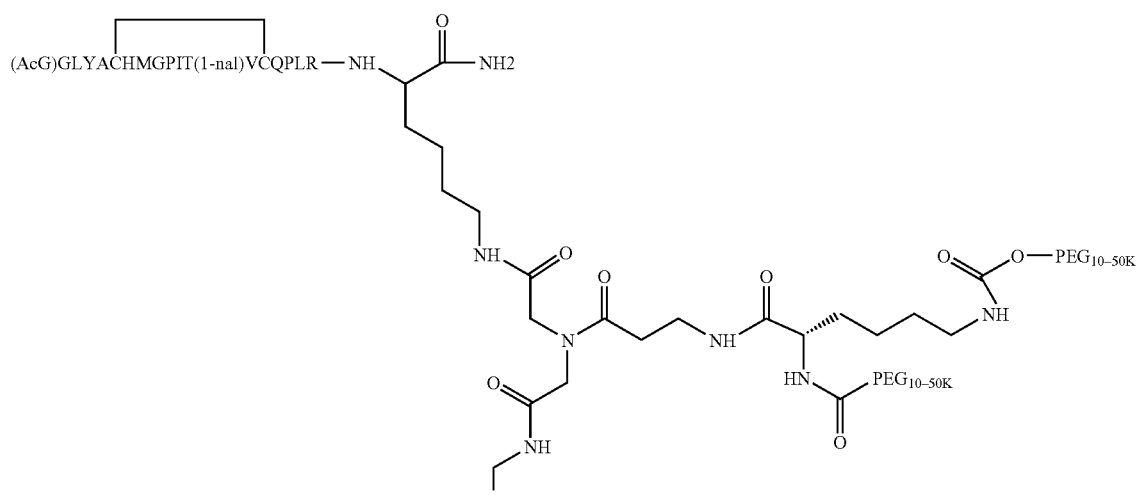

-continued

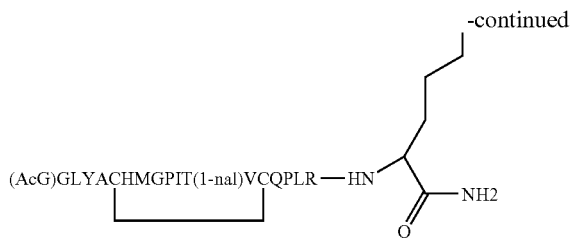

Again, the lysine molecules in this compound are preferably all L-lysine, giving rise to the following stereochemistry.

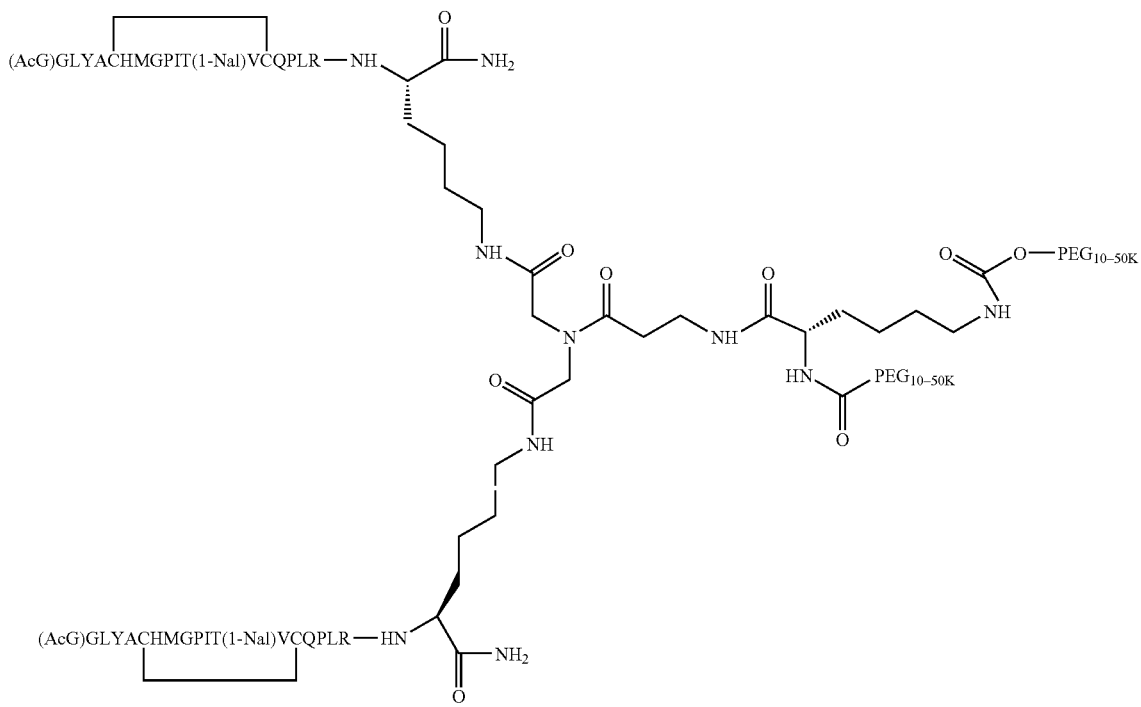

Alternatively, one or more of the lysine residues can be a D-lysine, giving rise to alternative stereochemistries which will be readily appreciated by those skilled in the art.

Where each monomer of the homodimer has the amino acid sequence, (AcG)GLYACHMGPIT(1-nal)VCQPLR (MeG)K (SEQ ID NO: 2) and both $N^1$ and $N^2$ of the spacer are covalently attached via a carbamate linkage to an activated PEG moiety, wherein Y is a carbamate group, the novel peptide compounds of the invention may be represented as follows:

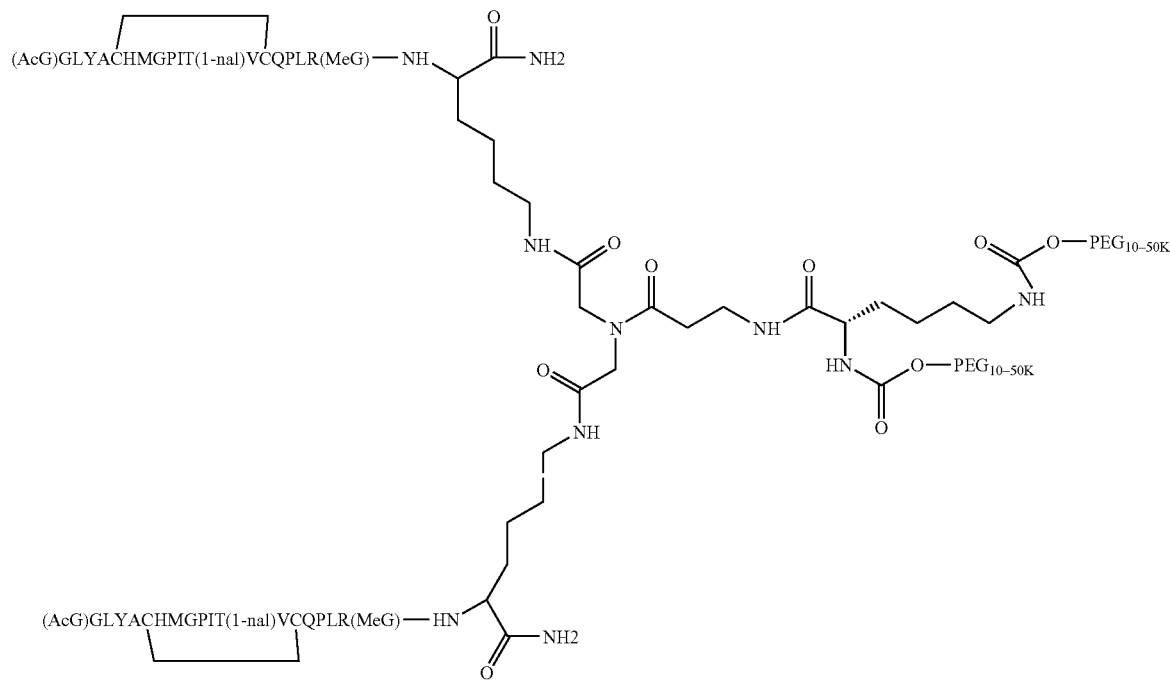
Preferably, the lysine residues joining the peptide monomer and linear PEG moieties in this molecule are all L-lysine, giving rise to the following stereochemistry:
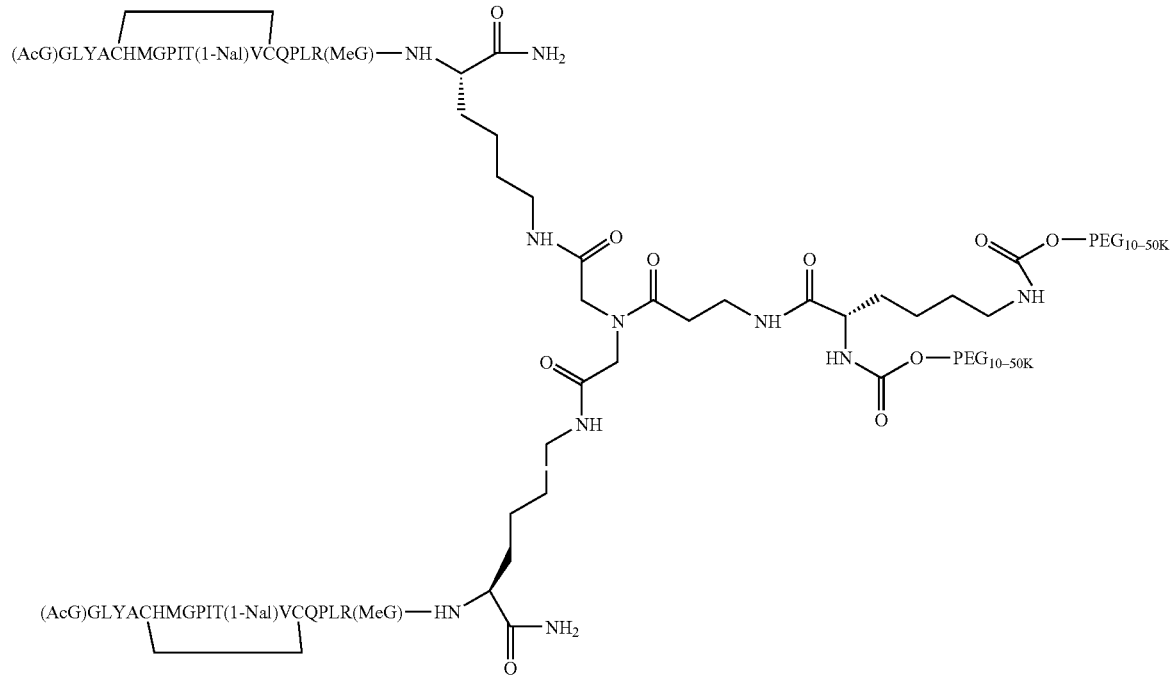
Alternatively, one or more of the lysine residues can be a D-lysine, giving rise to alternative stereochemistries that will be readily appreciated by those of ordinary skill in the art.

Where each monomer of the homodimer has the amino acid sequence, (AcG)GLYACHMGPIT(1-nal)VCQPLR(MeG)K (SEQ ID NO: 2) and both $N^1$ and $N^2$ of the spacer are covalently attached via an amide linkage to an activated PEG moiety, the novel peptide compounds of the invention may be represented as follows:

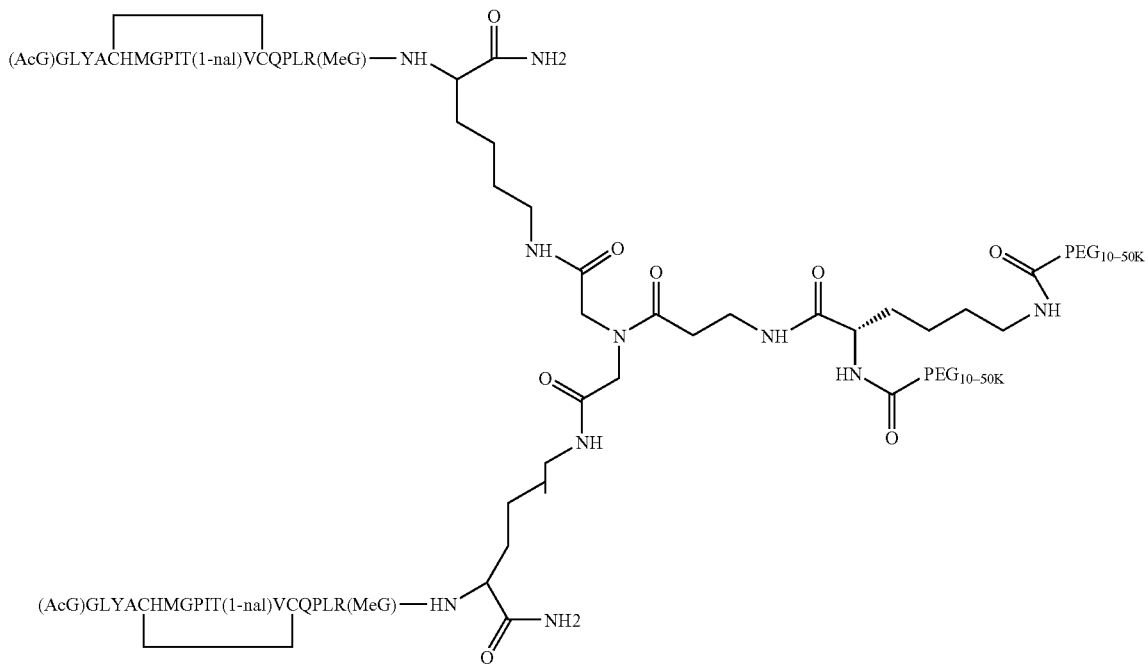

Preferably, the lysine residues joining the peptide monomer and linear PEG moieties of this molecule are all L-lysine, giving rise to the following stereochemistry.

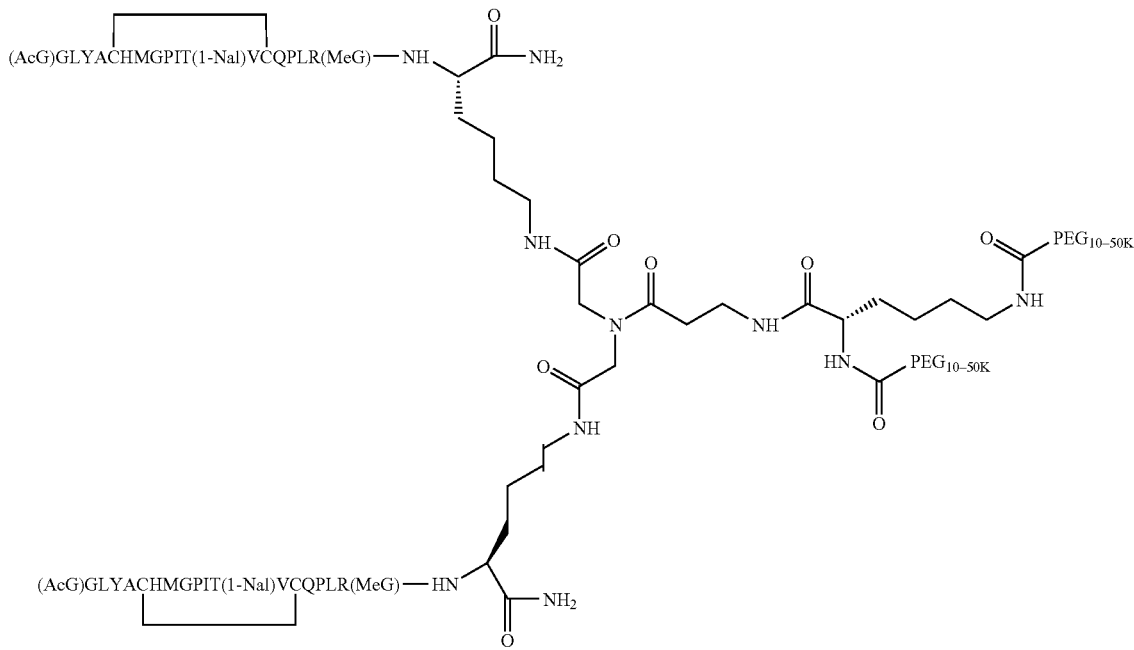

In other embodiments, one or more of the lysine residues can be a D-lysine, giving rise to alternative stereochemistries that will be readily appreciated by persons of ordinary skill in the art.

The peptide monomers may also be dimerized by attachment to a lysine linker, whereby one peptide monomer is attached at its C-terminus to the lysine's ε-amino group and the second peptide monomer is attached at its C-terminus to the lysine's α-amino group.

The peptide dimers of the invention further comprise a spacer moiety of the following structure:

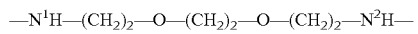

At one end, $N^1$ of the spacer is attached via an amide linkage to a carbonyl carbon of the lysine linker. At the opposite end, $N^2$ of the spacer is attached via a carbamate linkage or an amide linkage to an activated polyethylene glycol (PEG) moiety, where the PEG has a molecular weight of about 20,000 to about 40,000 Daltons (the term "about" indicating that in preparations of PEG, some molecules will weigh more, some less, than the stated molecular weight).

Where the spacer is attached via a carbamate linkage to an activated polyethylene glycol (PEG) moiety, the novel peptide compounds of the invention (SEQ ID NO: 3) may be represented as follows:

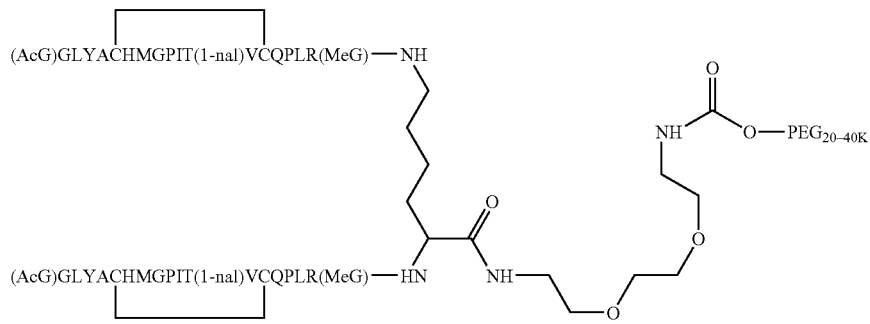

Where the spacer is attached via an amide linkage to an activated polyethylene glycol (PEG) moiety, the novel peptide compounds of the invention (SEQ ID NO: 3) may be represented as follows:

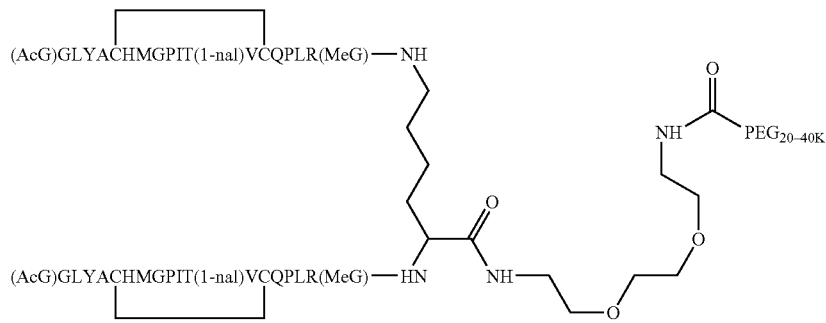

The invention further provides pharmaceutical compositions comprised of such peptide compounds, and methods to treat various medical conditions using such peptide compounds.

DETAILED DESCRIPTION OF THE INVENTION

Definitions:

Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. The unconventional amino acids in peptides are abbreviated as follows: 1-naphthylalanine is 1-nal or Np; N-methylglycine (also known as sarcosine) is MeG or Sc; and acetylated glycine (N-acetylglycine) is AcG.

As used herein, the term "polypeptide" or "protein" refers to a polymer of amino acid monomers that are alpha amino acids joined together through amide bonds. Polypeptides are therefore at least two amino acid residues in length, and are usually longer. Generally, the term "peptide" refers to a polypeptide that is only a few amino acid residues in length. The novel EPO-R agonist peptides of the present invention are preferably no more than about 50 amino acid residues in length. They are more preferably of about 17 to about 40 amino acid residues in length. A polypeptide, in contrast with a peptide, may comprise any number of amino acid residues. Hence, the term polypeptide included peptides as well as longer sequences of amino acids.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

As used herein the term "agonist" refers to a biologically active ligand which binds to its complementary biologically active receptor and activates the latter either to cause a biological response in the receptor, or to enhance preexisting biological activity of the receptor.

Novel Peptides that are EPO-R Agonists

The present invention provides novel peptide compounds, which are EPO-R agonists of dramatically enhanced potency and activity. These peptide compounds are homodimers of peptide monomers having the amino acid sequence (AcG)GLYACHMGPIT(1-nal)VCQPLRK (SEQ ID NO: 1), or homodimers of peptide monomers having the amino acid sequence (AcG)GLYACHMGPIT(1-nal)VCQPLR(MeG)K (SEQ ID NO: 2); where each amino acid is indicated by standard one letter abbreviation, "(AcG)" is N-acetylglycine, "(1-nal)" is 1-naphthylalanine, and "(MeG)" is "(MeG)" is N-methylglycine, also known as sarcosine. Each peptide monomer of a peptide dimer contains an intramolecular disulfide bond between the cysteine residues of the monomer. Such monomers may be represented schematically as follows:

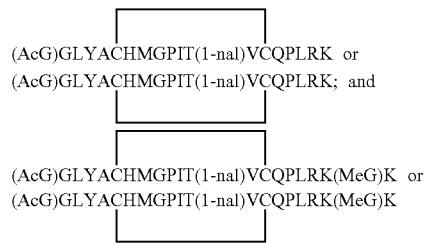

These monomeric peptides are dimerized to provide peptide dimers of enhanced EPO-R agonist activity. The linker ($L_K$) moiety is a branched teriary amide, which bridges the C-termini of two peptide monomers, by simultaneous attachment to the C-terminal lysine residue of each monomer. The tertiary amide linker can be depicted as:

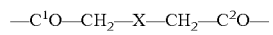

where: X is NCO—$(CH_2)_2$—$N^1H$—; $C^1$ of the linker forms an amide bond with the ε-amino group of the C-terminal lysine residue of the first peptide monomer; $C^2$ of the linker forms an amide bond with the ε-amino group of the C-terminal lysine residue of the second peptide monomer; and $N^1$ of X is attached via a carbamate linkage or an amide linkage to an activated polyethylene glycol (PEG) moiety, where the PEG has a molecular weight of about 20,000 to about 40,000 Daltons (the term "about" indicating that in preparations of PEG, some molecules will weigh more, some less, than the stated molecular weight).

The tertiary amide linker may also be depicted as:

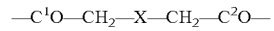

where: X is NCO—$(CH_2)_2$—NH—$C^3$—; $C^1$ of the linker forms an amide bond with the ε-amino group of the C-terminal lysine residue of the first peptide monomer; and $C^2$ of the linker forms an amide bond with the ε-amino group of the C-terminal lysine residue of the second peptide monomer. The peptide dimers of the invention further comprise a spacer moiety of the following structure:

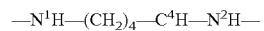

where: $C^4$ of the spacer is covalently bonded to $C^3$ of X; $N^1$ of the spacer is covalently attached via a carbamate or an amide linkage to an activated PEG moiety; and $N^2$ of the spacer is covalently attached via a carbamate or an amide linkage to an activated PEG moiety, where PEG has a molecular weight of about 10,000 to about 60,000 Daltons (the term "about" indicating that in preparations of PEG, some molecules will weigh more, some less, than the stated molecular weight).

Thus, the novel peptides of the invention can also contain a PEG moiety, which is covalently attached via a carbamate linkage or an amide linkage to the tertiary amide linker of the peptide dimer. PEG is a water soluble polymer that is pharmaceutically acceptable. PEG for use in the present invention may be linear, unbranched PEG having a molecular weight of about 20 kilodaltons (20K) to about 60K (the term "about" indicating that in preparations of PEG, some molecules will weigh more, some less, than the stated molecular weight). Most preferably, the PEG has a molecular weight of about 30K to about 40K. One skilled in the art will be able to select the desired polymer size based on such considerations as the desired dosage; circulation time; resistance to proteolysis; effects, if any, on biological activity; ease in handling; degree or lack of antigenicity; and other known effects of PEG on a therapeutic peptide.

Peptides, peptide dimers and other peptide-based molecules of the invention can be attached to water-soluble polymers (e.g., PEG) using any of a variety of chemistries to link the water-soluble polymer(s) to the receptor-binding portion of the molecule (e.g., peptide+spacer). A typical embodiment employs a single attachment junction for covalent attachment of the water soluble polymer(s) to the receptor-binding portion, however in alternative embodiments multiple attachment junctions may be used, including further variations wherein different species of water-soluble polymer are attached to the receptor-binding portion at distinct attachment junctions, which may include covalent attachment junction(s) to the spacer and/or to one or both peptide chains. In some embodiments, the dimer or higher order multimer will comprise distinct species of peptide chain (i.e., a heterodimer or other heteromultimer). By way of example and not limitation, a dimer may comprise a first peptide chain having a PEG attachment junction and the second peptide chain may either lack a PEG attachment junction or utilize a different linkage chemistry than the first peptide chain and in some variations the spacer may contain or lack a PEG attachment junction and said spacer, if PEGylated, may utilize a linkage chemistry different than that of the first and/or second peptide chains. An alternative embodiment employs a PEG attached to the spacer portion of the receptor-binding portion and a different water-soluble polymer (e.g., a carbohydrate) conjugated to a side chain of one of the amino acids of the peptide portion of the molecule.

A wide variety of polyethylene glycol (PEG) species may be used for PEGylation of the receptor-binding portion (peptides+spacer). Substantially any suitable reactive PEG reagent can be used. In preferred embodiments, the reactive PEG reagent will result in formation of a carbamate or amide bond upon conjugation to the receptor-binding portion. Suitable reactive PEG species include, but are not limited to, those which are available for sale in the Drug Delivery Systems catalog (2003) of NOF Corporation (Yebisu Garden Place Tower, 20-3 Ebisu 4-chome, Shibuya-ku, Tokyo 150-6019) and the Molecular Engineering catalog (2003) of Nektar Therapeutics (490 Discovery Drive, Huntsville, Ala. 35806). For example and not limitation, the following PEG reagents are often preferred in various embodiments: mPEG2-NHS, mPEG2-ALD, multi-Arm PEG, mPEG (MAL)2, mPEG2(MAL), mPEG-NH2, mPEG-SPA, mPEG-SBA, mPEG-thioesters, mPEG-Double Esters, mPEG-BTC, mPEG-ButyrALD, mPEG-ACET, heterofunctional PEGs (NH2-PEG-COOH, Boc-PEG-NHS, Fmoc-PEG-NHS, NHS-PEG-VS, NHS-PEG-MAL), PEG acrylates (ACRL-PEG-NHS), PEG-phospholipids (e.g., mPEG-DSPE), multiarmed PEGs of the SUNBRITE series including the GL series of glycerine-based PEGs activated by a chemistry chosen by those skilled in the art, any of the SUNBRITE activated PEGs (including but not limited to carboxyl-PEGs, p-NP-PEGs, Tresyl-PEGs, aldehyde PEGs, acetal-PEGs, amino-PEGs, thiol-PEGs, maleimido-PEGs, hydroxyl-PEG-amine, amino-PEG-COOH, hydroxyl-PEG-aldehyde, carboxylic anhydride type-PEG, functionalized PEG-phospholipid, and other similar and/or suitable reactive PEGs as selected by those skilled in the art for their particular application and usage.

The novel peptides of the invention can also contain two PEG moieties that are covalently attached via a carbamate or an amide linkage to a spacer moiety, wherein the spacer moiety is covalently bonded to the tertiary amide linker of the peptide dimer. Each of the two PEG moieties used in such embodiments of the present invention may be linear and may be linked together at a single point of attachment. Each PEG moiety preferably has a molecular weight of about 10 kilodaltons (10K) to about 60K (the term "about" indicating that in preparations of PEG, some molecules will weigh more, some less, than the stated molecular weight). Linear PEG moieties are particularly preferred. More preferably, each of the two PEG moieties has a molecular weight of about 20K to about 40K, and still more preferably between about 20K and about 40K. Still more preferably, each of the two PEG moieties has a molecular weight of about 20K. One skilled in the art will be able to select the desired polymer size based on such considerations as the desired dosage; circulation time; resistance to proteolysis; effects, if any, on biological activity; ease in handling; degree or lack of antigenicity; and other known effects of PEG on a therapeutic peptide.

The present invention also comprises peptide agonists that are homodimers of peptide monomers having the amino acid sequence (AcG)GLYACHMGPIT(1-nal)VCQPLR(MeG) (SEQ ID NO: 3), where each amino acid is indicated by standard one letter abbreviation, "(AcG)" is N-acetylglycine, "(1-nal)" is 1-naphthylalanine, and "(MeG)" is N-methylglycine, also known as sarcosine. Each peptide monomer of the peptide dimer contains an intramolecular disulfide bond between the cysteine residues of the monomer. Such monomers may be represented schematically as follows:

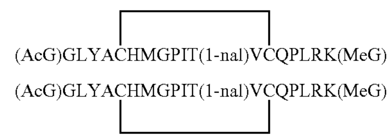

or

These monomeric peptides are dimerized to provide peptide dimers of enhanced EPO-R agonist activity. The linker ($L_K$) moiety is a lysine residue, which bridges the C-termini of two peptide monomers, by simultaneous attachment to the C-terminal amino acid of each monomer. One peptide monomer is attached at its C-terminus to the lysine's ε-amino group and the second peptide monomer is attached at its C-terminus to the lysine's α-amino group. For example, the dimer may be illustrated structurally as shown in Formula I, and summarized as shown in Formula II:

Formula I

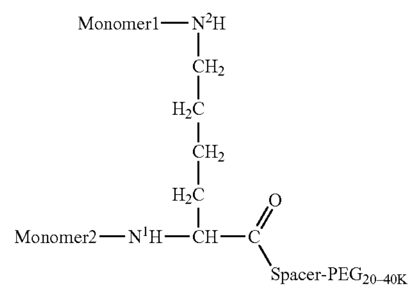

Formula II

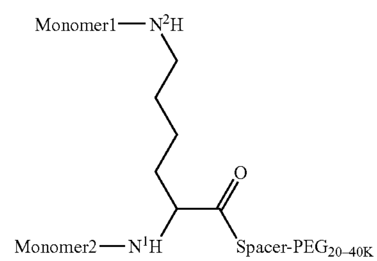

In Formula I and Formula II, $N^2$ represents the nitrogen atom of lysine's ε-amino group and $N^1$ represents the nitrogen atom of lysine's α-amino group.

The peptide dimers of the invention further comprise a spacer moiety of the following structure:

$$—N^1H—(CH_2)_2—O—(CH_2)_2—O—(CH_2)_2—N^2H—$$

At one end, $N^1$ of the spacer is attached via an amide linkage to a carbonyl carbon of the lysine linker. At the opposite end, $N^2$ of the spacer is attached via a carbamate linkage or an amide linkage to an activated polyethylene glycol (PEG) moiety, where the PEG has a molecular weight of about 10,000 to about 60,000 Daltons (the term "about" indicating that in preparations of PEG, some molecules will weigh more, some less, than the stated molecular weight). More preferably, the PEG has a molecular weight of about 20,000 to 40,000 Daltons.

Thus, the novel peptides of the invention also contain a PEG moiety, which is covalently attached to the peptide dimer. PEG is a water soluble polymer that is pharmaceutically acceptable. PEG for use in the present invention may be linear, unbranched PEG having a molecular weight of about 20 kilodaltons (20K) to about 60K (the term "about" indicating that in preparations of PEG, some molecules will weigh more, some less, than the stated molecular weight). Most preferably, the PEG has a molecular weight of about 20K to about 40K, and still more preferably a molecular weight of about 30K to about 40K. One skilled in the art will be able to select the desired polymer size based on such considerations as the desired dosage; circulation time; resistance to proteolysis; effects, if any, on biological activity; ease in handling; degree or lack of antigenicity; and other known effects of PEG on a therapeutic peptide.

Where each monomer of the homodimer has the amino acid sequence, (AcG)GLYACHMGPIT(1-nal)VCQPLRK (SEQ ID NO: 1) and $N^1$ of the linker is attached via a carbamate linkage to an activated polyethylene glycol (PEG) moiety, the novel peptide compounds of the invention may be represented as follows:

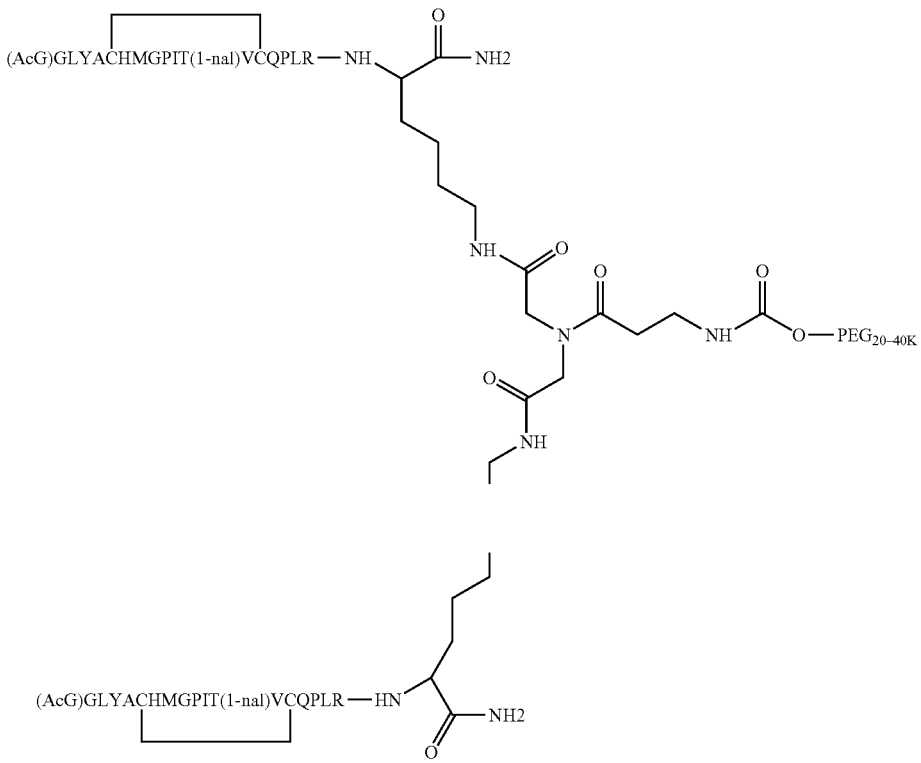

Where each monomer of the homodimer has the amino acid sequence, (AcG)GLYACHMGPIT(1-nal)VCQPLRK (SEQ ID NO: 1) and $N^1$ of the linker is attached via an amide linkage to an activated polyethylene glycol (PEG) moiety, the novel peptide compounds of the invention may be represented as follows:

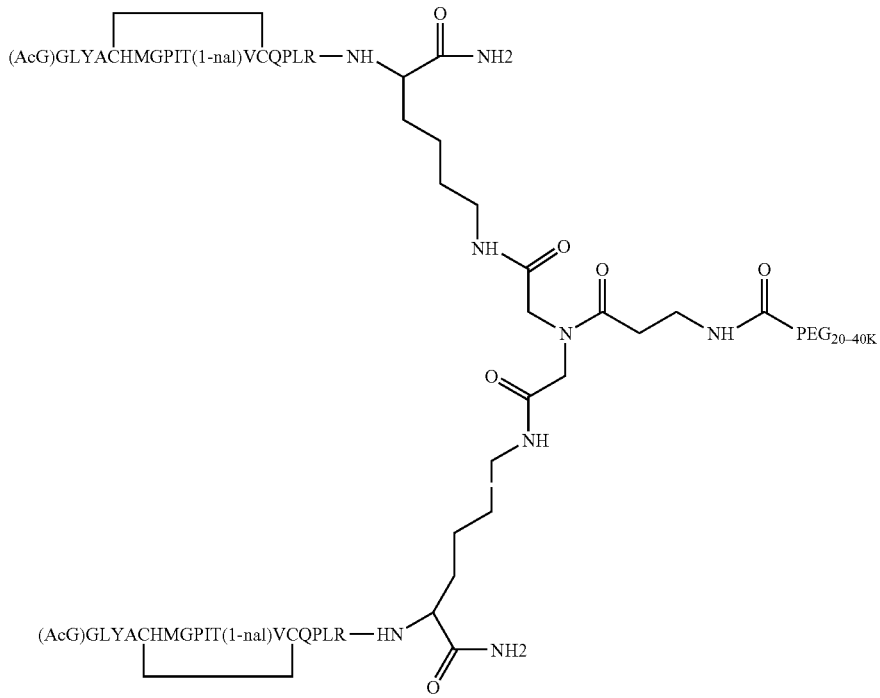

Where each monomer of the homodimer has the amino acid sequence, (AcG)GLYACHMGPIT(1-nal)VCQPLR(MeG)K (SEQ ID NO: 2) and $N^1$ of the linker is attached via a carbamate linkage to an activated polyethylene glycol (PEG) moiety, the novel peptide compounds of the invention may be represented as follows:

Where each monomer of the homodimer has the amino acid sequence, (AcG)GLYACHMGPIT(1-nal)VCQPLR(MeG)K (SEQ ID NO: 2) and $N^1$ of the linker is attached via an amide linkage to an activated polyethylene glycol (PEG) moiety, the novel peptide compounds of the invention may be represented as follows:

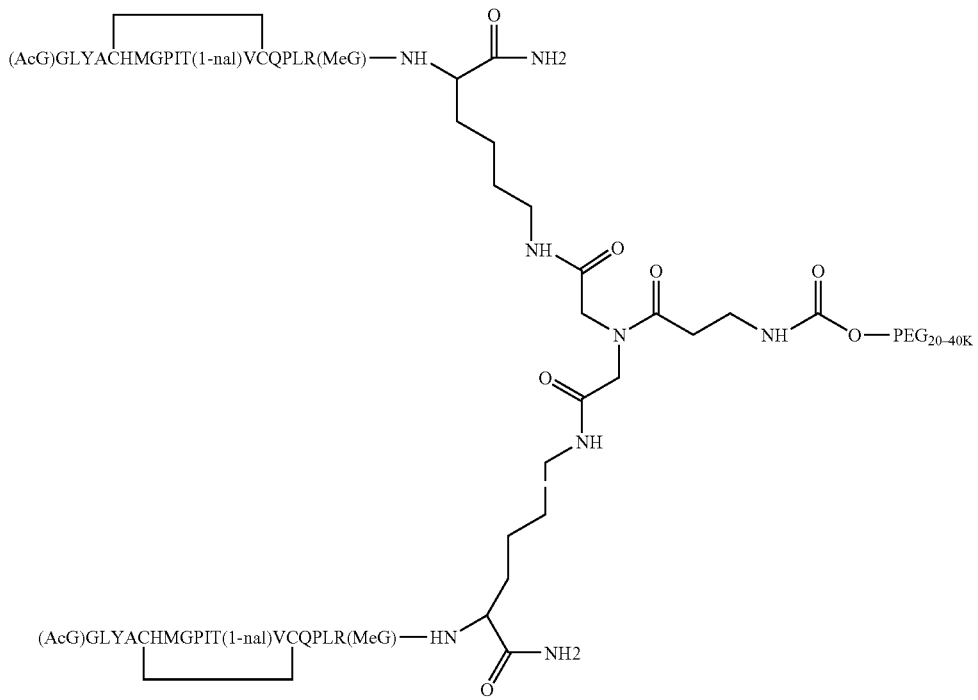

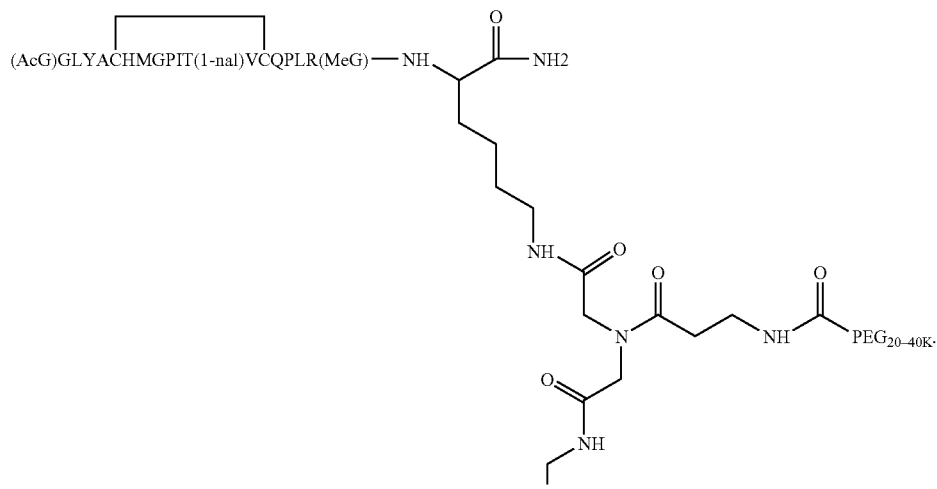
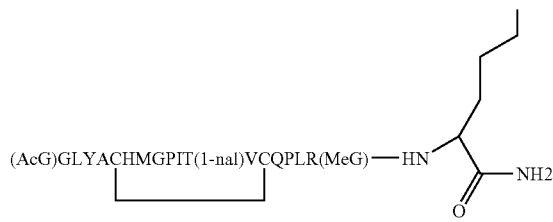
Preferred peptide dimers of the present invention include, but are not limited to:
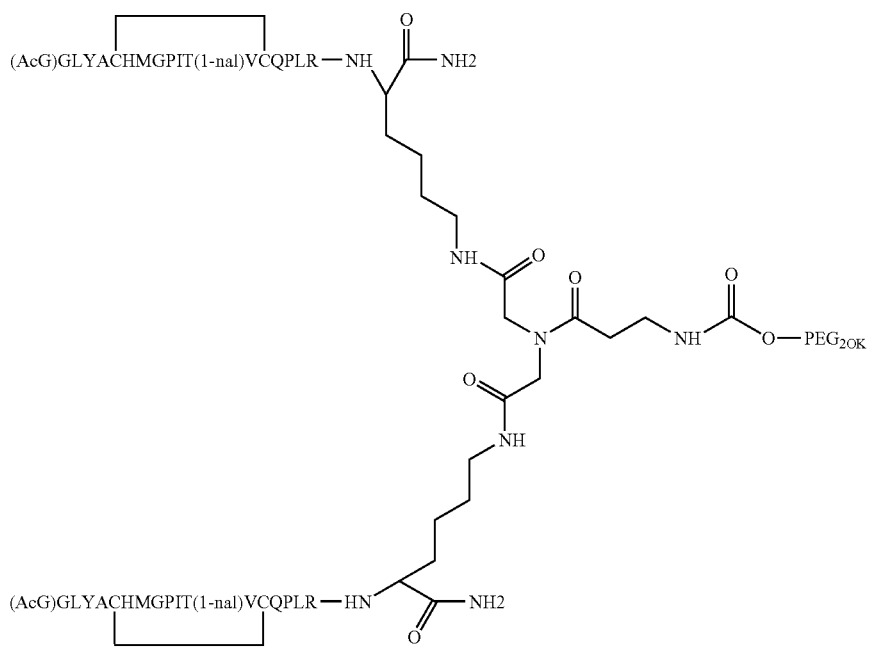

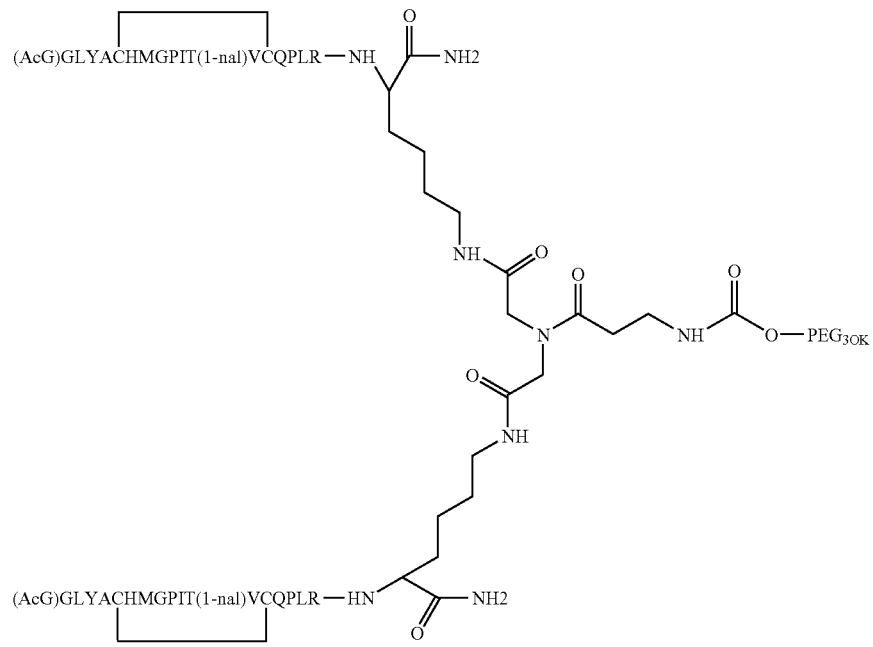
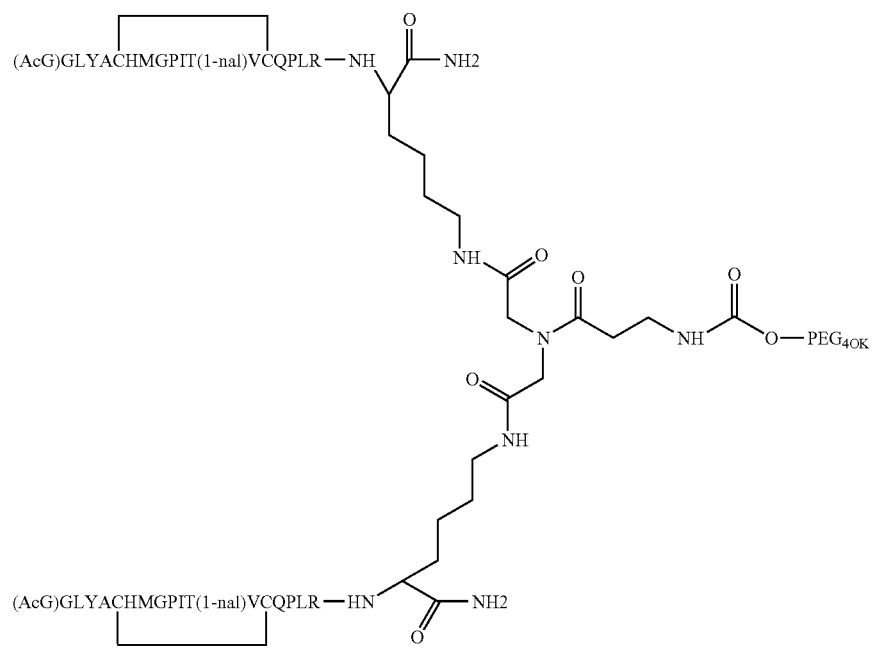

-continued
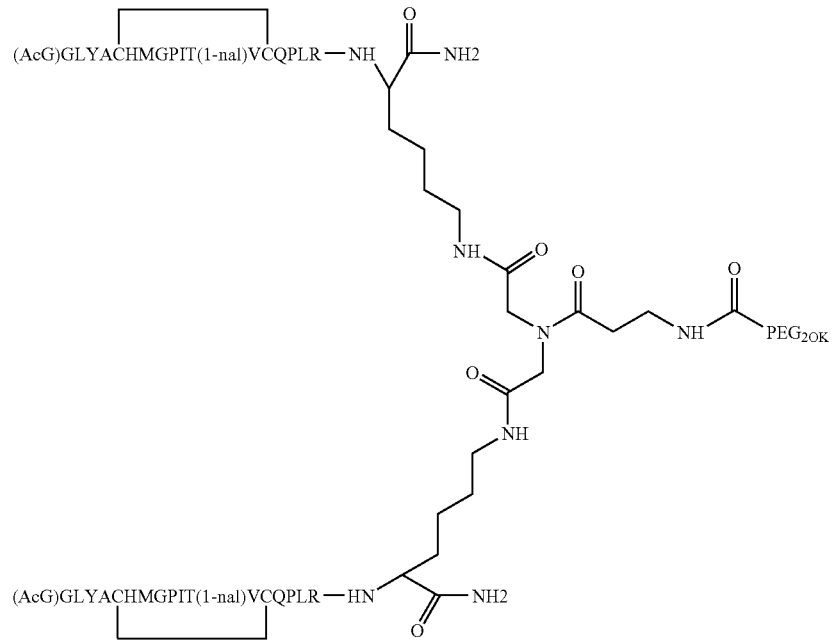
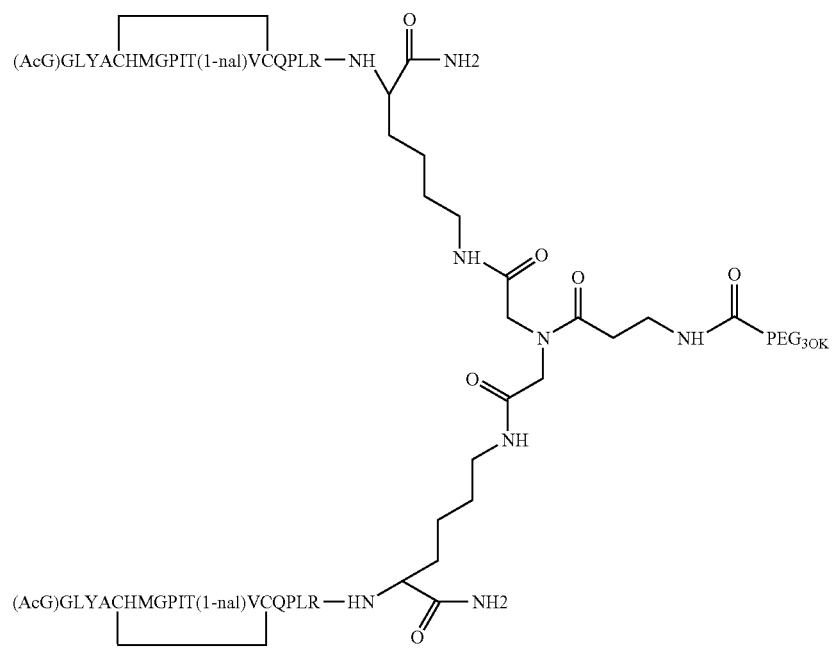

-continued
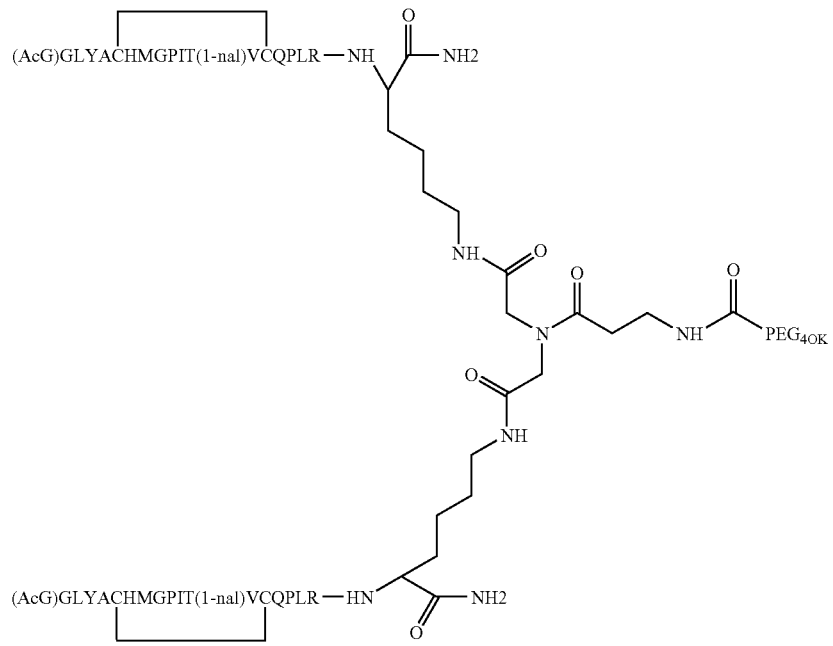
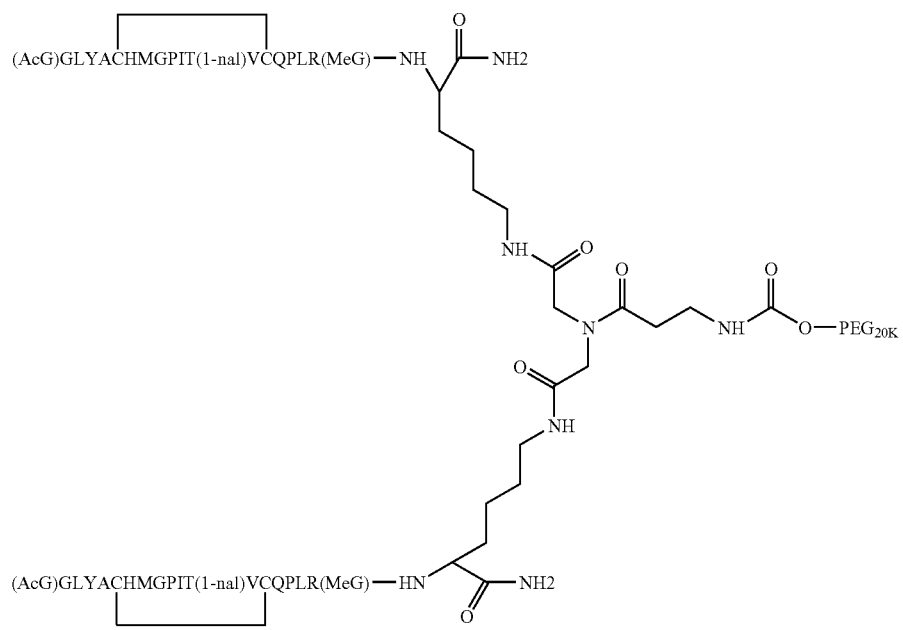

-continued
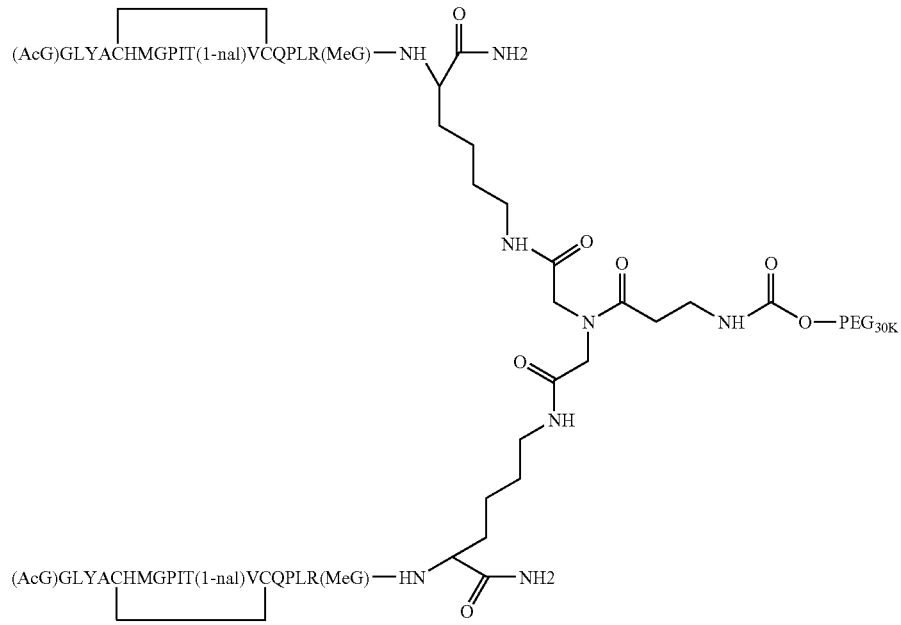
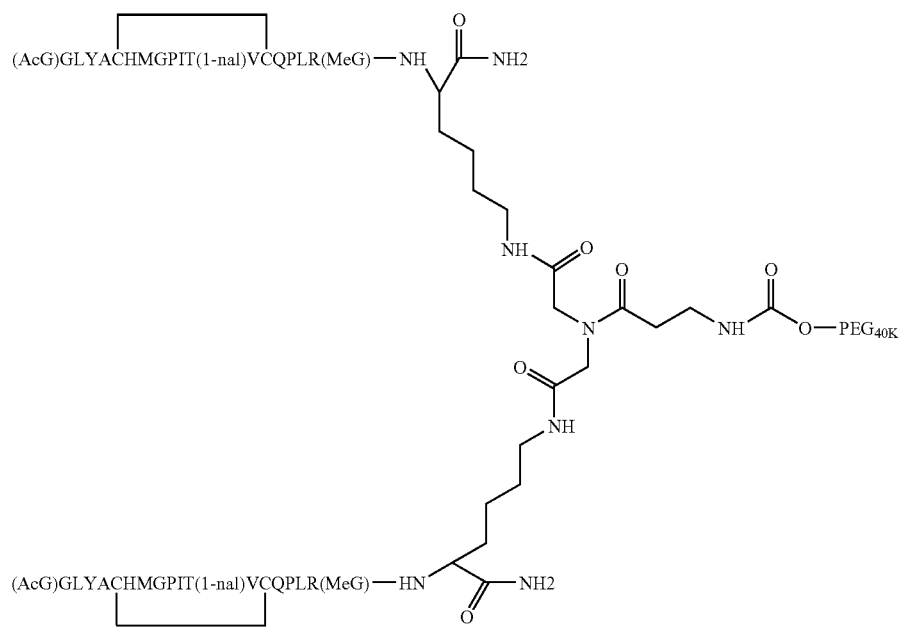

-continued
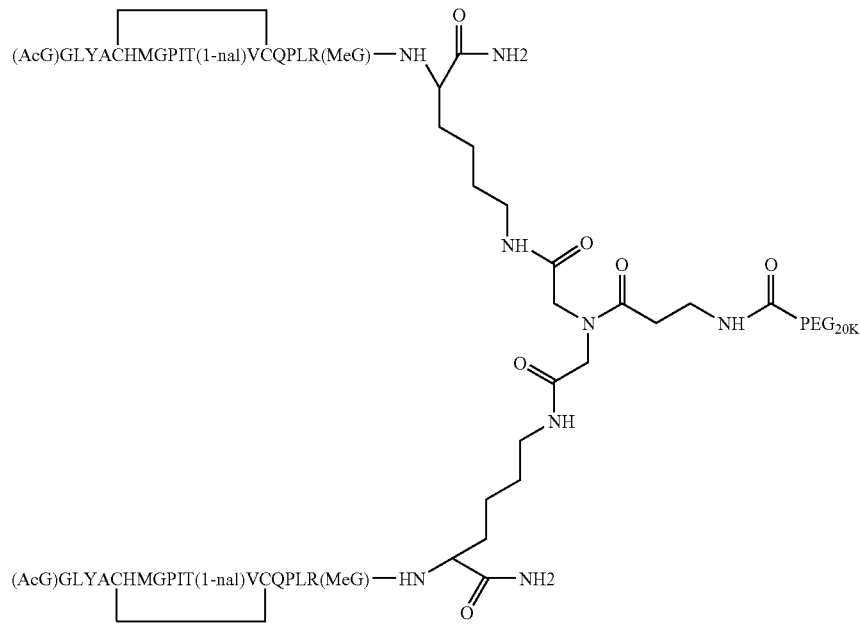
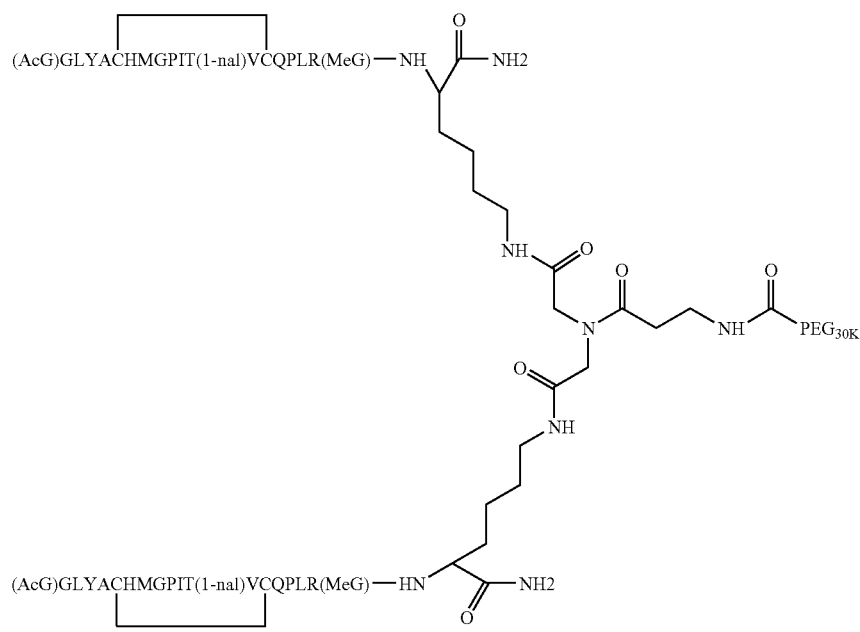

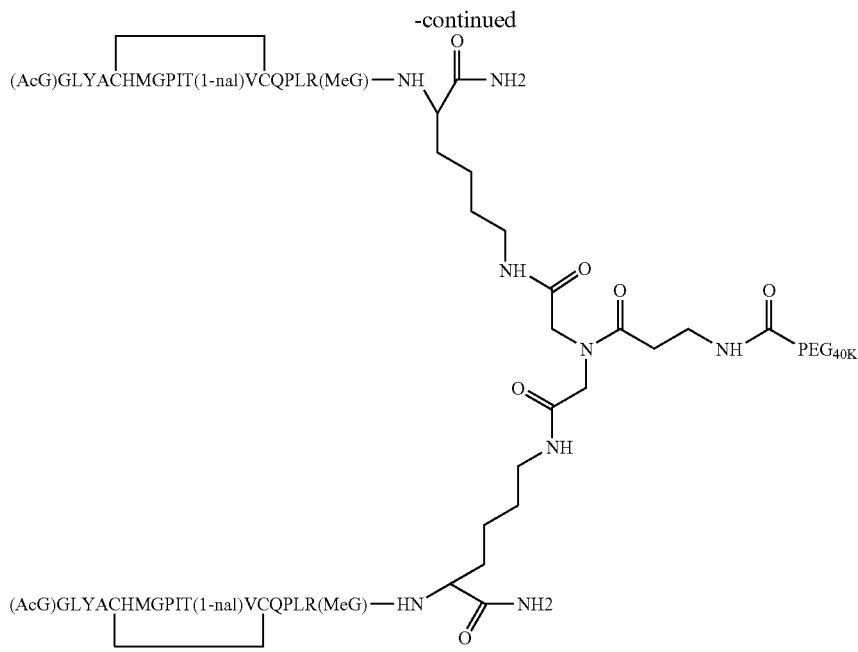

Where each monomer of the homodimer has the amino acid sequence, (AcG)GLYACHMGPIT(1-nal)VCQPLRK (SEQ ID NO: 1) and both $N^1$ and $N^2$ of the spacer are covalently attached via a carbamate linkage to an activated PEG moiety, the novel peptide compounds of the invention may be represented as follows:

Where each monomer of the homodimer has the amino acid sequence, (AcG)GLYACHMGPIT(1-nal)VCQPLRK (SEQ ID NO: 1) and both $N^1$ and $N^2$ of the spacer are covalently attached via an amide linkage to an activated PEG moiety, the novel peptide compounds of the invention may be represented as follows:

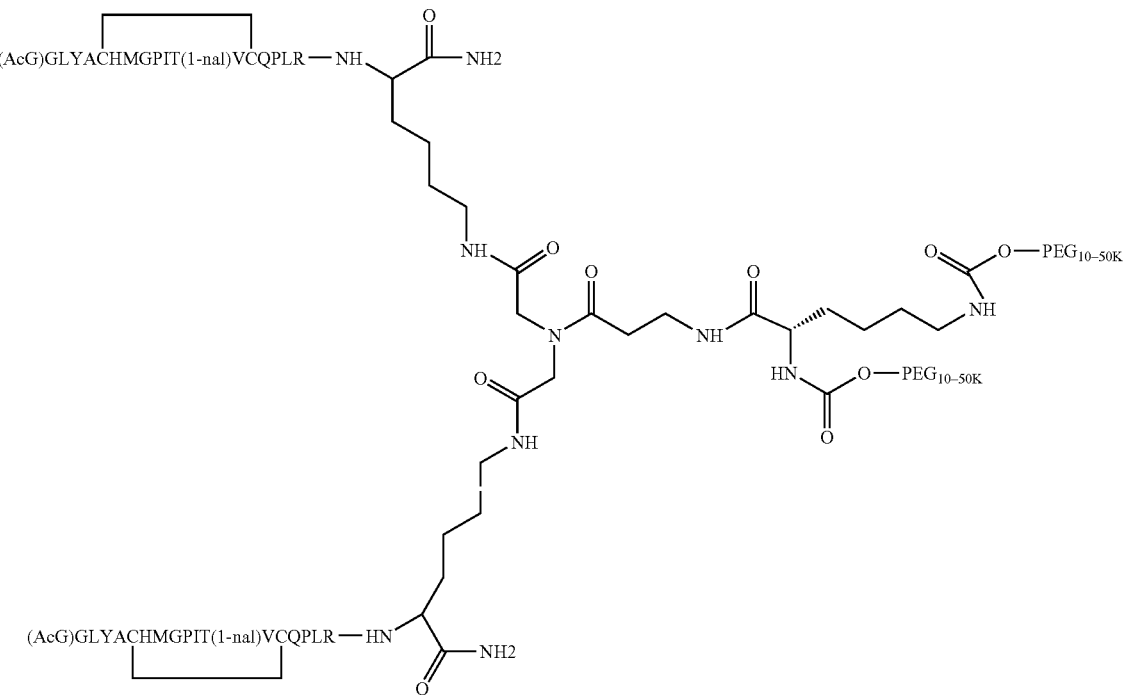

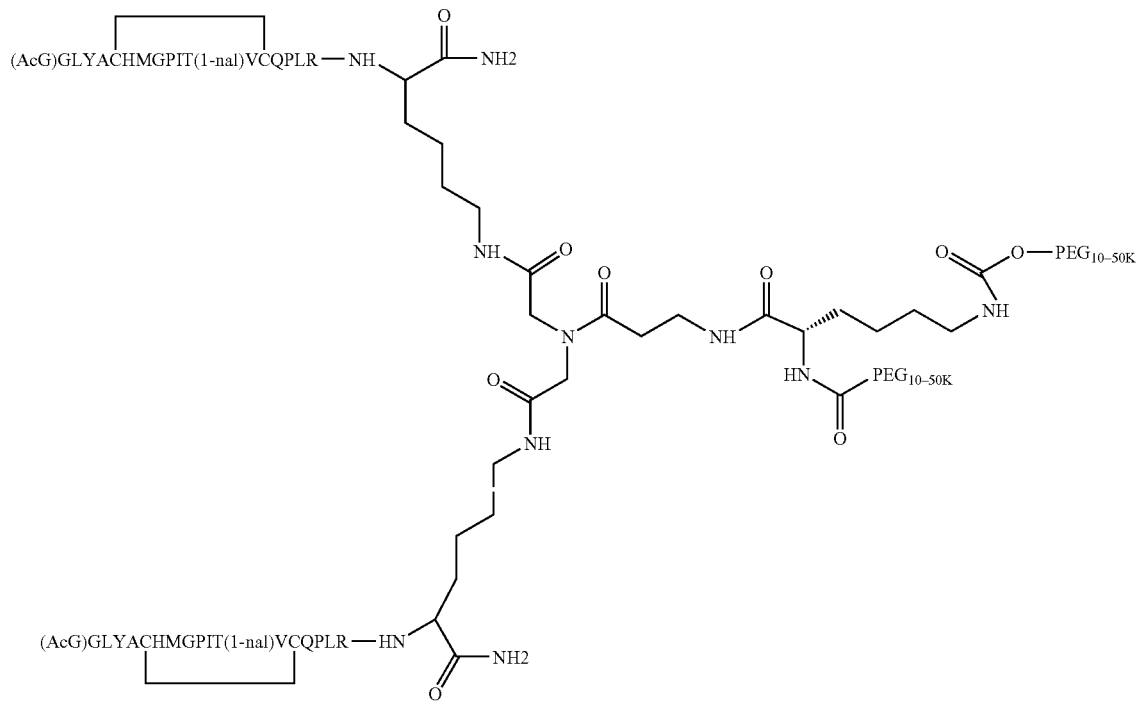

Where each monomer of the homodimer has the amino acid sequence, (AcG)GLYACHMGPIT(1-nal)VCQPLR(MeG)K (SEQ ID NO: 2) and both $N^1$ and $N^2$ of the spacer are covalently attached via a carbamate linkage to an activated PEG moiety, the novel peptide compounds of the invention may be represented as follows:

Where each monomer of the homodimer has the amino acid sequence, (AcG)GLYACHMGPIT(1-nal)VCQPLR(MeG)K (SEQ ID NO: 2) and both $N^1$ and $N^2$ of the spacer are covalently attached via an amide linkage to an activated PEG moiety, the novel peptide compounds of the invention may be represented as follows:

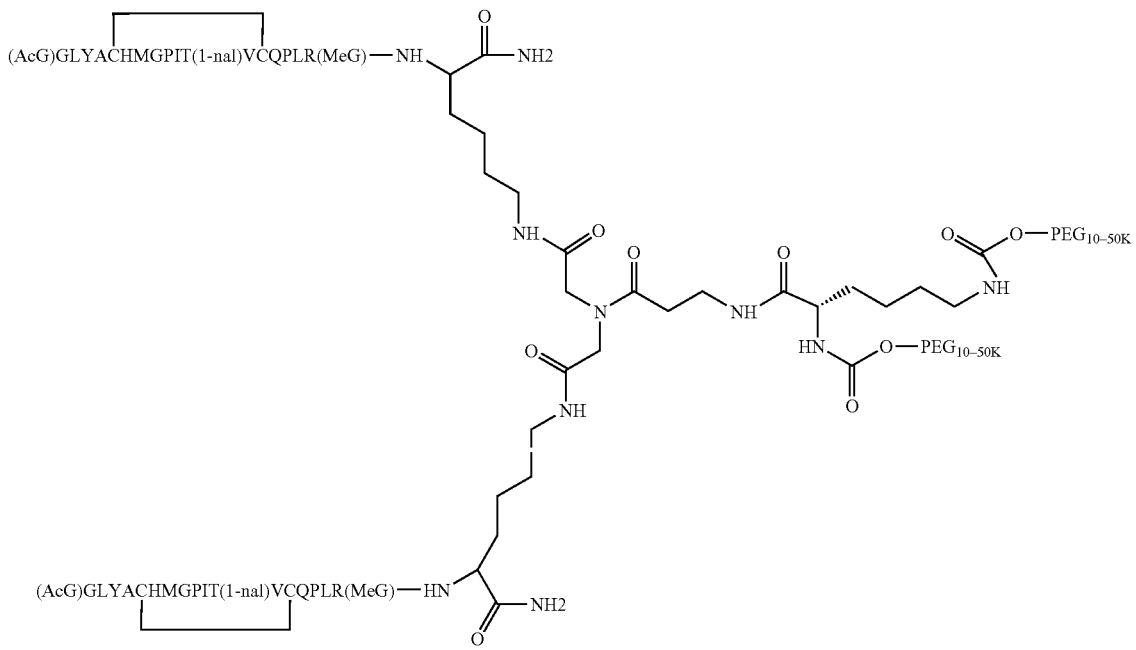

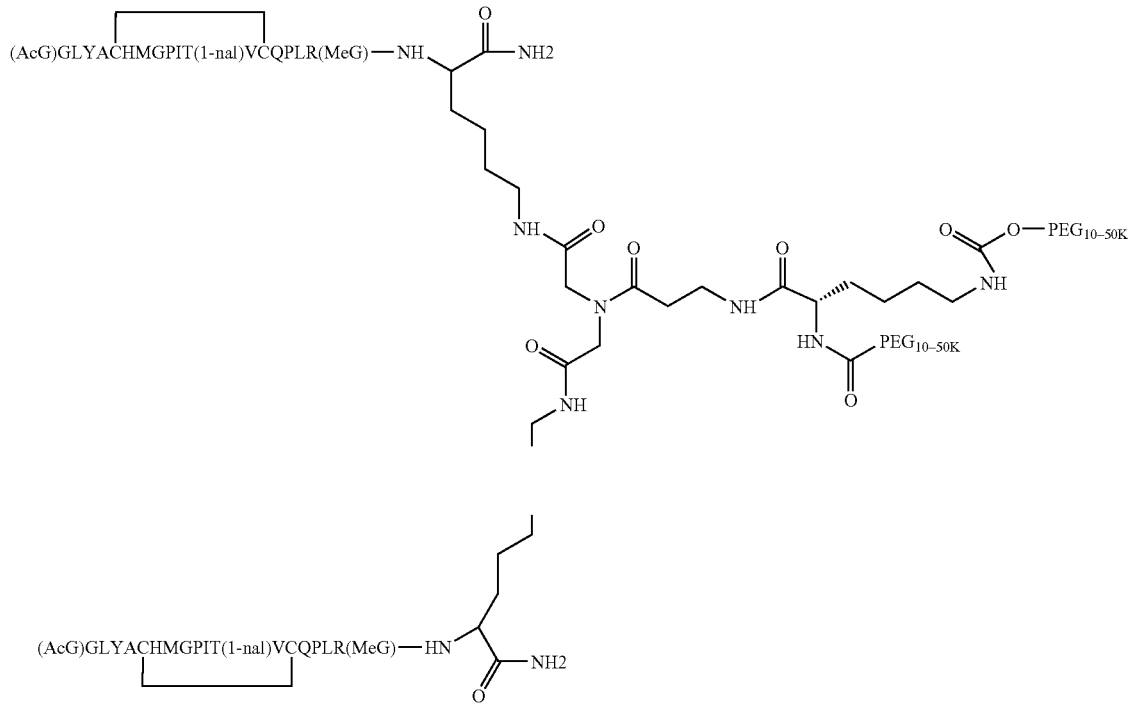
Preferred peptide dimers of the present invention include, but are not limited to:
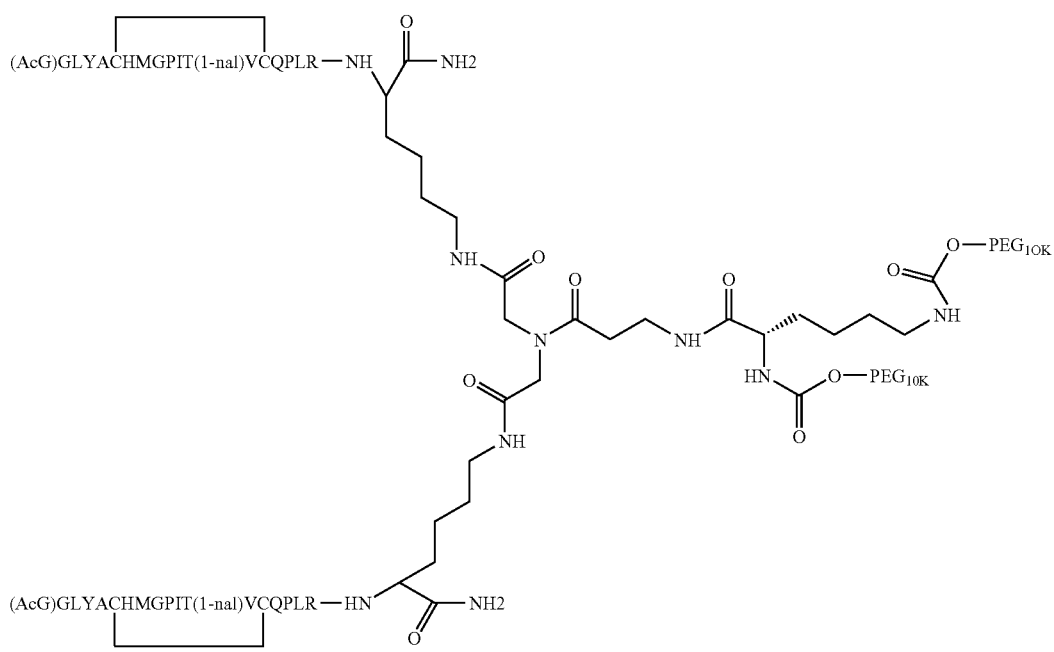

-continued
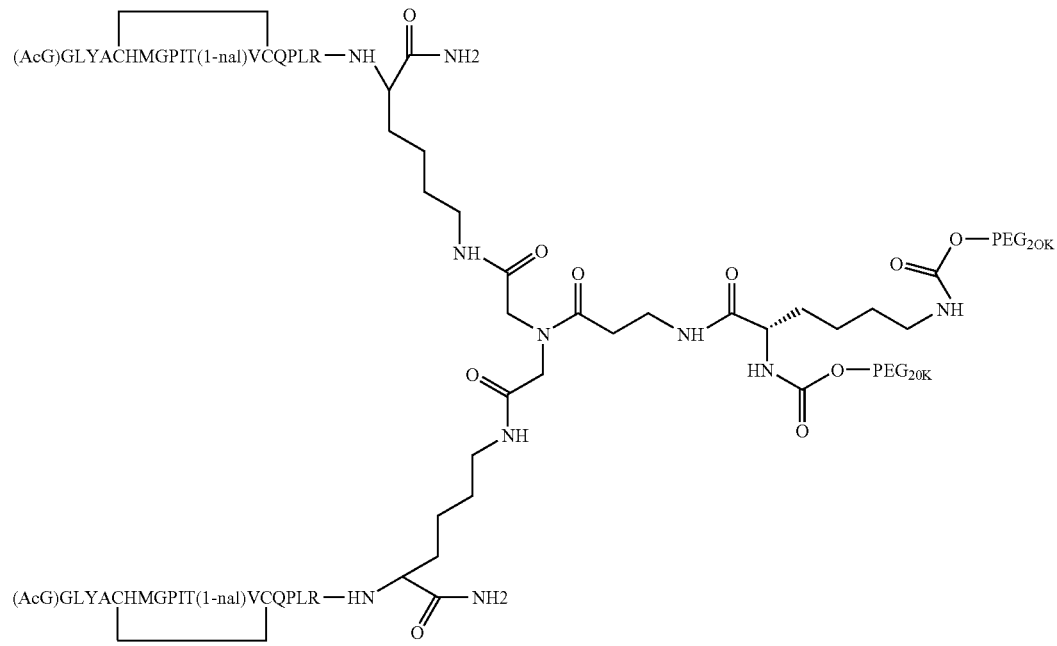
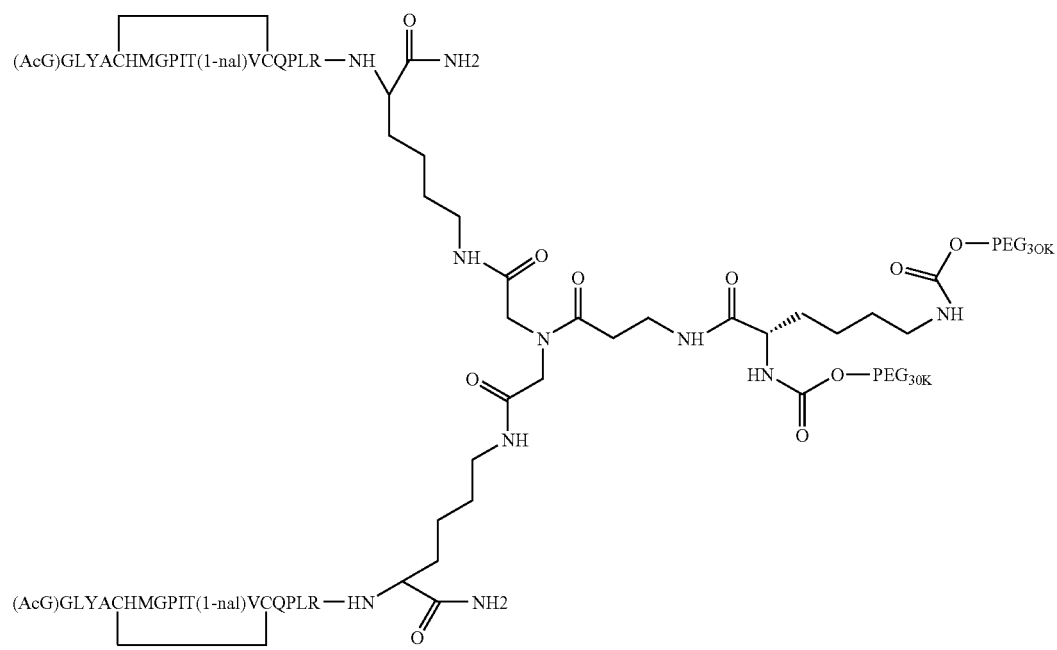

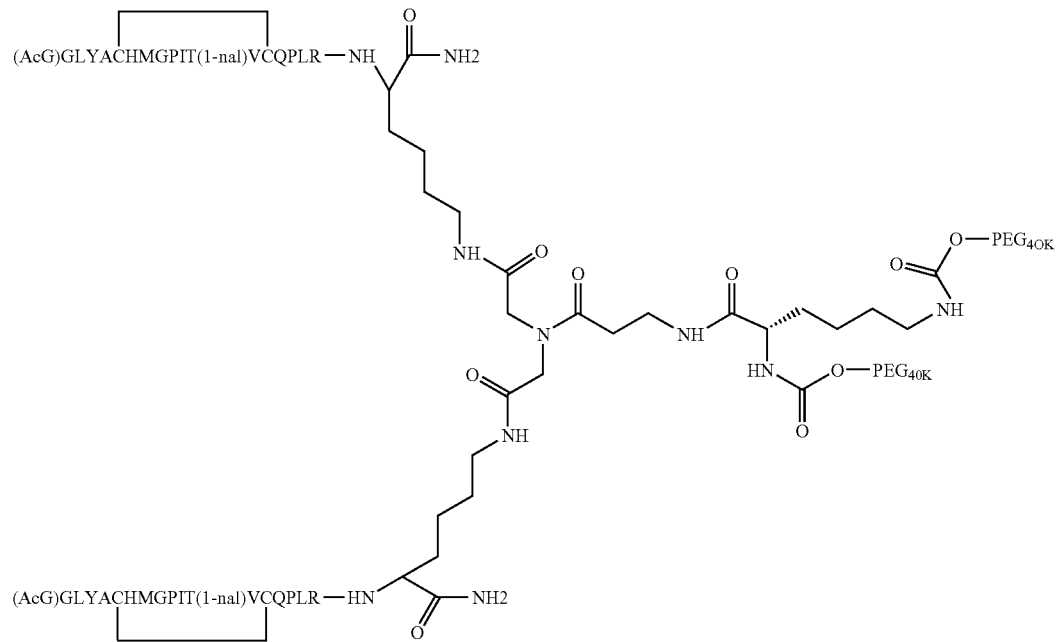
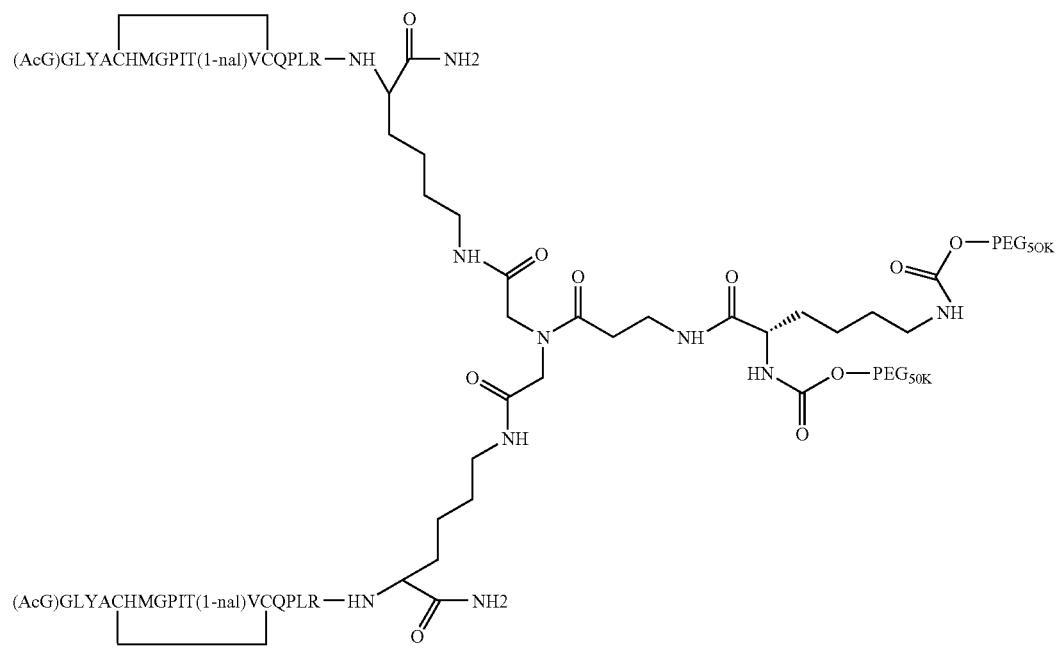

-continued
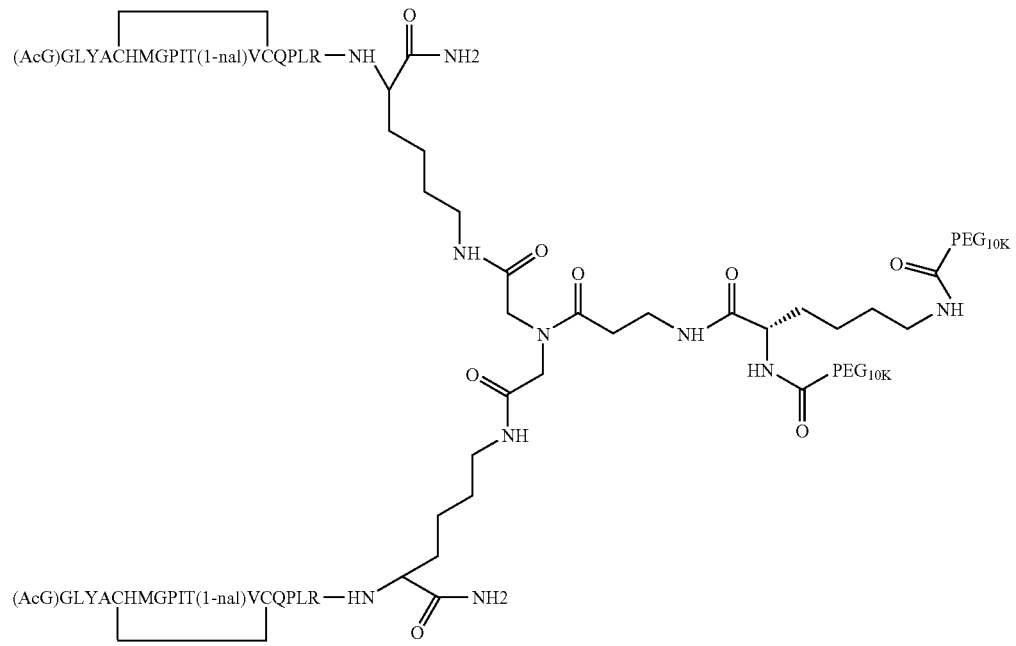
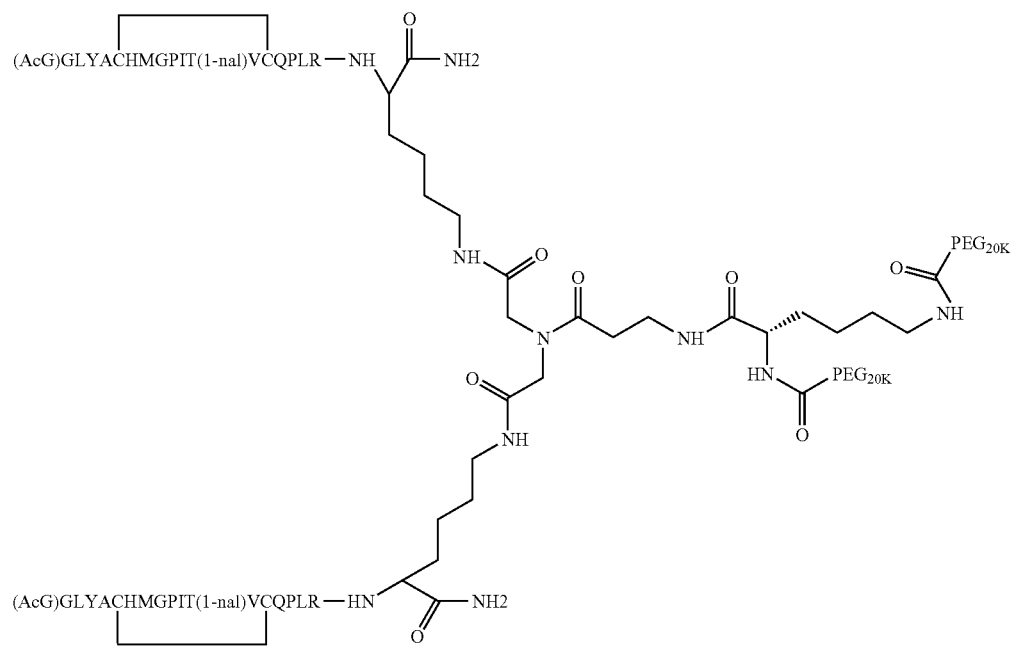

-continued
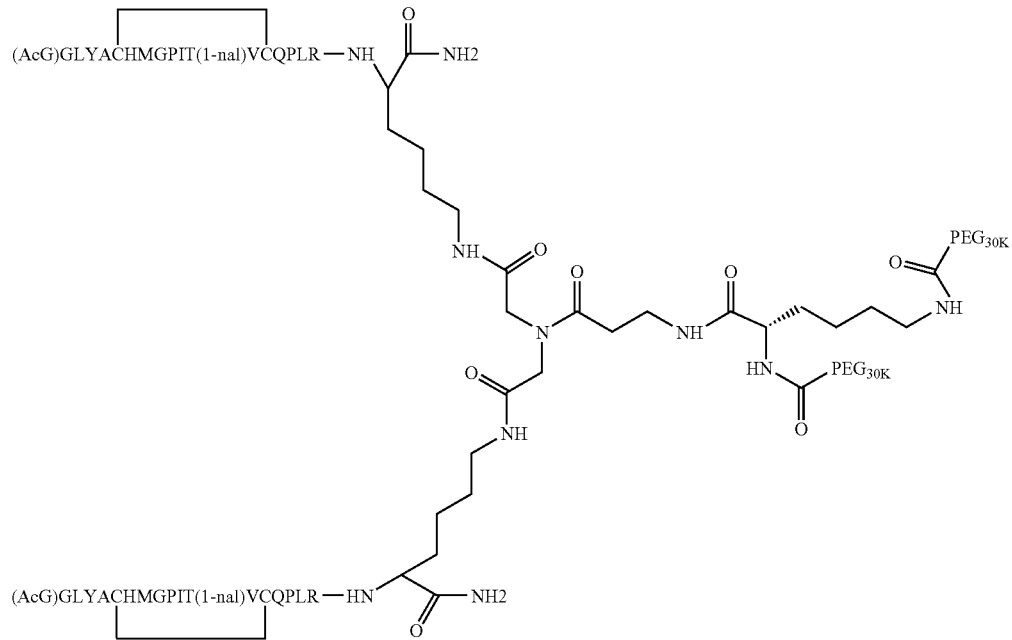
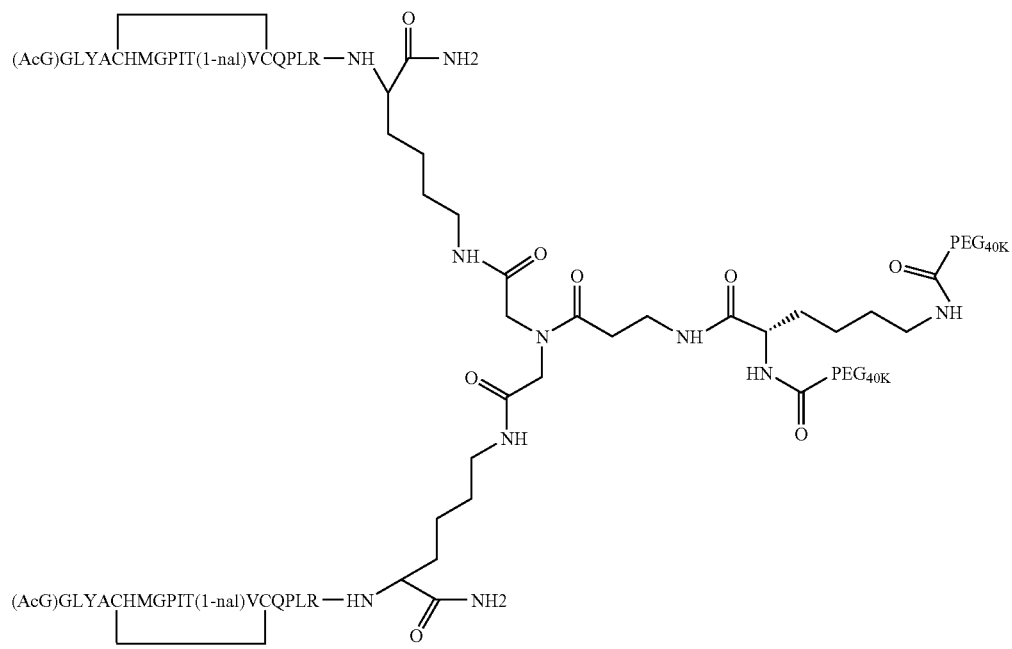

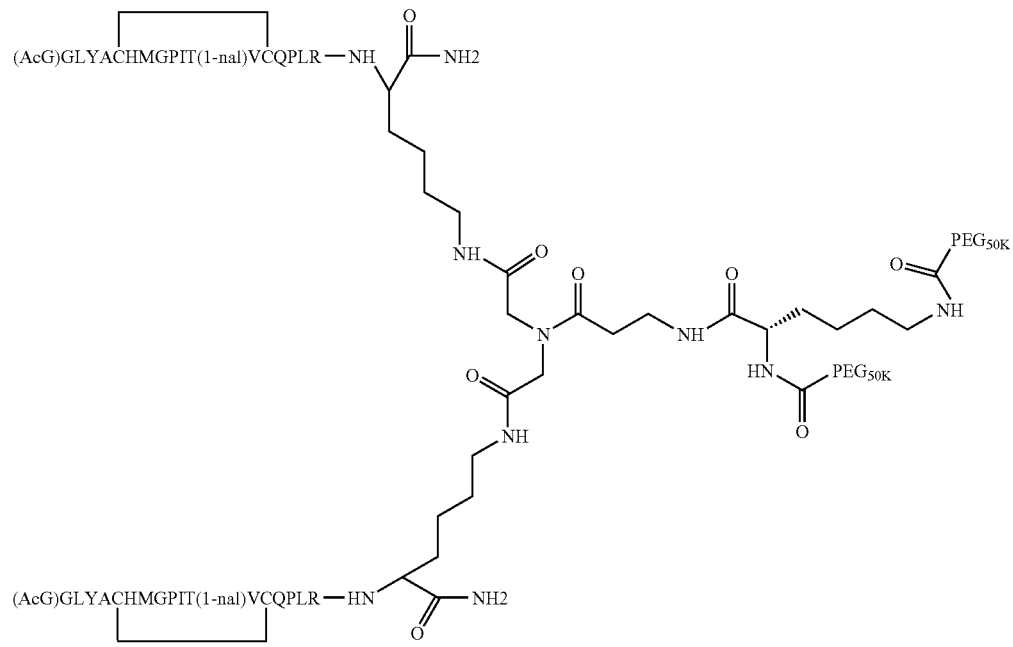
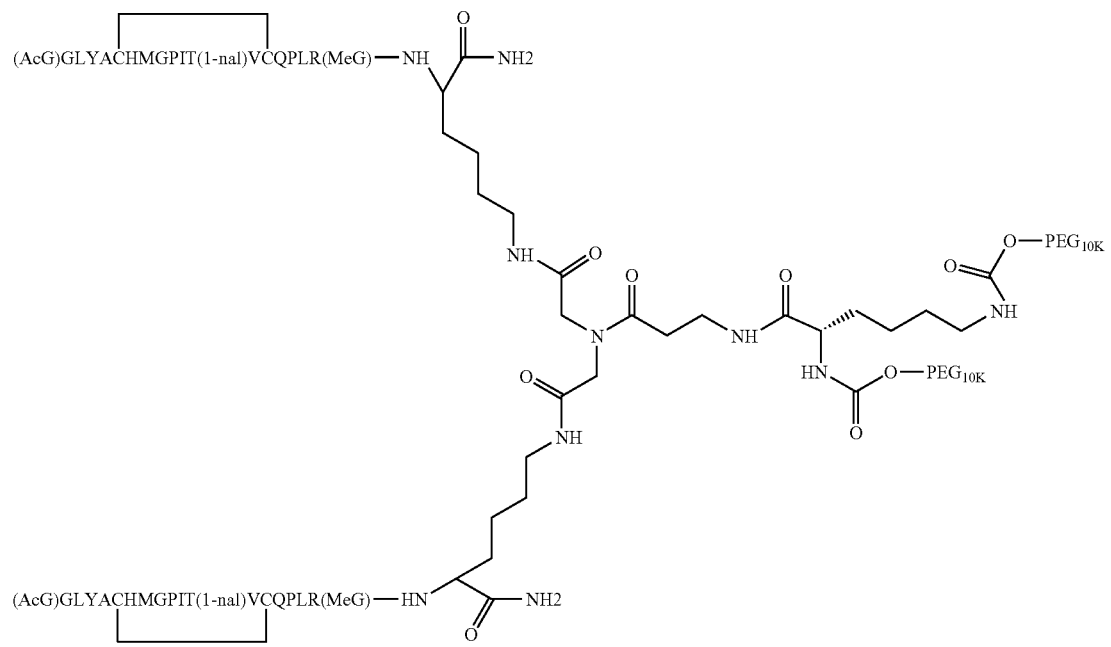

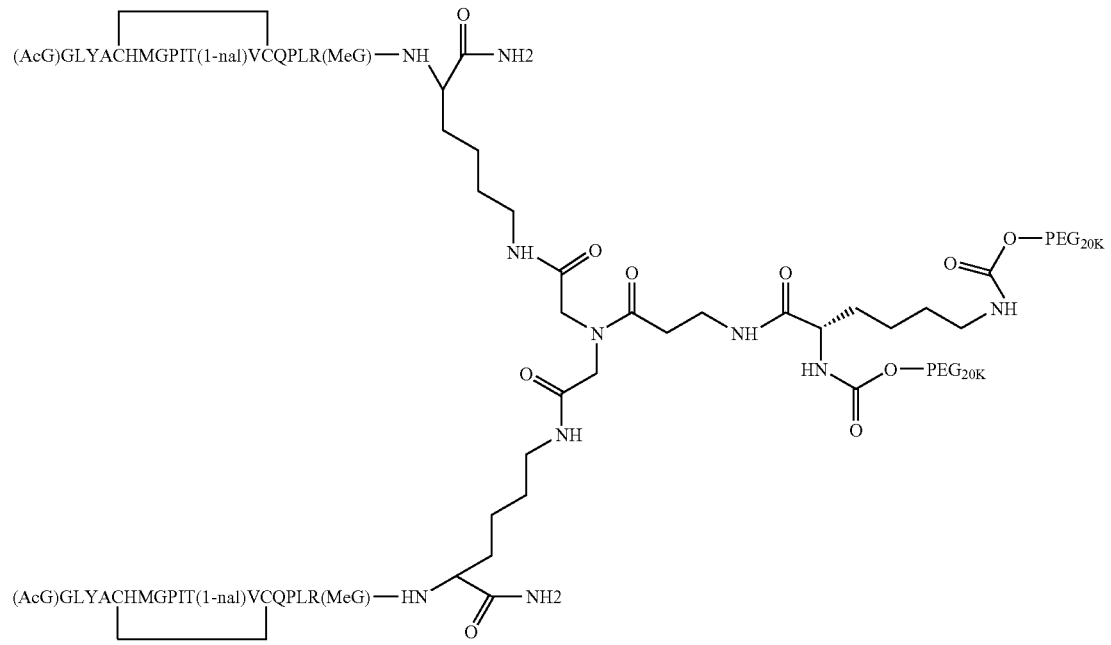
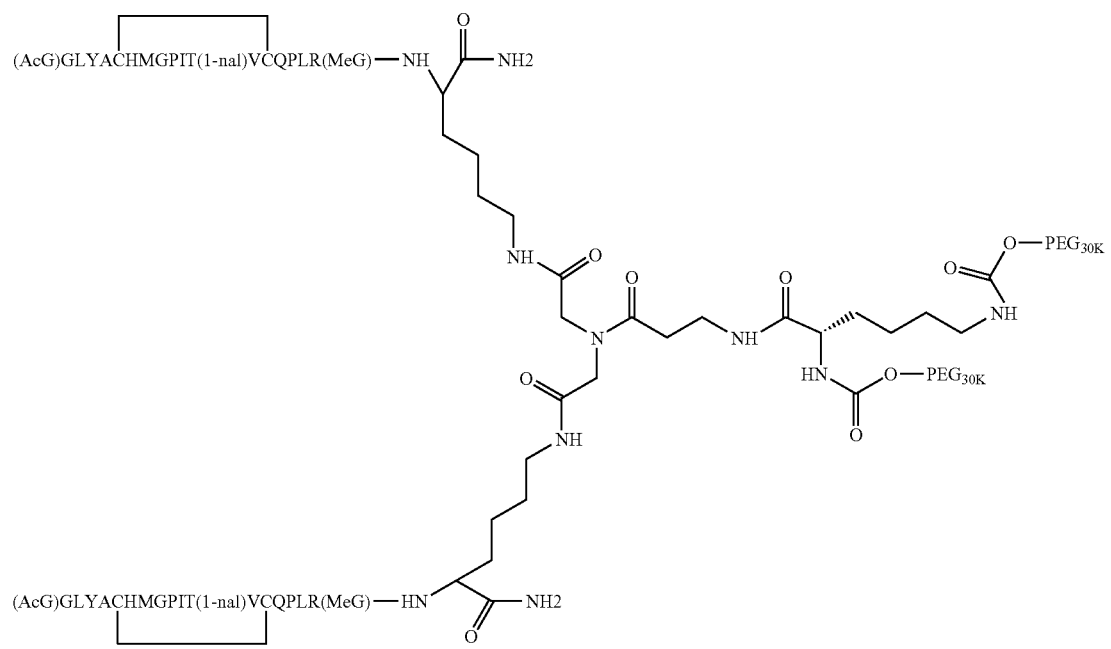

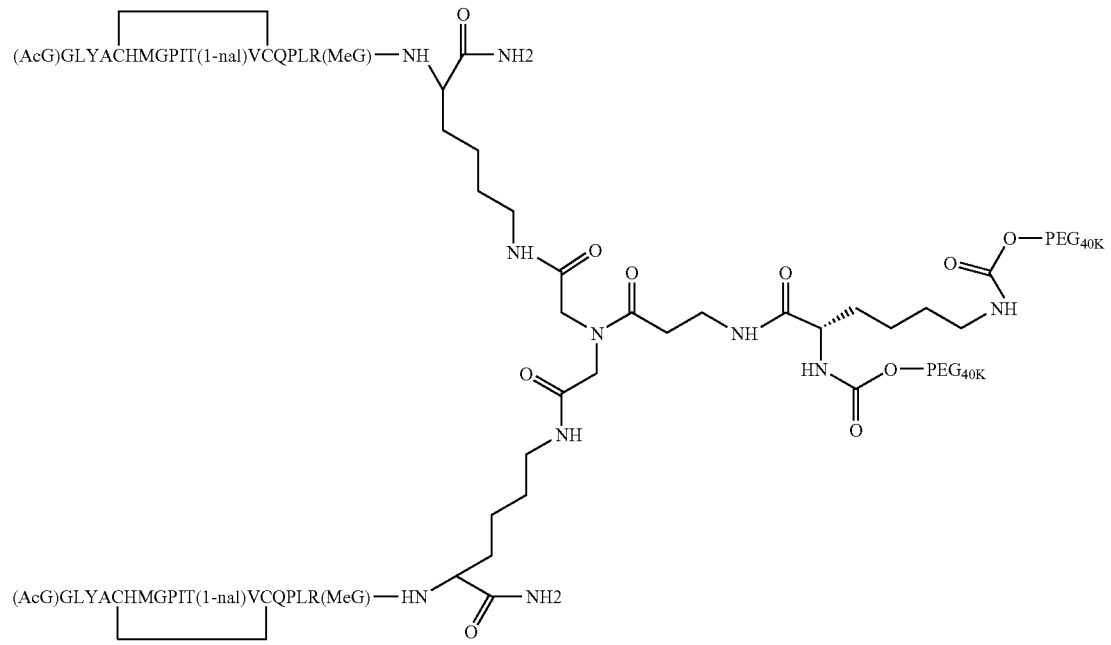
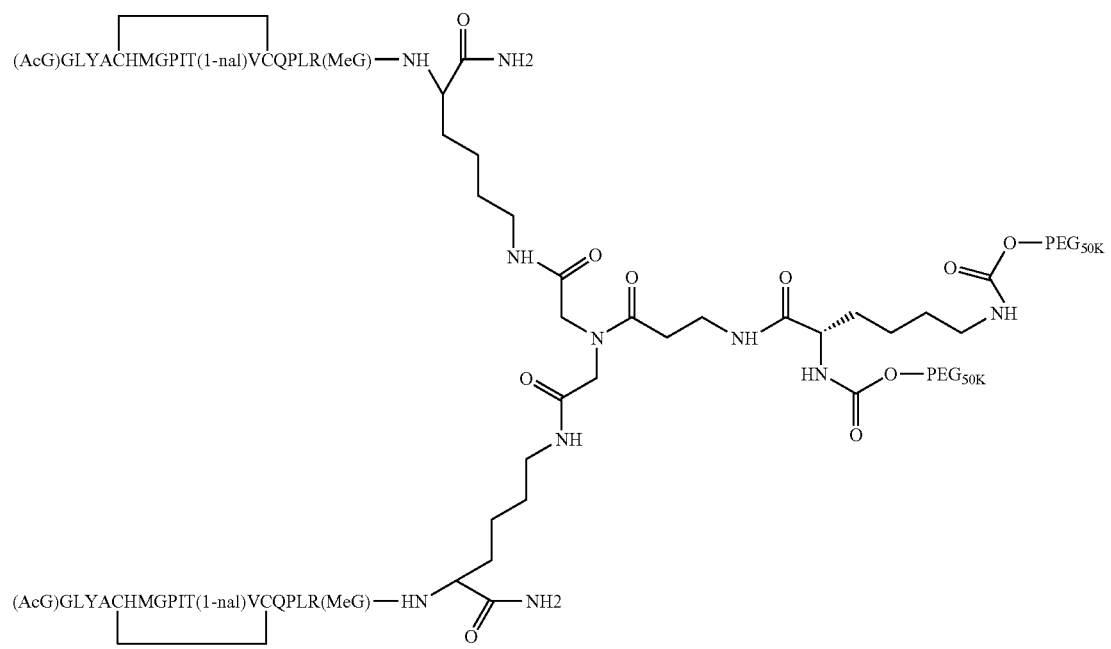

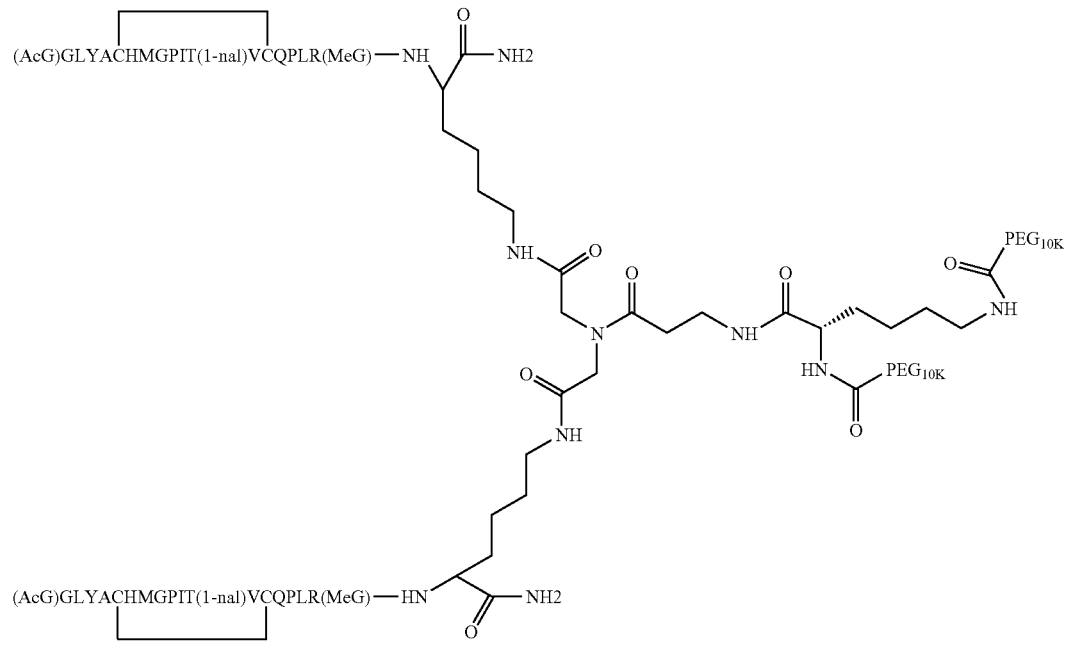
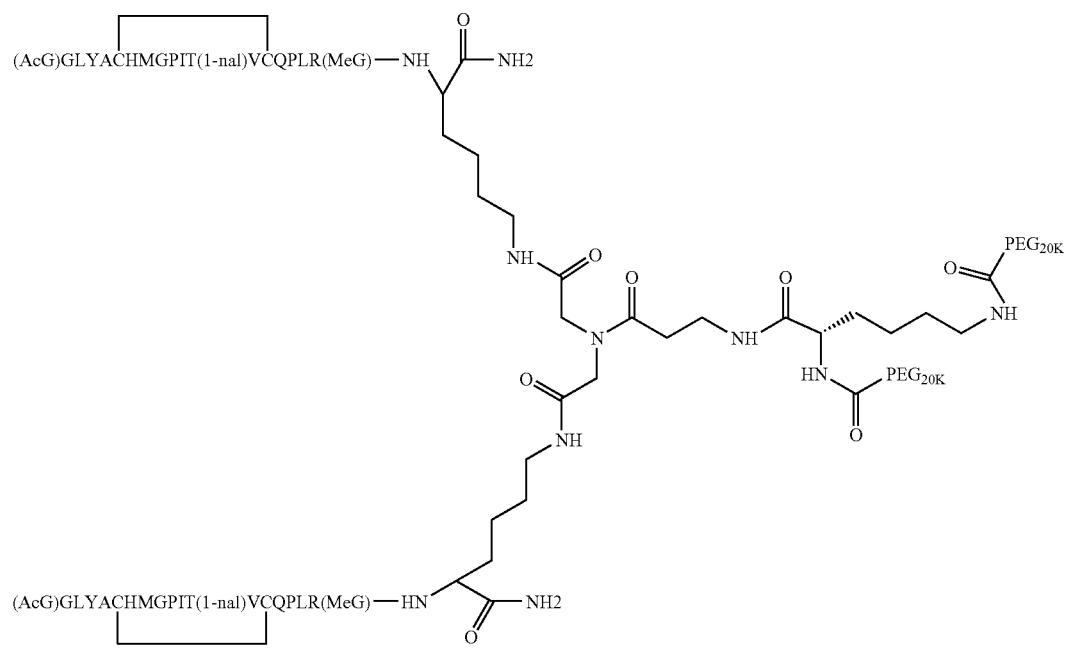

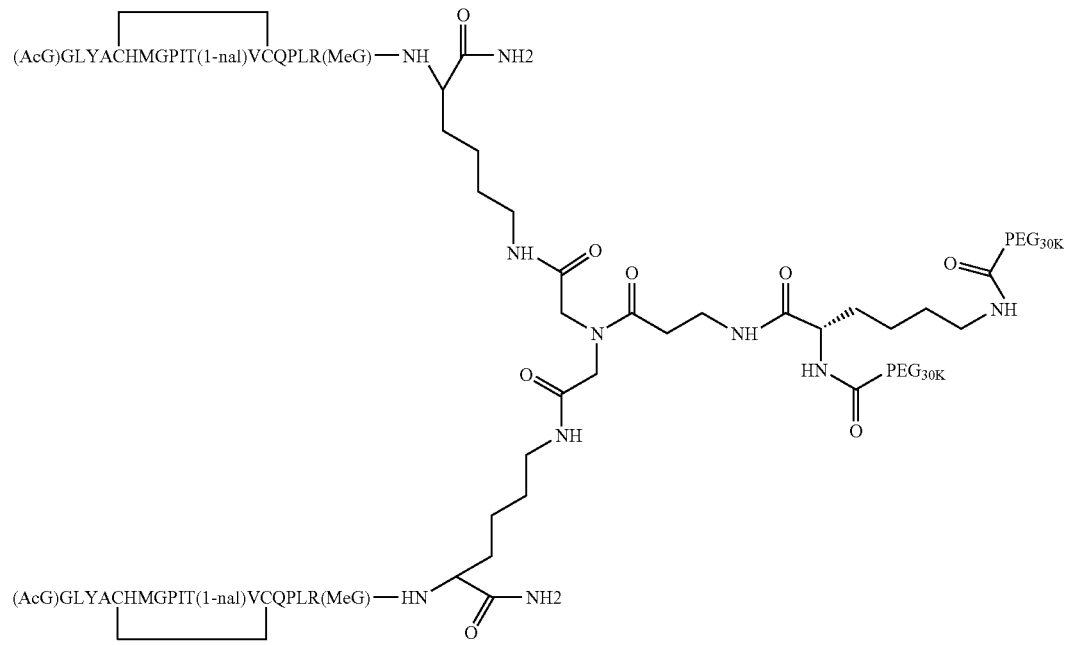
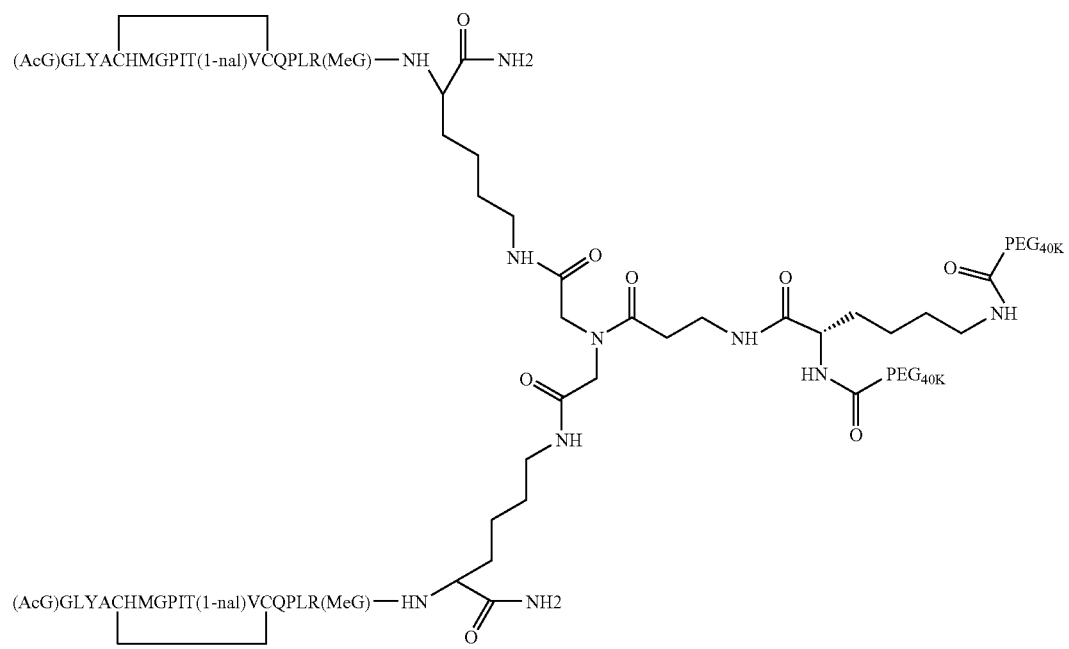

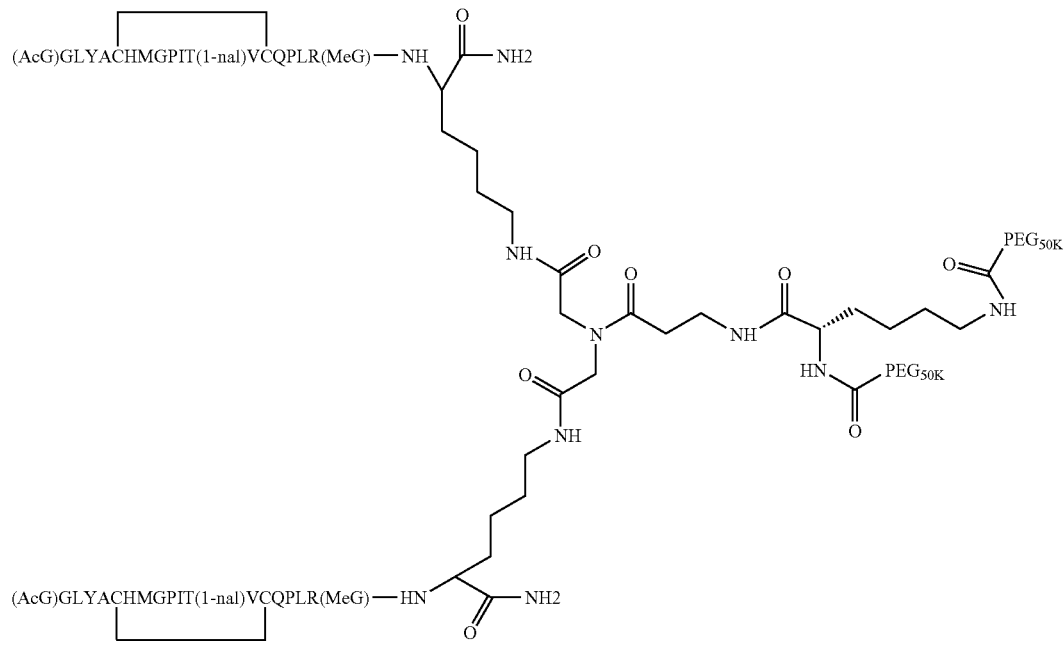

Where the spacer is attached via a carbamate linkage to an activated polyethylene glycol (PEG) moiety, the novel peptide compounds of the invention (SEQ ID NO: 3) may be represented as follows:

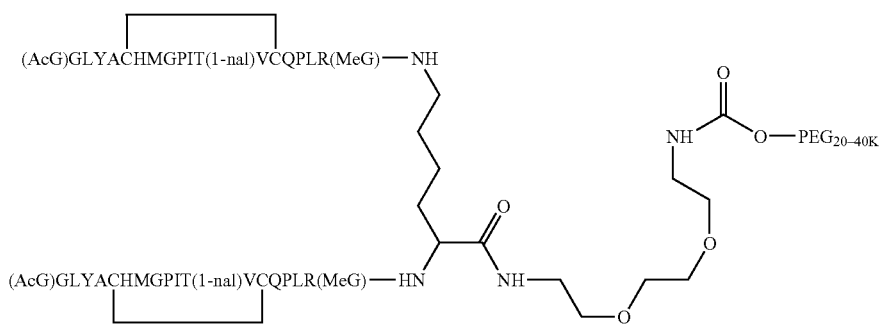

Where the spacer is attached via an amide linkage to an activated polyethylene glycol (PEG) moiety, the novel peptide compounds of the invention (SEQ ID NO: 3) may be represented as follows:

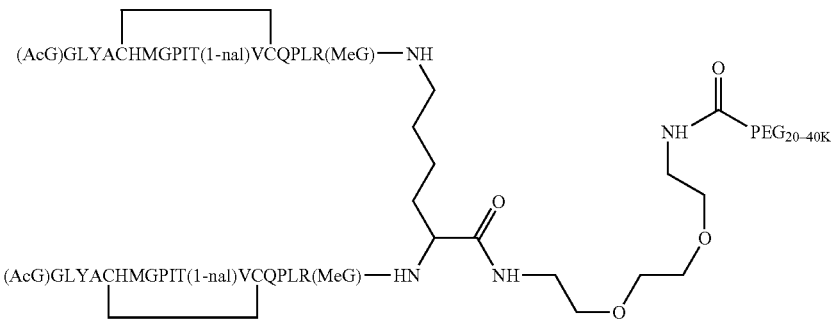

This dimeric structure can be written [Ac-peptide, disulfide]$_2$Lys-spacer-PEG$_{20-40K}$ to denote an N-terminally acetylated peptide bound to both the α and ε amino groups of lysine with each peptide containing an intramolecular disulfide loop and a spacer molecule forming a covalent linkage between the C-terminus of lysine and a PEG moiety, where the PEG has a molecular weight of about 20,000 to about 40,000 Daltons.

Preferred peptide dimers of the present invention include, but are not limited to:

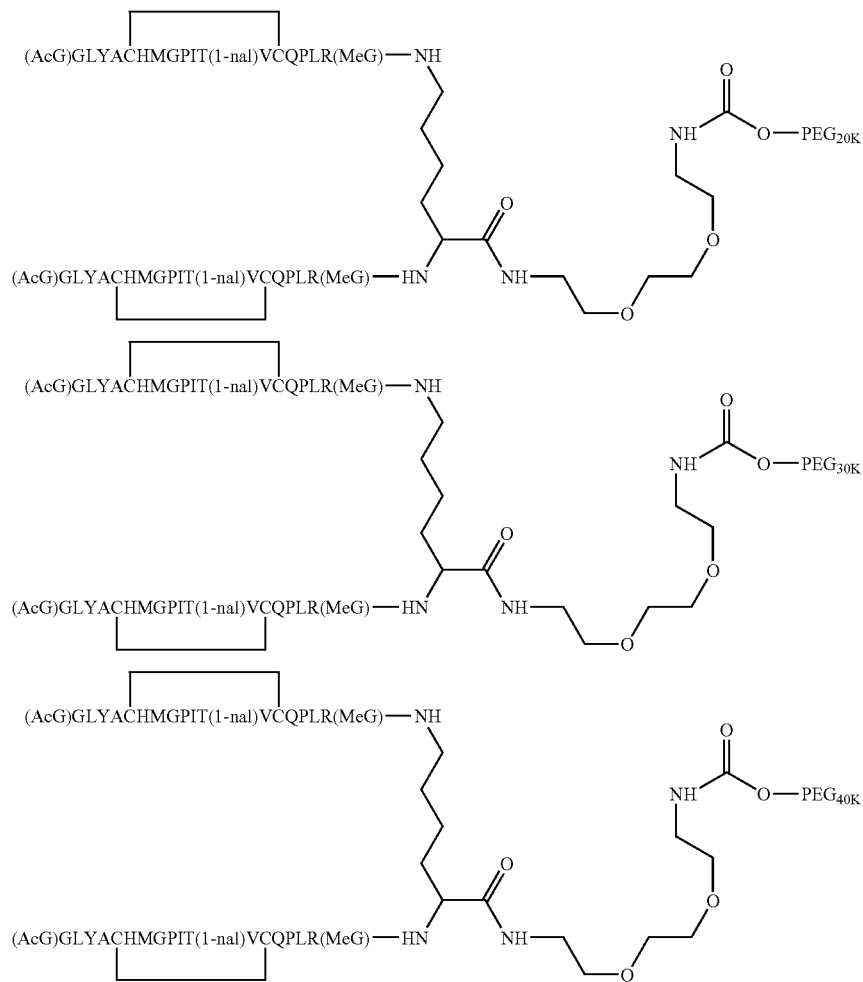

-continued (AcG)GLYACHMGPIT(1-nal)VCQPLR(MeG)—NH—[structure with Lys branching to PEG$_{20K}$ via carbamate-ethoxyethyl linker]
(AcG)GLYACHMGPIT(1-nal)VCQPLR(MeG)—HN (AcG)GLYACHMGPIT(1-nal)VCQPLR(MeG)—NH—[structure with Lys branching to PEG$_{30K}$ via carbamate-ethoxyethyl linker]
(AcG)GLYACHMGPIT(1-nal)VCQPLR(MeG)—HN (AcG)GLYACHMGPIT(1-nal)VCQPLR(MeG)—NH—[structure with Lys branching to PEG$_{40K}$ via carbamate-ethoxyethyl linker]
(AcG)GLYACHMGPIT(1-nal)VCQPLR(MeG)—HN Stereoisomers (e.g., D-amino acids) of the twenty conventional amino acids, unnatural amino acids such as a,a-disubstituted amino acids, N-alkyl amino acids, lactic acid, and other unconventional amino acids may also be suitable components for compounds of the present invention. Examples of unconventional amino acids include, but are not limited to: β-alanine, 3-pyridylalanine, 4-hydroxyproline, O-phosphoserine, N-methylglycine, N-acetylserine, N-formylmethionine, 3-methylhistidine, 5-hydroxylysine, nor-leucine, and other similar amino acids and imino acids. Other modifications are also possible, including modification of the amino terminus, modification of the carboxy terminus, replacement of one or more of the naturally occurring genetically encoded amino acids with an unconventional amino acid, modification of the side chain of one or more amino acid residues, peptide phosporylation, and the like.

The peptide sequences of the present invention and be present alone or in conjunction with N-terminal and/or C-terminal extensions of the peptide chain. Such extensions may be naturally encoded peptide sequences optionally with or substantially without non-naturally occurring sequences; the extensions may include any additions, deletions, point mutations, or other sequence modifications or combinations as desired by those skilled in the art. For example and not limitation, naturally-occurring sequences may be full-length or partial length and may include amino acid substitutions to provide a site for attachment of carbohydrate, PEG, other polymer, or the like via side chain conjugation. In a variation, the amino acid substitution results in humanization of a sequence to make in compatible with the human immune system. Fusion proteins of all types are provided, including immunoglobulin sequences adjacent to or in near proximity to the EPO-R activating sequences of the present invention with or without a non-immunoglobulin spacer sequence. One type of embodiment is an immunoglobulin chain having the EPO-R activating sequence in place of the variable (V) region of the heavy and/or light chain.

Preparation of the Peptide Compounds of the Invention:

Peptide Synthesis

The peptides of the invention may be prepared by classical methods known in the art. These standard methods include exclusive solid phase synthesis, partial solid phase synthesis methods, fragment condensation, classical solution synthesis, and recombinant DNA technology [See, e.g., Merrifield J. Am. Chem. Soc. 1963 85:2149].

In one embodiment, the peptide monomers of a peptide dimer are synthesized individually and dimerized subsequent to synthesis.

In another embodiment, the peptide monomers of a dimer are linked via their C-termini by a branched tertiary amide linker $L_K$ moiety having two functional groups capable of serving as initiation sites for peptide synthesis and a third functional group (e.g., a carboxyl group or an amino group) that enables binding to another molecular moiety (e.g., as may be present on the surface of a solid support). In this case, the two peptide monomers may be synthesized directly onto two reactive nitrogen groups of the linker $L_K$ moiety in a variation of the solid phase synthesis technique. Such synthesis may be sequential or simultaneous.

In another embodiment, the two peptide monomers may be synthesized directly onto two reactive nitrogen groups of the linker $L_K$ moiety in a variation of the solid phase synthesis technique. Such synthesis may be sequential or simultaneous. In this embodiment, a lysine linker ($L_K$) moiety having two amino groups capable of serving as initiation sites for peptide synthesis and a third functional group (e.g., the carboxyl group of a lysine; or the amino group of a lysine amide, a lysine residue wherein the carboxyl group has been converted to an amide moiety —$CONH_2$) that enables binding to another molecular moiety (e.g., as may be present on the surface of a solid support) is used.

Where sequential synthesis of the peptide chains of a dimer onto a linker is to be performed, two amine functional groups on the linker molecule are protected with two different orthogonally removable amine protecting groups. The protected linker is coupled to a solid support via the linker's third functional group. The first amine protecting group is removed, and the first peptide of the dimer is synthesized on the first deprotected amine moiety. Then the second amine protecting group is removed, and the second peptide of the dimer is synthesized on the second deprotected amine moiety. For example, the first amino moiety of the linker may be protected with Alloc, and the second with Fmoc. In this case, the Fmoc group (but not the Alloc group) may be removed by treatment with a mild base [e.g., 20% piperidine in dimethyl formamide (DMF)], and the first peptide chain synthesized. Thereafter the Alloc group may be removed with a suitable reagent [e.g., $Pd(PPh_3)$/4-methyl morpholine and chloroform], and the second peptide chain synthesized. Note that where different thiol-protecting groups for cysteine are to be used to control disulfide bond formation (as discussed below) this technique must be used even where the final amino acid sequences of the peptide chains of a dimer are identical.

Where simultaneous synthesis of the peptide chains of a dimer onto a linker is to be performed, two amine functional groups of the linker molecule are protected with the same removable amine protecting group. The protected linker is coupled to a solid support via the linker's third functional group. In this case the two protected functional groups of the linker molecule are simultaneously deprotected, and the two peptide chains simultaneously synthesized on the deprotected amines. Note that using this technique, the sequences of the peptide chains of the dimer will be identical, and the thiol-protecting groups for the cysteine residues are all the same.

A preferred method for peptide synthesis is solid phase synthesis. Solid phase peptide synthesis procedures are well-known in the art [see, e.g., Stewart *Solid Phase Peptide Syntheses* (Freeman and Co.: San Francisco) 1969; 2002/2003 General Catalog from Novabiochem Corp, San Diego, USA; Goodman *Synthesis of Peptides and Peptidomimetics* (Houben-Weyl, Stuttgart) 2002]. In solid phase synthesis, synthesis is typically commenced from the C-terminal end of the peptide using an α-amino protected resin. A suitable starting material can be prepared, for instance, by attaching the required α-amino acid to a chloromethylated resin, a hydroxymethyl resin, a polystyrene resin, a benzhydrylamine resin, or the like. One such chloromethylated resin is sold under the trade name BIO-BEADS SX-1 by Bio Rad Laboratories (Richmond, Calif.). The preparation of the hydroxymethyl resin has been described [Bodonszky, et al. (1966) Chem. Ind. London 38:1597]. The benzhydrylamine (BHA) resin has been described [Pietta and Marshall (1970) Chem. Commun. 650], and the hydrochloride form is commercially available from Beckman Instruments, Inc. (Palo Alto, Calif.). For example, an α-amino protected amino acid may be coupled to a chloromethylated resin with the aid of a cesium bicarbonate catalyst, according to the method described by Gisin (1973) Helv. Chim. Acta 56:1467.

After initial coupling, the α-amino protecting group is removed, for example, using trifluoroacetic acid (TFA) or hydrochloric acid (HCl) solutions in organic solvents at room temperature. Thereafter, α-amino protected amino acids are successively coupled to a growing support-bound peptide chain. The α-amino protecting groups are those known to be useful in the art of stepwise synthesis of peptides, including: acyl-type protecting groups (e.g., formyl, trifluoroacetyl, acetyl), aromatic urethane-type protecting groups [e.g., benzyloxycarboyl (Cbz) and substituted Cbz], aliphatic urethane protecting groups [e.g., t-butyloxycarbonyl (Boc), isopropyloxycarbonyl, cyclohexyloxycarbonyl], and alkyl type protecting groups (e.g., benzyl, triphenylmethyl), fluorenylmethyl oxycarbonyl (Fmoc), allyloxycarbonyl (Alloc), and 1-(4,4-dimethyl-2,6-dioxocyclohex-1-ylidene)ethyl (Dde).

The side chain protecting groups (typically ethers, esters, trityl, PMC, and the like) remain intact during coupling and is not split off during the deprotection of the amino-terminus protecting group or during coupling. The side chain protecting group must be removable upon the completion of the synthesis of the final peptide and under reaction conditions that will not alter the target peptide. The side chain protecting groups for Tyr include tetrahydropyranyl, tert-butyl, trityl, benzyl, Cbz, Z-Br-Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting groups for Arg include nitro, Tosyl (Tos), Cbz, adamantyloxycarbonyl mesitoylsulfonyl (Mts), 2,2,4,6,7-pentamethyldihydrobenzofurane-5-sulfonyl (Pbf), 4-mthoxy-2,3,6-trimethyl-benzenesulfonyl (Mtr), or Boc. The side chain protecting groups for Lys include Cbz, 2-chlorobenzyloxycarbonyl (2-Cl-Cbz), 2-bromobenzyloxycarbonyl (2-Br-Cbz), Tos, or Boc.

After removal of the α-amino protecting group, the remaining protected amino acids are coupled stepwise in the desired order. Each protected amino acid is generally reacted in about a 3-fold excess using an appropriate carboxyl group activator such as 2-(1H-benzotriazol-1-yl)-1,1,3,3 tetramethyluronium hexafluorophosphate (HBTU) or dicyclohexylcarbodiimide (DCC) in solution, for example, in methylene chloride ($CH_2Cl_2$), N-methylpyrrolidone, dimethyl formamide (DMF), or mixtures thereof.

After the desired amino acid sequence has been completed, the desired peptide is decoupled from the resin support by treatment with a reagent, such as trifluoroacetic acid (TFA) or hydrogen fluoride (HF), which not only cleaves the peptide from the resin, but also cleaves all remaining side chain protecting groups. When a chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

In preparing the esters of the invention, the resins used to prepare the peptide acids are employed, and the side chain protected peptide is cleaved with base and the appropriate alcohol (e.g., methanol). Side chain protecting groups are then removed in the usual fashion by treatment with hydrogen fluoride to obtain the desired ester.

These procedures can also be used to synthesize peptides in which amino acids other than the 20 naturally occurring, genetically encoded amino acids are substituted at one, two, or more positions of any of the compounds of the invention. Synthetic amino acids that can be substituted into the peptides of the present invention include, but are not limited to, N-methyl, L-hydroxypropyl, L-3, 4-dihydroxyphenylalanyl, δ amino acids such as L-δ-hydroxylysyl and D-δ-methylalanyl, L-α-methylalanyl, β amino acids, and isoquinolyl. D-amino acids and non-naturally occurring synthetic amino acids can also be incorporated into the peptides of the present invention.

Peptide Modifications

One can also modify the amino and/or carboxy termini of the peptide compounds of the invention to produce other compounds of the invention. For example, the amino terminus may be acetylated with acetic acid or a halogenated derivative thereof such as α-chloroacetic acid, α-bromoacetic acid, or α-iodoacetic acid).

One can replace the naturally occurring side chains of the 20 genetically encoded amino acids (or the stereoisomeric D amino acids) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered heterocyclic. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify peptides by phosphorylation, and other methods [e.g., as described in Hruby, et al. (1990) Biochem J. 268:249–262].

The peptide compounds of the invention also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis [See, Morgan and Gainor (1989) Ann. Rep. Med. Chem. 24:243–252]. These techniques include replacing the peptide backbone with a backbone composed of phosphonates, amidates, carbamates, sulfonamides, secondary amines, and N-methylamino acids.

Formation of Disulfide Bonds

The compounds of the present invention contain two intramolecular disulfide bonds. Such disulfide bonds may be formed by oxidation of the cysteine residues of each peptide monomer.

In one embodiment, the control of cysteine bond formation is exercised by choosing an oxidizing agent of the type and concentration effective to optimize formation of the desired isomer. For example, oxidation of a peptide dimer to form two intramolecular disulfide bonds (one on each peptide chain) is preferentially achieved (over formation of intermolecular disulfide bonds) when the oxidizing agent is DMSO or iodine ($I_2$).

In other embodiments, the formation of cysteine bonds is controlled by the selective use of thiol-protecting groups during peptide synthesis. For example, where a dimer with two intramolecular disulfide bonds is desired, the first monomer peptide chain is synthesized with the two cysteine residues of the core sequence protected with a first thiol protecting group [e.g., trityl(Trt), allyloxycarbonyl (Alloc), and 1-(4,4-dimethyl-2,6-dioxocyclohex-1-ylidene)ethyl (Dde)or the like], then the second monomer peptide is synthesized the two cysteine residues of the core sequence protected with a second thiol protecting group different from the first thiol protecting group [e.g., acetamidomethyl (Acm), t-butyl (tBu), or the like]. Thereafter, the first thiol protecting groups are removed effecting bisulfide cyclization of the first monomer, and then the second thiol protecting groups are removed effecting bisulfide cyclization of the second monomer.

Other embodiments of this invention provide for analogues of these disulfide derivatives in which one of the sulfurs has been replaced by a $CH_2$ group or other isotere for sulfur. These analogues can be prepared from the compounds of the present invention, wherein each peptide monomer contains at least one C or homocysteine residue and an α-amino-γ-butyric acid in place of the second C residue, via an intramolecular or intermolecular displacement, using methods known in the art [See, e.g., Barker, et al. (1992) J. Med. Chem. 35:2040–2048 and Or, et al. (1991) J. Org. Chem. 56:3146–3149]. One of skill in the art will readily appreciate that this displacement can also occur using other homologs of α-amino-γ-butyric acid and homocysteine.

In addition to the foregoing cyclization strategies, other non-disulfide peptide cyclization strategies can be employed. Such alternative cyclization strategies include, for example, amide-cyclization strategies as well as those involving the formation of thio-ether bonds. Thus, the compounds of the present invention can exist in a cyclized form with either an intramolecular amide bond or an intramolecular thio-ether bond. For example, a peptide may be synthesized wherein one cysteine of the core sequence is replaced with lysine and the second cysteine is replaced with glutamic acid. Thereafter a cyclic monomer may be formed through an amide bond between the side chains of these two residues. Alternatively, a peptide may be synthesized wherein one cysteine of the core sequence is replaced with lysine (or serine). A cyclic monomer may then be formed through a thio-ether linkage between the side chains of the lysine (or serine) residue and the second cysteine residue of the core sequence. As such, in addition to disulfide cyclization strategies, amide-cyclization strategies and thio-ether cyclization strategies can both be readily used to cyclize the compounds of the present invention. Alternatively, the amino-terminus of the peptide can be capped with an α-substituted acetic acid, wherein the α-substituent is a leaving group, such as an α-haloacetic acid, for example, α-chloroacetic acid, α-bromoacetic acid, or α-iodoacetic acid.

Addition of Branched Tertiary Amide Linker

The peptide monomers may be dimerized by a branched tertiary amide linker moeity. In one embodiment, the linker is incorporated into the peptide during peptide synthesis. For example, where a linker $L_K$ moiety contains two functional groups capable of serving as initiation sites for peptide synthesis and one or more other functional groups (e.g., a carboxyl group or an amino group) that enables binding to one or more other molecular moieties, the linker may be conjugated to a solid support. Thereafter, two peptide monomers may be synthesized directly onto the two reactive nitrogen groups of the linker $L_K$ moiety in a variation of the solid phase synthesis technique.

In alternate embodiments, the linker may be conjugated to the two peptide monomers of a peptide dimer after peptide synthesis. Such conjugation may be achieved by methods well established in the art. In one embodiment, the linker contains two functional groups suitable for attachment to the target functional groups of the synthesized peptide monomers. For example, a linker containing two carboxyl groups, either preactivated or in the presence of a suitable coupling reagent, may be reacted with the target lysine side chain amine groups of each of two peptide monomers.

For example, the peptide momomers may be chemically coupled to the tertiary amide linker,

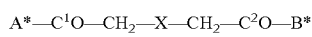

where: X is NCO—(CH$_2$)$_2$—NH—Y and Y is a suitable protecting group, such as a t-butyloxycarbonyl (Boc) protecting group; A* is a suitable functional group, such as N-oxy succinimide, used to conjugate $C^1$ of the linker to the ε-amino group of the C-terminal lysine residue of the first peptide monomer; and B* is a suitable functional group, such as N-oxy succinimide, used to conjugate $C^2$ of the linker to the ε-amino group of the C-terminal lysine residue of the second peptide monomer.

Additionally, for example, the peptide monomers may be chemically coupled to the tertiary amide linker,

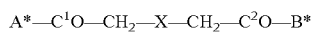

where: X is NCO—(CH$_2$)$_2$—NH—C$^3$O—; A* is a suitable functional group, such as N-oxy succinimide, used to conjugate $C^1$ of the linker to the ε-amino group of the C-terminal lysine residue of the first peptide monomer; and B* is a suitable functional group, such as N-oxy succinimide, used to conjugate $C^2$ of the linker to the ε-amino group of the C-terminal lysine residue of the second peptide monomer; and the tertiary amide linker is chemically bonded to the spacer moiety,

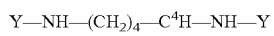

where: $C^3$ of X is covalently bonded to $C^4$ of the spacer; and Y is a suitable protecting group, such as a t-butyloxycarbonyl (Boc) protecting group.

Addition of Lysine Linker

The peptide monomers may be dimerized by a lysine linker $L_K$ moiety. In one embodiment, the lysine linker in incorporated into the peptide during peptide synthesis. For example, where a lysine linker $L_K$ moiety contains two functional groups capable of serving as initiation sites for peptide synthesis and a third functional group (e.g., a carboxyl group or an amino group) that enables binding to another molecular moiety, the linker may be conjugated to a solid support. Thereafter, two peptide monomers may be synthesized directly onto the two reactive nitrogen groups of the lysine linker $L_K$ moiety in a variation of the solid phase synthesis technique.

In alternate embodiments where a peptide dimer is dimerized by a lysine linker $L_K$ moiety, said linker may be conjugated to the two peptide monomers of a peptide dimer after peptide synthesis. Such conjugation may be achieved by methods well established in the art. In one embodiment, the linker contains at least two functional groups suitable for attachment to the target functional groups of the synthesized peptide monomers. For example, a the lysine's two free amine groups may be reacted with the C-terminal carboxyl groups of each of two peptide monomers.

Addition of Spacer

The peptide compounds of the invention further comprise a spacer moiety. In one embodiment the spacer may be incorporated into the peptide during peptide synthesis. For example, where a spacer contains a free amino group and a second functional group (e.g., a carboxyl group or an amino group) that enables binding to another molecular moiety, the spacer may be conjugated to the solid support.

In one embodiment, a spacer containing two functional groups is first coupled to the solid support via a first functional group. Next the lysine linker $L_K$ moiety having two functional groups capable of serving as initiation sites for peptide synthesis and a third functional group (e.g., a carboxyl group or an amino group) that enables binding to another molecular moiety is conjugated to the spacer via the spacer's second functional group and the linker's third functional group. Thereafter, two peptide monomers may be synthesized directly onto the two reactive nitrogen groups of the linker $L_K$ moiety in a variation of the solid phase synthesis technique. For example, a solid support coupled spacer with a free amine group may be reacted with a lysine linker via the linker's free carboxyl group.

In alternate embodiments the spacer may be conjugated to the peptide dimer after peptide synthesis. Such conjugation may be achieved by methods well established in the art. In one embodiment, the linker contains at least one functional group suitable for attachment to the target functional group of the synthesized peptide. For example, a spacer with a free amine group may be reacted with a peptide's C-terminal carboxyl group. In another example, a linker with a free carboxyl group may be reacted with the free amine group of a lysine amide.

Attachment of Polyethylene Glycol (PEG)

In recent years, water-soluble polymers, such as polyethylene glycol (PEG), have been used for the covalent modification of peptides of therapeutic and diagnostic importance. Attachment of such polymers is thought to enhance biological activity, prolong blood circulation time, reduce immunogenicity, increase aqueous solubility, and enhance resistance to protease digestion. For example, covalent attachment of PEG to therapeutic polypeptides such as interleukins [Knauf, et al. (1988) J. Biol. Chem. 263; 15064; Tsutsumi, et al. (1995) J. Controlled Release 33:447), interferons (Kita, et al. (1990) Drug Des. Delivery 6:157), catalase (Abuchowski, et al. (1977) J. Biol. Chem. 252:582), superoxide dismutase (Beauchamp, et al. (1983) Anal. Biochem. 131:25), and adenosine deaminase (Chen, et al. (1981) Biochim. Biophy. Acta 660:293), has been reported to extend their half life in vivo, and/or reduce their immunogenicity and antigenicity.

The peptide compounds of the invention may comprise a polyethylene glycol (PEG) moiety, which is covalently attached to the branched tertiary amide linker or the spacer of the peptide dimer via a carbamate linkage or via an amide linkage. An example of PEG used in the present invention is linear, unbranched PEG having a molecular weight of about 20 kiloDaltons (20K) to about 40K (the term "about" indicating that in preparations of PEG, some molecules will weigh more, some less, than the stated molecular weight). Preferably, the PEG has a molecular weight of about 30K to about 40K.

Another example of PEG used in the present invention is linear PEG having a molecular weight of about 10K to about 60K (the term "about" indicating that in preparations of PEG, some molecules will weigh more, some less, than the stated molecular weight). Preferably, the PEG has a molecular weight of about 20K to about 40K. More preferably, the PEG has a molecular weight of about 20K.

Examples of methods for covalent attachment of PEG (PEGylation) are described below. These illustrative descriptions are not intended to be limiting. One of ordinary skill in the art will appreciate that a variety of methods for covalent attachment of a broad range of PEG is well established in the art. As such, peptide compounds to which PEG has been attached by any of a number of attachment methods known in the art are encompassed by the present invention.

For example, PEG may be covalently bound to the linker via a reactive group to which an activated PEG molecule may be bound (e.g., a free amino group or carboxyl group). PEG molecules may be attached to amino groups using methoxylated PEG ("mPEG") having different reactive moieties. Such polymers include mPEG-succinimidyl succinate, mPEG-succinimidyl carbonate, mPEG-imidate, mPEG-4-nitrophenyl carbonate, and mPEG-cyanuric chloride. Similarly, PEG molecules may be attached to carboxyl groups using methoxylated PEG with a free amine group (mPEG-NH$_2$).

In some embodiments, the linker or spacer contains a terminal amino group (i.e., positioned at the terminus of the spacer). This terminal amino group may be reacted with a suitably activated PEG molecule, such as mPEG-para-nitrophenylcarbonate (mPEG-NPC), to make a stable covalent carbamate bond. Alternatively, this terminal amino group may be reacted with a suitably activated PEG molecule, such as an mPEG-succinimidyl butyrate (mPEG-SBA) or mPEG-succinimidyl propionate (mPEG-SPA) containing a reactive N-hydroxl-succinimide (NHS) group, to make a stable covalent carbamate bond. In other embodiments, the linker reactive group contains a carboxyl group capable of being activated to form a covalent bond with an amine-containing PEG molecule under suitable reaction conditions. Suitable PEG molecules include mPEG-NH$_2$ and suitable reaction conditions include carbodiimide-mediated amide formation or the like.

EPO-R Agonist Activity Assays:

In Vitro Functional Assays

In vitro competitive binding assays quantitate the ability of a test peptide to compete with EPO for binding to EPO-R. For example (see, e.g., as described in U.S. Pat. No. 5,773,569), the extracellular domain of the human EPO-R (EPO binding protein, EBP) may be recombinantly produced in *E. coli* and the recombinant protein coupled to a solid support, such as a microtitre dish or a synthetic bead [e.g., Sulfolink beads from Pierce Chemical Co. (Rockford, Ill.)]. Immobilized EBP is then incubated with labeled recombinant EPO, or with labeled recombinant EPO and a test peptide. Serial dilutions of test peptide are employed for such experiments. Assay points with no added test peptide define total EPO binding to EBP. For reactions containing test peptide, the amount of bound EPO is quantitated and expressed as a percentage of the control (total=100%) binding. These values are plotted versus peptide concentration. The IC50 value is defined as the concentration of test peptide which reduces the binding of EPO to EBP by 50% (i.e., 50% inhibition of EPO binding).

A different in vitro competitive binding assay measures the light signal generated as a function of the proximity of two beads: an EPO-conjugated bead and an EPO-R-conjugated bead. Bead proximity is generated by the binding of EPO to EPO-R. A test peptide that competes with EPO for binding to EPO-R will prevent this binding, causing a decrease in light emission. The concentration of test peptide that results in a 50% decrease in light emission is defined as the IC50 value.

The peptides of the present invention compete very efficiently with EPO for binding to the EPO-R. This enhanced function is represented by their ability to inhibit the binding of EPO at substantially lower concentrations of peptide (i.e., they have very low IC50 values).

The biological activity and potency of monomeric and dimeric peptide EPO-R agonists of the invention, which bind specifically to the EPO-receptor, may be measured using in vitro cell-based functional assays.

One assay is based upon a murine pre-B-cell line expressing human EPO-R and further transfected with a fos promoter-driven luciferase reporter gene construct. Upon exposure to EPO or another EPO-R agonist, such cells respond by synthesizing luciferase. Luciferase causes the emission of light upon addition of its substrate luciferin. Thus, the level of EPO-R activation in such cells may be quantitated via measurement of luciferase activity. The activity of a test peptide is measured by adding serial dilutions of the test peptide to the cells, which are then incubated for 4 hours. After incubation, luciferin substrate is added to the cells, and light emission is measured. The concentration of test peptide that results in a half-maximal emission of light is recorded as the EC50.

The peptides of the present invention show dramatically enhanced ability to promote EPO-R signaling-dependent luciferase expression in this assay. This enhanced function is represented by their ability to yield half of the maximal luciferase activity at substantially lower concentrations of peptide (i.e., they have very low EC50 values). This assay is a preferred method for estimating the potency and activity of an EPO-R agonist peptide of the invention.

Another assay may be performed using FDC-P1/ER cells [Dexter, et al. (1980) J. Exp. Med. 152:1036–1047], a well characterized nontransformed murine bone marrow derived cell line into which EPO-R has been stably transfected. These cells exhibit EPO-dependent proliferation.

In one such assay, the cells are grown to half stationary density in the presence of the necessary growth factors (see, e.g., as described in U.S. Pat. No. 5,773,569). The cells are then washed in PBS and starved for 16–24 hours in whole media without the growth factors. After determining the viability of the cells (e.g., by trypan blue staining), stock solutions (in whole media without the growth factors) are made to give about $10^5$ cells per 50 µL. Serial dilutions of the peptide EPO-R agonist compounds (typically the free, solution phase peptide as opposed to a phage-bound or other bound or immobilized peptide) to be tested are made in 96-well tissue culture plates for a final volume of 50 µL per well. Cells (50 µL) are added to each well and the cells are incubated 24–48 hours, at which point the negative controls should die or be quiescent. Cell proliferation is then measured by techniques known in the art, such as an MTT assay which measures $H^3$-thymidine incorporation as an indication of cell proliferation [see, Mosmann (1983) J. Immunol. Methods 65:55–63]. Peptides are evaluated on both the EPO-R-expressing cell line and a parental non-expressing cell line. The concentration of test peptide necessary to yield one half of the maximal cell proliferation is recorded as the EC50.

The peptides of the present invention show dramatically enhanced ability to promote EPO-dependent cell growth in this assay. This enhanced function is represented by their ability to yield half of the maximal cell proliferation stimulation activity at substantially lower concentrations of peptide (i.e., they have very low EC50 values). This assay is a preferred method for estimating the potency and activity of an EPO-R agonist peptide of the invention.

In another assay, the cells are grown to stationary phase in EPO-supplemented medium, collected, and then cultured for an additional 18 hr in medium without EPO. The cells are divided into three groups of equal cell density: one group with no added factor (negative control), a group with EPO (positive control), and an experimental group with the test peptide. The cultured cells are then collected at various time points, fixed, and stained with a DNA-binding fluorescent dye (e.g., propidium iodide or Hoechst dye, both available from Sigma). Fluorescence is then measured, for example, using a FACS Scan Flow cytometer. The percentage of cells in each phase of the cell cycle may then be determined, for example, using the SOBR model of CellFIT software (Becton Dickinson). Cells treated with EPO or an active peptide will show a greater proportion of cells in S phase (as determined by increased fluorescence as an indicator of increased DNA content) relative to the negative control group.

Similar assays may be performed using FDCP-1 [see, e.g., Dexter et al. (1980) J. Exp. Med. 152:1036–1047] or TF-1 [Kitamura, et al. (1989) Blood 73:375–380] cell lines. FDCP-1 is a growth factor dependent murine multi-potential primitive hematopoietic progenitor cell line that can proliferate, but not differentiate, when supplemented with WEHI-3-conditioned media (a medium that contains IL-3, ATCC number TIB-68). For such experiments, the FDCP-1 cell line is transfected with the human or murine EPO-R to produce FDCP-1-hEPO-R or FDCP-1-mEPO-R cell lines, respectively, that can proliferate, but not differentiate, in the presence of EPO. TF-1, an EPO-dependent cell line, may also be used to measure the effects of peptide EPO-R agonists on cellular proliferation.

In yet another assay, the procedure set forth in Krystal (1983) Exp. Hematol 11:649–660 for a microassay based on $H^3$-thymidine incorporation into spleen cells may be employed to ascertain the ability of the compounds of the present invention to serve as EPO agonists. In brief, $B6C3F_1$ mice are injected daily for two days with phenylhydrazine (60 mg/kg). On the third day, spleen cells are removed and their ability to proliferate over a 24 hour period ascertained using an MTT assay.

The binding of EPO to EPO-R in an erythropoietin-responsive cell line induces tyrosine phosphorylation of both the receptor and numerous intracellular proteins, including Shc, vav and JAK2 kinase. Therefore, another in vitro assay measures the ability of peptides of the invention to induce tyrosine phosphorylation of EPO-R and downstream intracellular signal transducer proteins. Active peptides, as identified by binding and proliferation assays described above, elicit a phosphorylation pattern nearly identical to that of EPO in erythropoietin-responsive cells. For this assay, FDC-P1/ER cells [Dexter, et al. (1980) J Exp Med 152:1036–47] are maintained in EPO-supplemented medium and grown to stationary phase. These cells are then cultured in medium without EPO for 24 hr. A defined number of such cells is then incubated with a test peptide for approximately 10 min at 37° C. A control sample of cells with EPO is also run with each assay. The treated cells are then collected by centrifugation, resuspended in SDS lysis buffer, and subjected to SDS polyacrylamide gel electrophoresis. The electrophoresed proteins in the gel are transferred to nitrocellulose, and the phosphotyrosine containing proteins on the blot visualized by standard immunological techniques. For example, the blot may be probed with an anti-phosphotyrosine antibody (e.g., mouse anti-phosphotyrosine IgG from Upstate Biotechnology, Inc.), washed, and then probed with a secondary antibody [e.g., peroxidase labeled goat anti-mouse IgG from Kirkegaard & Perry Laboratories, Inc. (Washington, D.C.)]. Thereafter, phosphotyrosine-containing proteins may be visualized by standard techniques including colorimetric, chemiluminescent, or fluorescent assays. For example, a chemiluminescent assay may be performed using the ECL Western Blotting System from Amersham.

Another cell-based in vitro assay that may be used to assess the activity of the peptides of the present invention is a colony assay, using murine bone marrow or human peripheral blood cells. Murine bone marrow may be obtained from the femurs of mice, while a sample of human peripheral blood may obtained from a healthy donor. In the case of peripheral blood, mononuclear cells are first isolated from the blood, for example, by centrifugation through a Ficoll-Hypaque gradient [Stem Cell Technologies, Inc. (Vancouver, Canada)]. For this assay a nucleated cell count is performed to establish the number and concentration of nucleated cells in the original sample. A defined number of cells is plated on methyl cellulose as per manufacturer's instructions [Stem Cell Technologies, Inc. (Vancouver, Canada)]. An experimental group is treated with a test peptide, a positive control group is treated with EPO, and a negative control group receives no treatment. The number of growing colonies for each group is then scored after defined periods of incubation, generally 10 days and 18 days. An active peptide will promote colony formation.

Other in vitro biological assays that can be used to demonstrate the activity of the compounds of the present invention are disclosed in Greenberger, et al. (1983) Proc. Natl. Acad. Sci. USA 80:2931–2935 (EPO-dependent hematopoietic progenitor cell line); Quelle and Wojchowski (1991) J. Biol. Chem. 266:609–614 (protein tyrosine phosphorylation in B6SUt.EP cells); Dusanter-Fourt, et al. (1992) J. Biol. Chem. 287:10670–10678 (tyrosine phosphorylation of EPO-receptor in human EPO-responsive cells); Quelle, et al. (1992) J. Biol. Chem. 267:17055–17060 (tyrosine phosphorylation of a cytosolic protein, pp 100, in FDC-ER cells); Worthington, et al. (1987) Exp. Hematol. 15:85–92 (colorimetric assay for hemoglobin); Kaiho and Miuno (1985) Anal. Biochem. 149:117–120 (detection of hemoglobin with 2,7-diaminofluorene); Patel, et al. (1992) J. Biol. Chem. 267:21300–21302 (expression of c-myb); Witthuhn, et al. (1993) Cell 74:227–236 (association and tyrosine phosphorylation of JAK2); Leonard, et al. (1993) Blood 82:1071–1079 (expression of GATA transcription factors); and Ando, et al. (1993) Proc. Natl. Acad. Sci. USA 90:9571–9575 (regulation of $G_1$ transition by cycling D2 and D3).

An instrument designed by Molecular Devices Corp., known as a microphysiometer, has been reported to be successfully used for measurement of the effect of agonists and antagonists on various receptors. The basis for this apparatus is the measurement of the alterations in the acidification rate of the extracellular media in response to receptor activation.

In Vivo Functional Assays

One in vivo functional assay that may be used to assess the potency of a test peptide is the polycythemic exhypoxic mouse bioassay. For this assay, mice are subjected to an alternating conditioning cycle for several days. In this cycle, the mice alternate between periods of hypobaric conditions and ambient pressure conditions. Thereafter, the mice are maintained at ambient pressure for 2–3 days prior to administration of test samples. Test peptide samples, or EPO standard in the case positive control mice, are injected subcutaneously into the conditioned mice. Radiolabeled iron (e.g., $Fe^{59}$) is administered 2 days later, and blood samples taken two days after administration of radiolabeled iron. Hematocrits and radioactivity measurements are then determined for each blood sample by standard techniques. Blood samples from mice injected with active test peptides will show greater radioactivity (due to binding of $Fe^{59}$ by erythrocyte hemoglobin) than mice that did not receive test peptides or EPO.

Another in vivo functional assay that may be used to assess the potency of a test peptide is the reticulocyte assay. For this assay, normal untreated mice are subcutaneously injected on three consecutive days with either EPO or test peptide. On the third day, the mice are also intraperitoneally injected with iron dextran. At day five, blood samples are collected from the mice. The percent (%) of reticulocytes in the blood is determined by thiazole orange staining and flow cytometer analysis (retic-count program). In addition, hematocrits are manually determined. The percent of corrected reticulocytes is determined using the following formula:

$$\% \ RETIC_{CORRECTED} = \% \ RETIC_{OBSERVED} \times (Hematocrit_{INDIVIDUAL}/Hematocrit_{NORMAL})$$

Active test compounds will show an increased % $RETIC_{CORRECTED}$ level relative to mice that did not receive test peptides or EPO.

Use of EPO-R Agonist Peptides of the Invention

The peptide compounds of the invention are useful in vitro as tools for understanding the biological role of EPO, including the evaluation of the many factors thought to influence, and be influenced by, the production of EPO and the binding of EPO to the EPO-R (e.g., the mechanism of EPO/EPO-R signal transduction/receptor activation). The present peptides are also useful in the development of other compounds that bind to the EPO-R, because the present compounds provide important structure-activity-relationship information that facilitate that development.

Moreover, based on their ability to bind to EPO-R, the peptides of the present invention can be used as reagents for detecting EPO-R on living cells; fixed cells; in biological fluids; in tissue homogenates; in purified, natural biological materials; etc. For example, by labeling such peptides, one can identify cells having EPO-R on their surfaces. In addition, based on their ability to bind EPO-R, the peptides of the present invention can be used in in situ staining, FACS (fluorescence-activated cell sorting) analysis, Western blotting, ELISA (enzymelinked immunosorbent assay), etc. In addition, based on their ability to bind to EPO-R, the peptides of the present invention can be used in receptor purification, or in purifying cells expressing EPO-R on the cell surface (or inside permeabilized cells).

The peptides of the invention can also be utilized as commercial reagents for various medical research and diagnostic purposes. Such uses can include but are not limited to: (1) use as a calibration standard for quantitating the activities of candidate EPO-R agonists in a variety of functional assays; (2) use as blocking reagents in random peptide screening, i.e., in looking for new families of EPO-R peptide ligands, the peptides can be used to block recovery of EPO peptides of the present invention; (3) use in co-crystallization with EPO-R, i.e., crystals of the peptides of the present invention bound to the EPO-R may be formed, enabling determination of receptor/peptide structure by X-ray crystallography; (4) use to measure the capacity of erythrocyte precursor cells induce globin synthesis and heme complex synthesis, and to increase the number of ferritin receptors, by initiating differentiation; (5) use to maintain the proliferation and growth of EPO-dependent cell lines, such as the FDCP-1-mEPO-R and the TF-1 cell lines; (6) use related to labeling the peptides of the invention with a radioactive chromophore; and (7) other research and diagnostic applications wherein the EPO-R is preferably activated or such activation is conveniently calibrated against a known quantity of an EPO-R agonist, and the like.

In yet another aspect of the present invention, methods of treatment and manufacture of a medicament are provided. The peptide compounds of the invention may be administered to warm blooded animals, including humans, to simulate the binding of EPO to the EPO-R in vivo. Thus, the present invention encompasses methods for therapeutic treatment of disorders associated with a deficiency of EPO, which methods comprise administering a peptide of the invention in amounts sufficient to stimulate the EPO-R and thus, alleviate the symptoms associated with a deficiency of EPO in vivo. For example, the peptides of this invention will find use in the treatment of renal insufficiency and/or end-stage renal failure/dialysis; anemia associated with AIDS; anemia associated with chronic inflammatory diseases (for example, rheumatoid arthritis and chronic bowel inflammation) and autoimmune disease; and for boosting the red blood count of a patient prior to surgery. Other disease states, disorders, and states of hematologic irregularity that may be treated by administration of the peptides of this invention include: beta-thalassemia; cystic fibrosis; pregnancy and menstrual disorders; early anemia of prematurity; spinal cord injury; space flight; acute blood loss; aging; stroke, ischemia (both CNS and cardiac); and various neoplastic disease states accompanied by abnormal erythropoiesis.

In other embodiments, the peptide compounds of the invention may be used for the treatment of disorders which are not characterized by low or deficient red blood cells, for example as a pretreatment prior to transfusions. In addition, administration of the compounds of this invention can result in a decrease in bleeding time and thus, will find use in the administration to patients prior to surgery or for indications wherein bleeding is expected to occur. In addition, the compounds of this invention will find use in the activation of megakaryoctes.

Since EPO has been shown to have a mitogenic and chemotactic effect on vascular endothelial cells as well as an effect on central cholinergic neurons [see, e.g., Amagnostou, et al. (1990) Proc. Natl. Acad. Sci. USA 87:5978–5982 and Konishi, et al. (1993) Brain Res. 609:29–35], the compounds of this invention will also find use for the treatment of a variety of vascular disorders, such as: promoting wound healing; promoting growth of collateral coronary blood vessels (such as those that may occur after myocardial infarction); trauma treatment; and post-vascular graft treatment. The compounds of this invention will also find use for the treatment of a variety of neurological disorders, generally characterized by low absolute levels of acetyl choline or low relative levels of acetyl choline as compared to other neuroactive substances e.g., neurotransmitters.

Pharmaceutical Compositions

In yet another aspect of the present invention, pharmaceutical compositions of the above EPO-R agonist peptide compounds are provided. Conditions alleviated or modulated by the administration of such compositions include those indicated above. Such pharmaceutical compositions may be for administration by oral, parenteral (intramuscular, intraperitoneal, intravenous (IV) or subcutaneous injection), transdermal (either passively or using iontophoresis or electroporation), transmucosal (nasal, vaginal, rectal, or sublingual) routes of administration or using bioerodible inserts and can be formulated in dosage forms appropriate for each route of administration. In general, comprehended by the invention are pharmaceutical compositions comprising effective amounts of an EPO-R agonist peptide, or derivative products, of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 20, Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435–1712 which are herein incorporated by reference. The compositions may be prepared in liquid form, or may be in dried powder (e.g., lyophilized) form.

Oral Delivery

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include the EPO-R agonist peptides (or chemically modified forms thereof) and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

The peptides may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. As discussed above, PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in *Enzymes as Drugs*. Hocenberg and Roberts, eds. (Wiley-Interscience: New York, N.Y.) pp. 367–383; and Newmark, et al. (1982) J. Appl. Biochem. 4:185–189].

For oral formulations, the location of release may be the stomach, the small intestine (the duodenum, the jejunem, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the peptide (or derivative) or by release of the peptide (or derivative) beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e. powder), for liquid forms a soft gelatin shell may be used. The shell material of cachets could be thick starch or other edible paper. For pills, lozenges, molded tablets or tablet triturates, moist massing techniques can be used.

The peptide (or derivative) can be included in the formulation as fine multiparticulates in the form of granules or pellets of particle size about 1 mm. The formulation of the material for capsule administration could also be as a powder, lightly compressed plugs, or even as tablets. These therapeutics could be prepared by compression.

Colorants and/or flavoring agents may also be included. For example, the peptide (or derivative) may be formulated (such as by liposome or microsphere encapsulation) and then further contained within an edible product, such as a refrigerated beverage containing colorants and flavoring agents.

One may dilute or increase the volume of the peptide (or derivative) with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders. and can include powdered gums such as agar, Karaya or tragacanth. Alginic acid and its sodium salt are also useful as disintegrants.

Binders may be used to hold the peptide (or derivative) agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation of the peptide (or derivative) to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the peptide (or derivative) into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios.

Additives which potentially enhance uptake of the peptide (or derivative) are for instance the fatty acids oleic acid, linoleic acid and linolenic acid.

Controlled release oral formulations may be desirable. The peptide (or derivative) could be incorporated into an inert matrix which permits release by either diffusion or leaching mechanisms, e.g., gums. Slowly degenerating matrices may also be incorporated into the formulation. Some enteric coatings also have a delayed release effect. Another form of a controlled release is by a method based on the Oros therapeutic system (Alza Corp.), i.e. the drug is enclosed in a semipermeable membrane which allows water to enter and push drug out through a single small opening due to osmotic effects.

Other coatings may be used for the formulation. These include a variety of sugars which could be applied in a coating pan. The peptide (or derivative) could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid.

A mix of materials might be used to provide the optimum film coating. Film coating may be carried out in a pan coater or in a fluidized bed or by compression coating.

Parenteral Delivery

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Rectal or Vaginal Delivery

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

Pulmonary Delivery

Also contemplated herein is pulmonary delivery of the EPO-R agonist peptides (or derivatives thereof). The peptide (or derivative) is delivered to the lungs of a mammal while inhaling and traverses across the lung epithelial lining to the blood stream [see, e.g., Adjei, et al. (1990) Pharmaceutical Research 7:565–569; Adjei, et al. (1990) Int. J. Pharmaceutics 63:135–144 (leuprolide acetate); Braquet, et al. (1989) J. Cardiovascular Pharmacology 13(sup5):143–146 (endothelin-1); Hubbard, et al. (1989) Annals of Internal Medicine, Vol. III, pp. 206–212 (α1-antitrypsin); Smith, et al. (1989) J. Clin. Invest. 84:1145–1146 (α-1-proteinase); Oswein, et al. (1990) "Aerosolization of Proteins", Proceedings of Symposium on Respiratory Drug Delivery II Keystone, Colorado (recombinant human growth hormone); Debs, et al. (1988) J. Immunol. 140:3482–3488 (interferon-γ and tumor necrosis factor α); and U.S. Pat. No. 5,284,656 to Platz, et al. (granulocyte colony stimulating factor). A method and composition for pulmonary delivery of drugs for systemic effect is described in U.S. Pat. No. 5,451,569 to Wong, et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.).

All such devices require the use of formulations suitable for the dispensing of peptide (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified peptides may also be prepared in different formulations depending on the type of chemical modification or the type of device employed.

Formulations suitable for use with a nebulizer, either jet or ultrasonic, will typically comprise peptide (or derivative) dissolved in water at a concentration of about 0.1 to 25 mg of biologically active protein per mL of solution. The formulation may also include a buffer and a simple sugar (e.g., for protein stabilization and regulation of osmotic pressure). The nebulizer formulation may also contain a surfactant, to reduce or prevent surface induced aggregation of the peptide (or derivative) caused by atomization of the solution in forming the aerosol.

Formulations for use with a metered-dose inhaler device will generally comprise a finely divided powder containing the peptide (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing peptide (or derivative) and may also include a bulking agent, such as lactose, sorbitol, sucrose, or mannitol in amounts which facilitate dispersal of the powder from the device, e.g., 50 to 90% by weight of the formulation. The peptide (or derivative) should most advantageously be prepared in particulate form with an average particle size of less than 10 mm (or microns), most preferably 0.5 to 5 mm, for most effective delivery to the distal lung.

Nasal Delivery

Nasal delivery of the EPO-R agonist peptides (or derivatives) is also contemplated. Nasal delivery allows the passage of the peptide to the blood stream directly after administering the therapeutic product to the nose, without the necessity for deposition of the product in the lung. Formulations for nasal delivery include those with dextran or cyclodextran.

Dosages

For all of the peptide compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of 0.001 to 10 mg/kg of body weight daily are administered to mammals. Generally, for intravenous injection or infusion, dosage may be lower. The dosing schedule may vary, depending on the circulation half-life and the formulation used.

The peptides of the present invention (or their derivatives) may be administered in conjunction with one or more additional active ingredients or pharmaceutical compositions.

EXAMPLES

The present invention is next described by means of the following examples. However, the use of these and other examples anywhere in the specification is illustrative only, and in no way limits the scope and meaning of the invention or of any exemplified form. Likewise, the invention is not limited to any particular preferred embodiments described herein. Indeed, many modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

Example 1

Synthesis of EPO-R Agonist Peptide Dimers by Solid Phase Synthesis

Step 1—Synthesis of Cbz-TAP: A solution containing the commercially available diamine ("TAP" from Aldrich Chemical Co.) (10 g, 67.47 mmol) in anhydrous DCM (100 ml) was cooled to 0° C. A solution of benzyl chloroformate (4.82 ml, 33.7 mmol) in anhydrous DCM (50 ml) was added slowly through a dropping funnel over a period of 6–7 h, maintaining the temperature of the reaction mixture at 0° C. throughout, then allowed to warm to room temperature (~25° C.). After a further 16 h, the DCM was removed under vacuum and the residue partitioned between 3N HCl and ether. The aqueous layers were collected and neutralized with 50% aq. NaOH to pH 8–9 and extracted with ethyl acetate. The ethyl acetate layer was dried over anhydrous $Na_2SO_4$, then concentrated under vacuum to provide the crude mono-Cbz-TAP (5 g, about 50% yield). This compound was used for the next reaction without any further purification.

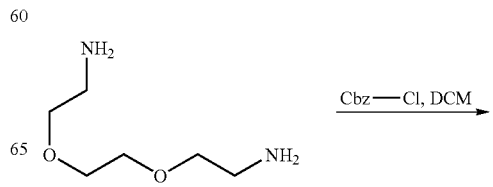

-continued

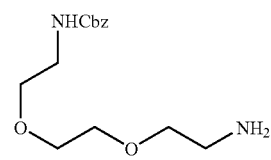

Step 2—Synthesis of Cbz-TAP-Boc: To a vigorously stirred suspension of the Cbz-TAP (5 g, 17.7 mmol) in hexane (25 ml) was added Boc$_2$O (3.86 g, 17.7 mmol) and stirring continued at RT overnight. The reaction mixture was diluted with DCM (25 ml) and washed with 10% aq. citric acid (2×), water (2×) and brine. The organic layer was dried over anhydrous Na$_2$SO$_4$ and concentrated under vacuum. The crude product (yield 5 g) was used directly in the next reaction.

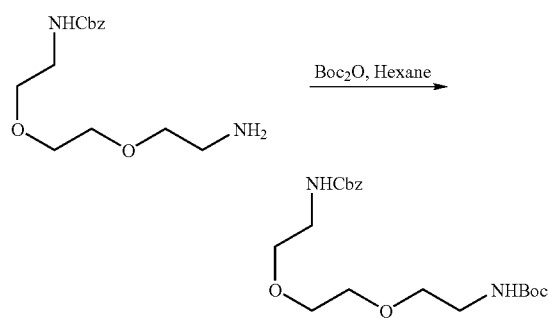

Step 3—Synthesis of Boc-TAP: The crude product from the previous reaction was dissolved in methanol (25 ml) and hydrogenated in presence of 5% Pd on Carbon (5% w/W) under balloon pressure for 16 hrs. The mixture was filtered, washed with methanol and the filtrate concentrated in vacuo to provide the crude H-TAP-Boc product (yield 3.7 g). The overall approximate yield of Boc-TAP after Steps 1–3 was 44% (calculated based on the amount of Cbz-Cl used.)

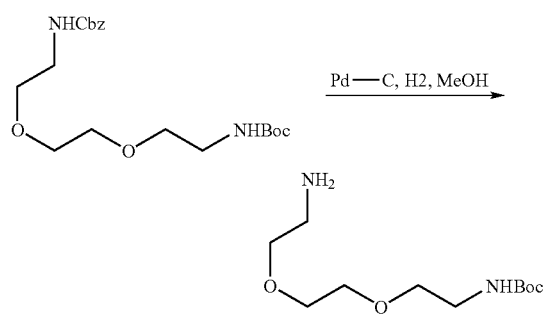

Step 4—Synthesis of TentaGel-Linker: TentaGel bromide (2.5 g, 0.48 mmol/g, from Rapp Polymere, Germany), phenolic linker (5 equivalent, and K$_2$CO$_3$ (5 equivalent) were heated in 20 mL of DMF to 70° C. for 14 h. After cooling to room temperature, the resin was washed (0.1 N HCl, water, ACN, DMF, MeOH) and dried to give an amber-colored resin.

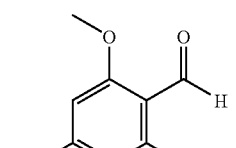

Step 5—Synthesis of TentaGel-linker-TAP(Boc): 2.5 gms of the resin from above and H-TAP-Boc (1.5 gms, 5 eq.) and glacial AcOH (34 µl, 5 eq.) was taken in a mixture of 1:1 MeOH-THF and shaken overnight. A 1M solution of sodium cyanoborohydride (5 eq) in THF was added to this and shaken for another 7 hrs. The resin was filtered washed (DMF, THF, 0.1 N HCl, water, MeOH) and dried. A small amount of the resin was benzoylated with Bz-Cl and DIEA in DCM and cleaved with 70% TFA-DCM and checked by LCMS and HPLC.

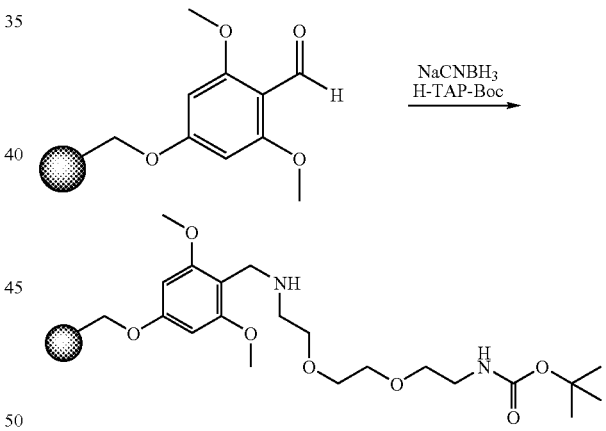

Step 6—Synthesis of TentaGel-linker-TAP-Lys: The resin from above was treated with a activated solution of Fmoc-Lys(Fmoc)-OH (prepared from 5 eq. of amino acid and 5 eq. of HATU dissolved at 0.5 M in DMF, followed by the addition of 10 eq. of DIEA) and allowed to gently shake 14 h. The resin was washed (DMF, THF, DCM, MeOH) and dried to yield the protected resin. Residual amine groups were capped by treating the resin with a solution of 10% acetic anhydride, 20% pyridine in DCM for 20 minutes, followed by washing as above. The Fmoc groups are removed by gently shaking the resin in 30% piperideine in DMF for 20 minutes, followed by washing (DMF, THF, DCM, MeOH) and drying.

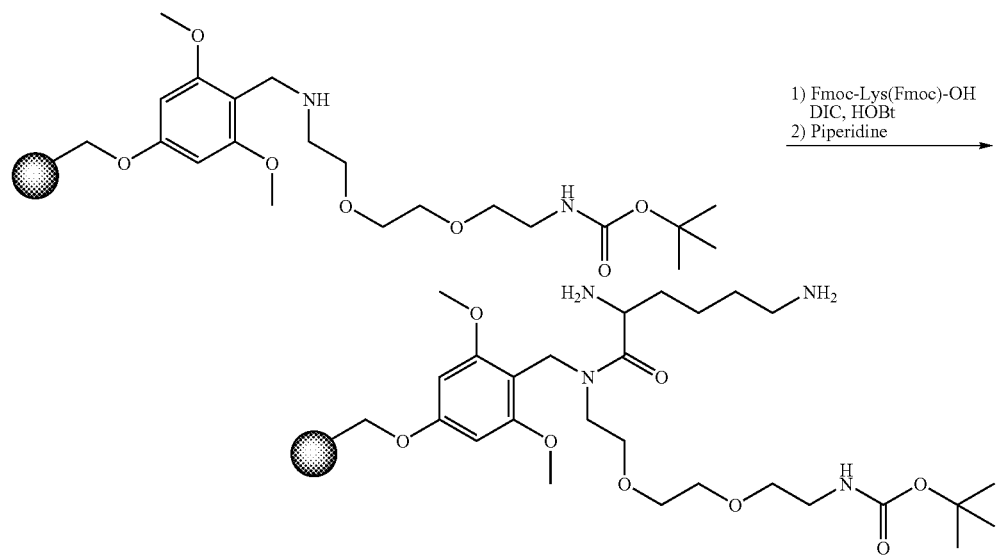

Step 7—Synthesis of TentaGel-Linker-TAP-Lys (Peptide)₂: The resin from above was subjected to repeated cycles of Fmoc-amino acid couplings with HBTU/HOBt activation and Fmoc removal with piperidine to build both peptide chains simultaneously. This was convenently carried out on a ABI 433 automated peptide synthesizer available from Applied Biosystems, Inc. After the final Fmoc removal, the terminal amine groups were acylated with acetic anhydride (10 eq.) and DIEA (20 eq.) in DMF for 20 minutes, follwed by washing as above.

Step 8—Cleavage from resin: The resin from above was suspended in a solution of TFA (82.5%), phenol (5%), ethanedithiol (2.5%), water (5%), and thioanisole (5%) for 3 h at room temperature. Alternative cleavage cocktails such as TFA (95%), water (2.5%), and triisopropylsilane (2.5%) can also be used. The TFA solution was cooled to 5° C. and poured into Et₂O to percipatate the peptide. Filtration and drying under reduced pressure gave the desired peptide. Purification via preparative HPLC with a C18 column afforded the pure peptide.

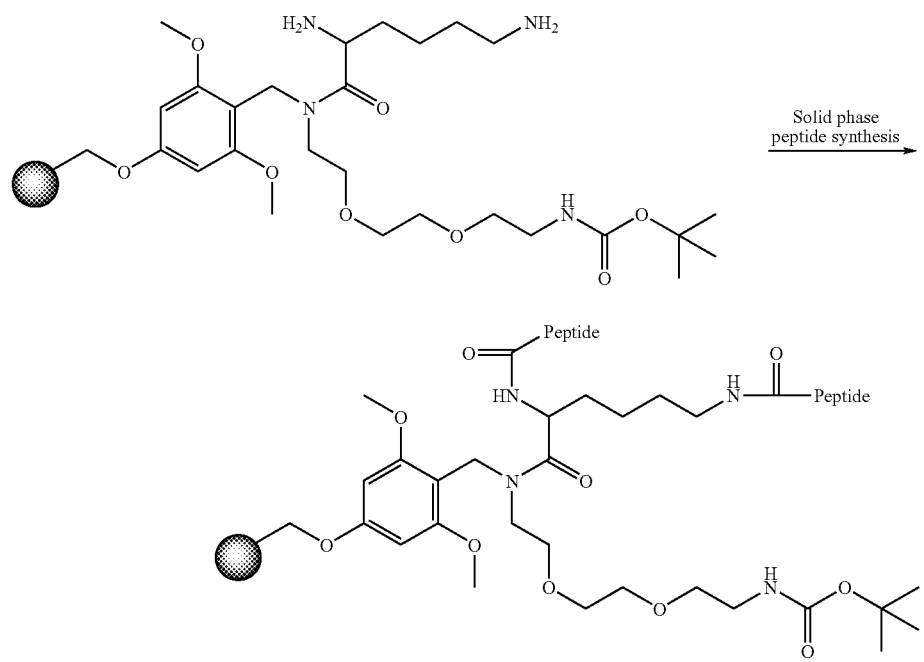

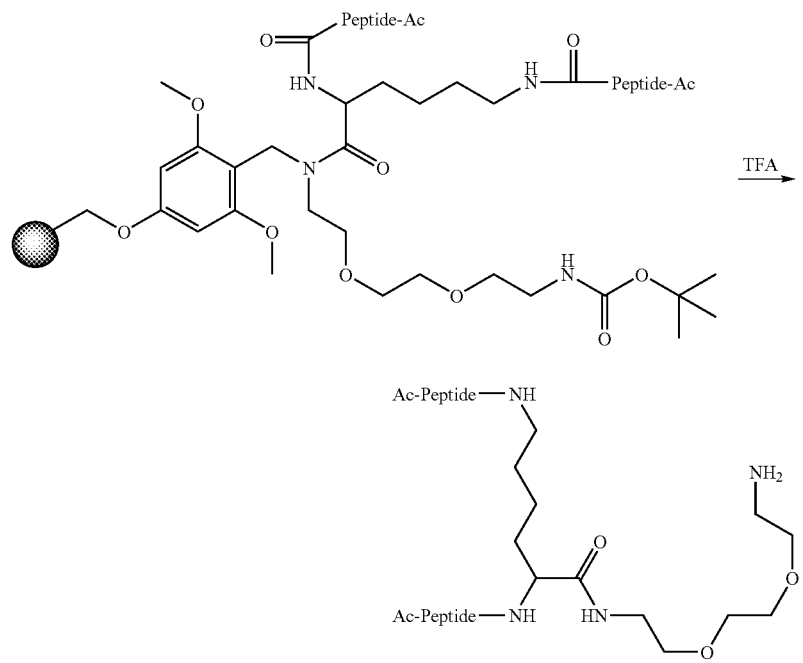

Step 9—Oxidation of peptides to form intramolecular disulfide bonds: The peptide dimer was dissolved in 20% DMSO/water (1 mg dry weight peptide/mL) and allowed to stand at room temperature for 36 h. The peptide was purified by loading the reaction mixture onto a C18 HPLC column (Waters Delta-Pak C18, 15 micron particle size, 300 angstrom pore size, 40 mm×200 mm length), followed by a linear ACN/water/0.01% TFA gradiant from 5 to 95% ACN over 40 minutes. Lyopholization of the fractions containing the desired peptide affords the product as a fluffy white solid.

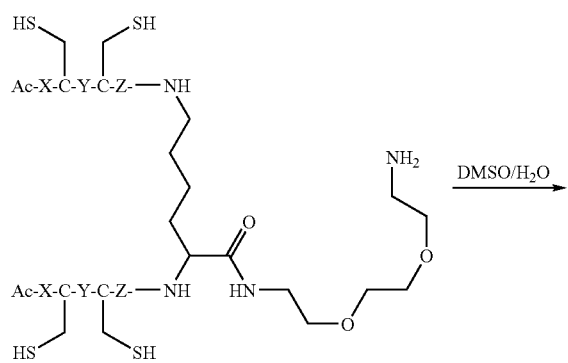

Dimeric peptide (XYZ) containing reduced cysteine residues

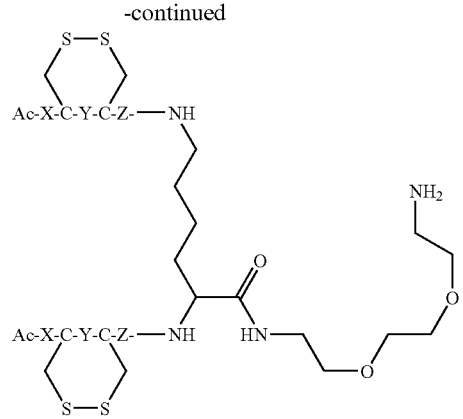

Dimeric peptide (XYZ) containing oxidized disulfide bonds

Step 10—PEGylation of the Terminal —NH$_2$ Group:

PEGylation via a carbamate bond: The peptide dimer was mixed with 1.5 eq. (mole basis) of activated PEG species (mPEG-NPC from NOF Corp. Japan) in dry DMF to afford a clear solution. After 5 minutes 4 eq of DIEA was added to above solution. The mixture was stirred at ambient temperature 14 h, followed by purification with C18 reverse phase HPLC. The structure of PEGylated peptide was confirmed by MALDI mass. The purified peptide was also subjected to purification via cation ion exchange chromatography as outlined below. The below scheme shows mPEG-NPC PEGylation using SEQ ID NO: 3.

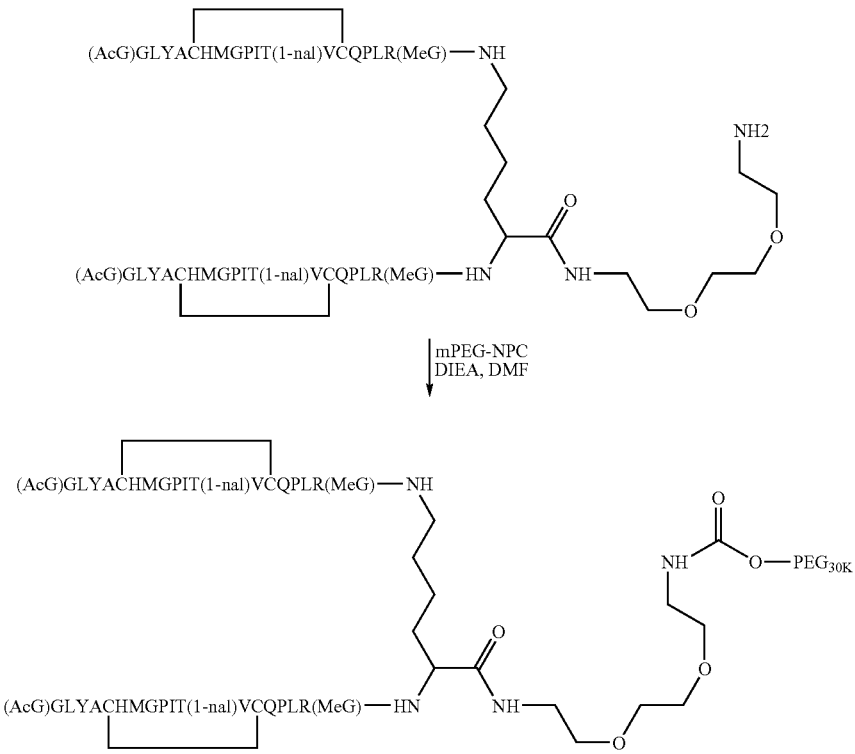

PEGylation via an amide bond: The peptide dimer is mixed with 1.5 eq. (mole basis) of 1 eq. activated PEG species (PEG-SPA-NHS from Shearwater Corp, USA) in dry DMF to afford a clear solution. After 5 minutes 10 eq of DIEA is added to above solution. The mixture is stirred at ambient temperature 2 h, followed by purification with C18 reverse phase HPLC. The structure of PEGylated peptide was confirmed by MALDI mass. The purified peptide was also subjected to purification via cation ion exchange chromatography as outlined below. The below scheme shows PEG-SPA-NHS PEGylation using SEQ ID NO: 3.

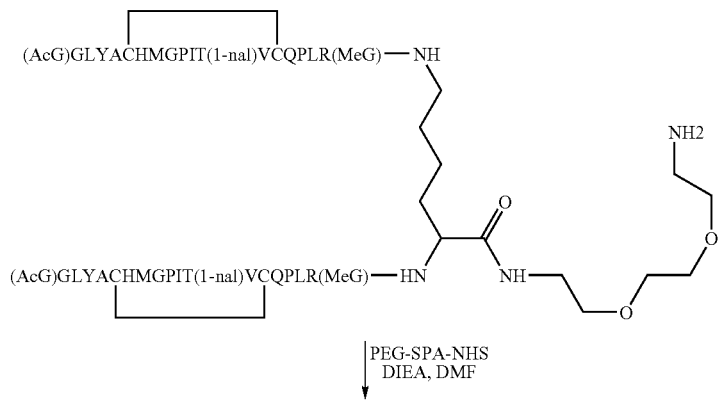

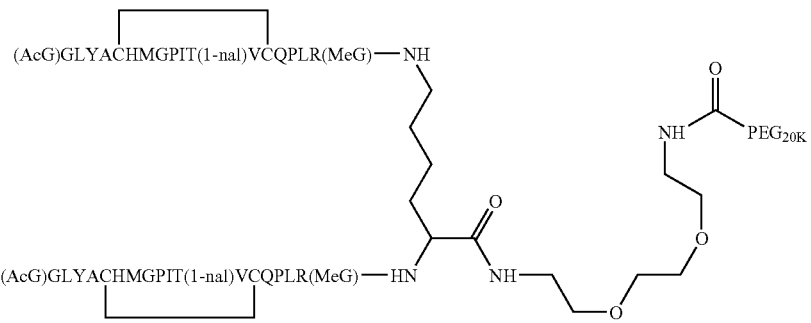

Step 11—Ion exchange purification: Several exchange supports were surveyed for their ability to separate the above peptide-PEG conjugate from unreacted (or hydrolyzed) PEG, in addition to their ability to retain the starting dimeric peptides. The ion exchange resin (2–3 g) was loaded into a 1 cm column, followed by conversion to the sodium form (0.2 N NaOH loaded onto column until elutant was pH 14, ca. 5 column volumes), and than to the hydrogen form (eluted with either 0.1 N HCl or 0.1 M HOAc until elutant matched load pH, ca. 5 column volumes), followed by washing with 25% ACN/water until pH 6. Either the peptide prior to conjugation or the peptide-PEG conjugate was dissolved in 25% ACN/water (10 mg/mL) and the pH adjusted to <3 with TFA, then loaded on the column. After washing with 2–3 column volumes of 25% ACN/water and collecting 5 mL fractions, the peptide was released from the column by elution with 0.1 M $NH_4OAc$ in 25% ACN/water, again collecting 5 mL fractions. Analysis via HPLC revealed which fractions contained the desired peptide. Analysis with an Evaporative Light-Scattering Detector (ELSD) indicated that when the peptide was retained on the column and was eluted with the $NH_4OAc$ solution (generally between fractions 4 and 10), no non-conjugated PEG was observed as a contaminant. When the peptide eluted in the initial wash buffer (generally the first 2 fractions), no separation of desired PEG-conjugate and excess PEG was observed.

The following columns successfully retained both the peptide and the peptide-PEG conjugate, and successfully purified the peptide-PEG conjugate from the unconjugates peptide:

TABLE 1

| Ion Exhange Resins | |
|---|---|
| Support | Source |
| Mono S HR 5/5 strong cation exchange pre-loaded column | Amersham Biosciences |
| SE53 Cellulose, microgranular strong cation exchange support | Whatman |
| SP Sepharose Fast Flow strong cation exchange support | Amersham Biosciences |

Example 2

Synthesis of EPO-R Agonist Peptide Dimers by Fragment Condensation

Step 1—Synthesis of $(Cbz)_2Lys$: Lysine is reacted under standard conditions with a solution of benzyl chloroformate to obtain lysine protected at its two amino groups with a Cbz group.

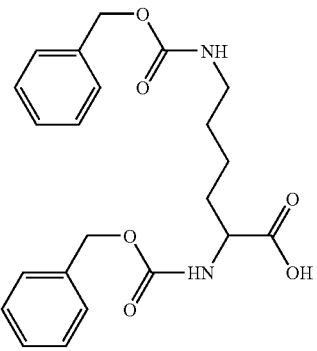

Step 2—Synthesis of Boc-TAP: Boc-TAP is syntheisized as described in Steps 1 through 3 of Example 1.

Step 3—Coupling of $(Cbz)_2$-Lys and Boc-TAP: $(Cbz)_2$-Lys and Boc-TAP are coupled under standard coupling conditions to obtain $(Cbz)_2$-Lys-TAP-Boc.

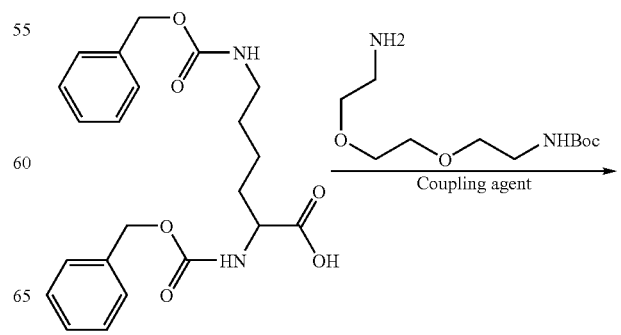

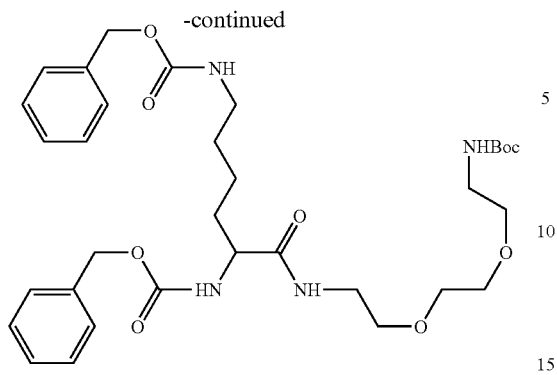

Step 4—Lys-TAP-Boc: The crude product from the previous reaction is dissolved in methanol (25 ml) and hydrogenated in presence of 5% Pd on Carbon (5% w/W) under balloon pressure for 16 hrs. The mixture is filtered, washed with methanol and the filtrate concentrated in vacuo to provide the crude Lys-TAP-Boc product

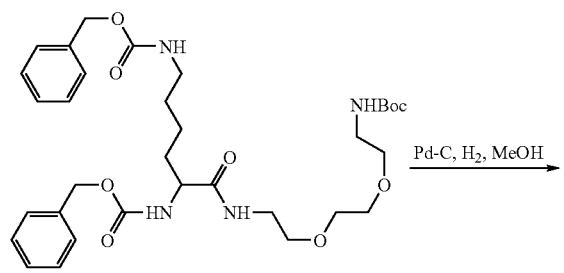

Step 5—Synthesis of peptide monomers by fragment condensation: Four peptide fragments of the peptide monomer sequence are synthesized by standard techniques. These partially protected fragments are then subjected to two independent rounds of coupling. In the first round, the N-terminal half of the monomer is formed by coupling two of the peptide fragments, while the C-terminal half of the monomer is formed by coupling the other two of the peptide fragments. In the second round of coupling, the N-terminal and C-terminal halves are coupled to form the fully protected monomer. The monomer is then OBn-deprotected by standard techniques.

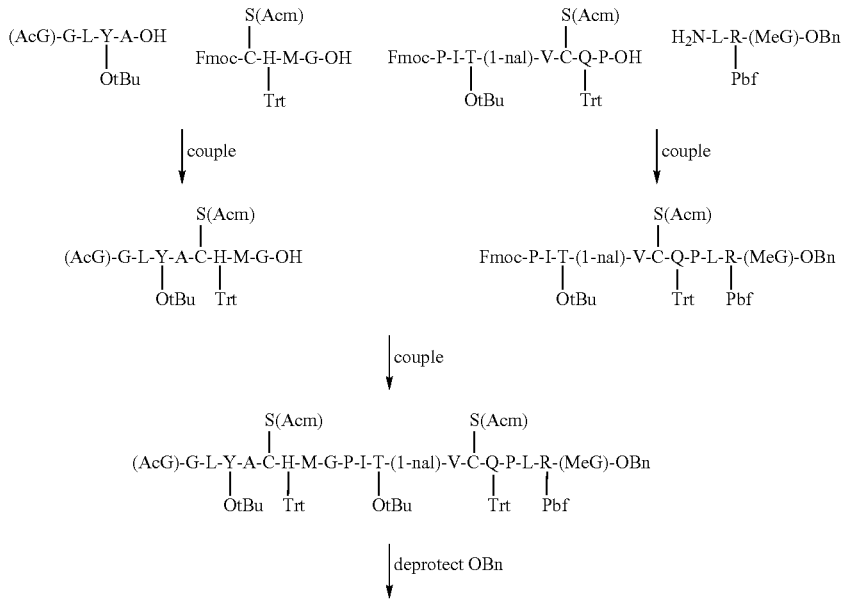

-continued

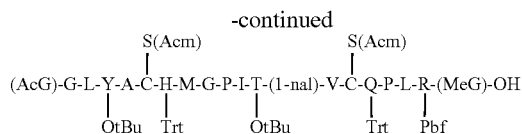

Step 6—Oxidation of peptide monomers to form intramolecular disulfide bonds: The OBn-deprotected condensed peptide monomers (SEQ ID NO: 12) are then oxidized with under iodide to form intramolecular disulfide bonds between the Acm-protected cysteine residues of the monomers.

-continued

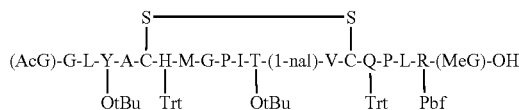

Step 7—Coupling of Lys-TAP-Boc to oxidized OBn-deprotected monomers to form a peptide dimer: Lys-TAP-Boc is coupled to a two-fold molar excess of the oxidized OBn-deprotected monomers under standard conditions to form a peptide dimer. The peptide dimer is then deprotected under standard conditions.

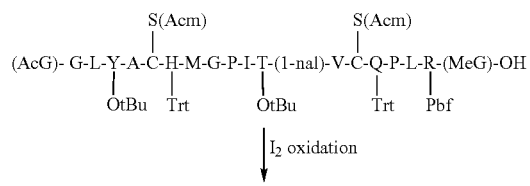

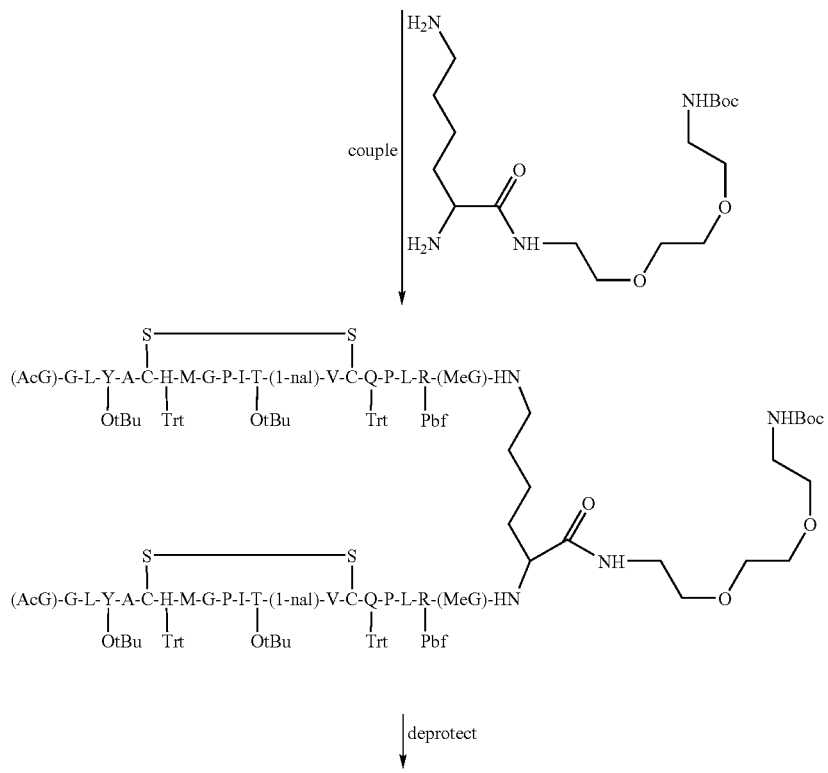

-continued

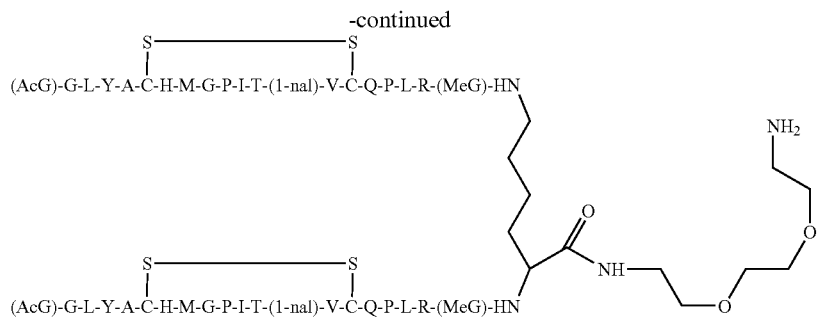

Step 8—PEGylation of deprotected dimer: The deprotected peptide dimer is then PEGylated as described in Step 10 of Example 1.

Step 9—Ion exchange purification: The PEGylated peptide dimer is then purified as described in Step 11 of Example 1.

Example 3

In Vitro Activity Assays

This example describes various in vitro assays that are useful in evaluating the activity and potency of EPO-R agonist peptides of the invention. The results for these assays demonstrate that the novel peptides of this invention bind to EPO-R and activate EPO-R signaling. Moreover, the results for these assays show that the novel peptide compositions exhibit a surprising increase in EPO-R binding affinity and biological activity compared to EPO mimetic peptides that have been previously described.

EPO-R agonist peptide dimers are prepared according to the methods provided in Example 1 or Example 2. The potency of these peptide dimers is evaluated using a series of in vitro activity assays, including: a reporter assay, a proliferation assay, a competitive binding assay, and a C/BFU-e assay. These four assays are described in further detail below.

The results of these in vitro activity assays are summarized in Table 2.

1. Reporter Assay

This assay is based upon a on a murine pre-B-cell line derived reporter cell, Baf3/EpoR/GCSFR fos/lux. This reporter cell line expresses a chimeric receptor comprising the extra-cellular portion of the human EPO receptor to the intra-cellular portion of the human GCSF receptor. This cell line is further transfected with a fos promoter-driven luciferase reporter gene construct. Activation of this chimeric receptor through addition of erythropoietic agent results in the expression of the luciferase reporter gene, and therefore the production of light upon addition of the luciferase substrate luciferin. Thus, the level of EPO-R activation in such cells may be quantitated via measurement of luciferase activity.

The Baf3/EpoR/GCSFR fos/ux cells are cultured in DMEM/F12 medium (Gibco) supplemented with 10% fetal bovine serum (FBS; Hyclone), 10% WEHI-3 supernatant (the supernatant from a culture of WEHI-3 cells, ATCC # TIB-68), and penicillin/streptomycin. Approximately 18 h before the assay, cells are starved by transferring them to DMEM/F12 medium supplemented with 10% FBS and 0.1% WEHI-3 supernatant. On the day of assay, cells are washed once with DMEM/F12 medium supplemented with 10% FBS (no WEHI-3 supernatant), then 1×10$^6$ cells/mL are cultured in the presence of a known concentration of test peptide, or with EPO(R & D Systems Inc., Minneapolis, Minn.) as a positive control, in DMEM/F12 medium supplemented with 10% FBS (no WEHI-3 supernatant). Serial dilutions of the test peptide are concurrently tested in this assay. Assay plates are incubated for 4 h at 37° C. in a 5% $CO_2$ atmosphere, after which luciferin (Steady-Glo; Promega, Madison, Wis.) is added to each well. Following a 5-minute incubation, light emission is measured on a Packard Topcount Luminometer (Packard Instrument Co., Downers Grove, Ill.). Light counts are plotted relative to test peptide concentration and analysed using Graph Pad software. The concentration of test peptide that results in a half-maximal emission of light is recorded as the EC50 [See Table 2: Reporter EC50].

2. Proliferation Assay

This assay is based upon a murine pre-B-cell line, Baf3, transfected to express human EPO-R. Proliferation of the resulting cell line, BaF3/Gal4/Elk/EPOR, is dependent on EPO-R activation. The degree of cell proliferation is quantitated using MTT, where the signal in the MTT assay is proportional to the number of viable cells.

The BaF3/Gal4/Elk/EPOR cells are cultured in spinner flasks in DMEM/F12 medium (Gibco) supplemented with 10% FBS (Hyclone) and 2% WEHI-3 supernatant (ATCC # TIB-68). Cultured cells are starved overnight, in a spinner flask at a cell density of 1×10$^6$ cells/ml, in DMEM/F12 medium supplemented with 10% FBS and 0.1% WEHI-3 supernatant. The starved cells are then washed twice with Dulbecco's PBS (Gibco), and resuspended to a density of 1×10$^6$ cells/ml in DMEM/F12 supplemented with 10% FBS (no WEHI-3 supernatant). 50 µL aliquots (~50,000 cells) of the cell suspension are then plated, in triplicate, in 96 well assay plates. 50 µL aliquots of dilution series of test EPO mimetic peptides, or 50 µL EPO(R & D Systems Inc., Minneapolis, Minn.) or Aranesp™ (darbepoeitin alpha, an ERO-R agonist commerically available from Amgen) in DMEM/F12 media supplemented with 10% FBS (no WEHI-3 supernatant 1) are added to the 96 well assay plates (final well volume of 100 µL). For example, 12 different dilutions may be tested where the final concentration of test peptide (or control EPO peptide) ranges from 810 pM to 0.0045 pM. The plated cells are then incubated for 48 h at 37° C. Next, 10 µL of MTT (Roche Diagnostics) is added to each culture dish well, and then allowed to incubate for 4 h. The reaction is then stopped by adding 10% SDS+0.01N HCl. The plates are then incubated overnight at 37° C. Absorbance of each well at a wavelenght of 595 nm is then measured by spectrophotometry. Plots of the absorbance readings versus test peptide concentration are constructed and the EC50 calculated using Graph Pad software. The concentration of test peptide that results in a half-maximal absorbance is recorded as the EC50 [See Table 2: Proliferation EC50].

3. Competitive Binding Assay

Competitive binding calculations are made using an assay in which a light signal is generated as a function of the proximity of two beads: a streptavidin donor bead bearing a biotinylated EPO-R-binding peptide tracer and an acceptor bead to which is bound EPO-R. Light is generated by non-radiative energy transfer, during which a singlet oxygen is released from a first bead upon illumination, and contact with the released singlet oxygen causes the second bead to emit light. These bead sets are commercially available (Packard). Bead proximity is generated by the binding of the EPO-R-binding peptide tracer to the EPO-R. A test peptide that competes with the EPO-R-binding peptide tracer for binding to EPO-R will prevent this binding, causing a decrease in light emission.

In more detail the method is as follows: Add 4 µL of serial dilutions of the test EPO-R agonist peptide, or positive or negative controls, to wells of a 384 well plate. Thereafter, add 2 µL/well of receptor/bead cocktail. Receptor bead cocktail consists of: 15 µL of 5 mg/ml streptavidin donor beads (Packard), 15 µL of 5 mg/ml monoclonal antibody ab179 (this antibody recognizes the portion of the human placental alkaline phosphatase protein contained in the recombinant EPO-R), protein A-coated acceptor beads (protein A will bind to the ab179 antibody; Packard), 112.5 µL of a 1:6.6 dilution of recombinant EPO-R (produced in Chinese Hamster Ovary cells as a fusion protein to a portion of the human placental alkaline phosphatase protein which contains the ab179 target epitope) and 607.5 µL of Alphaquest buffer (40 mM HEPES, pH 7.4; 1 mM $MgCl_2$; 0.1% BSA, 0.05% Tween 20). Tap to mix. Add 2 µL/well of the biotinylated EPO-R-binding peptide tracer, (30 nM final concentration). The peptide tracer, an EPO-R binding peptide, is made according to the methods described in Example 1, with sequence Biotin-GGLYACHMGPITWVCQPLRG (SEQ ID NO: 4).

AF33068

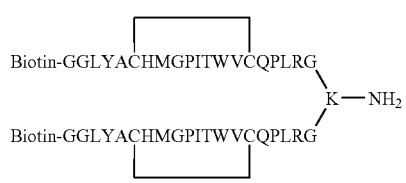

Centrifuge 1 min to mix. Seal plate with Packard Top Seal and wrap in foil. Incubate overnight at room temperature. After 18 hours read light emission using an AlphaQuest reader (Packard). Plot light emission vs concentration of peptide and analyse with Graph Pad or Excel.

The concentration of test peptide that results in a 50% decrease in light emission, relative to that observed without test peptide, is recorded as the IC50 [See Table 2: AQ IC50].

4. C/BFU-e Assay

EPO-R signaling stimulates the differentiation of bone marrow stem cells into proliferating red blood cell presursors. This assay measures the ability of test peptides to stimulate the proliferation and differentiation of red blood cell precursors from primary human bone marrow pluripotent stem cells.

For this assay, serial dilutions of test peptide are made in IMDM medium (Gibco) supplemented with 10% FBS (Hyclone). These serial dilutions, or positive control EPO peptide, are then added to methylcellulose to give a final volume of 1.5 mL. The methylcellulose and peptide mixture is then vortexed thoroughly. Aliquots (100,000 cells/mL) of human, bone marrow derived CD34+ cells (Poietics/Cambrex) are thawed. The thawed cells are gently added to 0.1 mL of 1 mg/ml DNAse (Stem Cells) in a 50 mL tube. Next, 40–50 mL IMDM medium is added gently to cells: the medium is added drop by drop along the side of the 50 mL tube for the first 10 mL, and then the remaining volume of medium is slowly dispensed along the side of the tube. The cells are then spun at 900 rpm for 20 min, and the media removed carefully by gentle aspiration. The cells are resuspended in 1 ml of IMDM medium and the cell density per mL is counted on hemacytometer slide (10 µL aliquot of cell suspension on slide, and cell density is the average count× 10,000 cells/ml). The cells are then diluted in IMDM medium to a cell density of 15,000 cells/mL. A 100 µL of diluted cells is then added to each 1.5 mL methyl cellulose plus peptide sample (final cell concentration in assay media is 1000 cells/mL), and the mixture is vortexed. Allow the bubbles in the mixture to disappear, and then aspirate 1 mL using blunt-end needle. Add 0.25 mL aspirated mixture from each sample into each of 4 wells of a 24-well plate (Falcon brand). Incubate the plated mixtures at 37° C. under 5% $CO_2$ in a humid incubator for 14 days. Score for the presence of erythroid colonies using a phase microscope (5×–10× objective, final magnification of 100×). The concentration of test peptide at which the numer of formed colonies is 90% of maximum, relative to that observed with the EPO positive control, is recorded as the EC90 [See Table 2: C/BFU-e EC90].

5. Radioligand Competitive Binding Assay

An alternative radioligand competition binding assay can also be used to measure $IC_{50}$ values of peptides in this invention. This assay measures binding of $^{125}$-EPO to EPOr. The assay is preferably performed according to the following exemplary protocol:

A. Materials

| | |
|---|---|
| Recombinant Human EPO R/Fc Chimera | Identification: Recombinant Human EPO R/Fc Chimera<br>Supplier: R&D Systems (Minneapolis, MN, US)<br>Catalog number: 963-ER<br>Lot number: EOK033071<br>Storage: 4° C. |
| Iodinated recombinant human Erythropoietin | Identification: (3[$^{125}$I]iodotyrosyl)Erythropoietin, human recombinant, high specific activity, 370 kBq, 10 µCi |

| | -continued |
|---|---|
| | Supplier: Amersham Biosciences (Piscataway, NJ, US)<br>Catalog number: IM219-10 μCi<br>Lot number:<br>Storage: 4° C. |
| Protein-G Sepharose | Identification: Protein-G Sepharose 4 Fast Flow<br>Supplier: Amersham Biosciences (Piscataway, NJ, US)<br>Catalog number 17-0618-01<br>Lot number:<br>Storage: 4° C. |
| Assay Buffer | Phosphate Buffered Saline (PBS), pH 7.4, containing 0.1%<br>Bovine Serum Albumin and 0.1% Sodium Azide<br>Storage: 4° C. |

B. Determination of Appropriate Receptor Concentration.

One 50 μg vial of lyophilized recombinant EPOr extracellular domain fused to the Fc portion of human IgG1 is reconstituted in 1 mL of assay buffer. To determine the correct amount of receptor to use in the assay, 100 μL serial dilutions of this receptor preparation are combined with approximately 20,000 cpm in 200 μL of iodinated recombinant human Erythropoietin ($^{125}$I-EPO) in 12×75 mm polypropylene test tubes. Tubes are capped and mixed gently at 4° C. overnight on a LabQuake rotating shaker.

The next day, 50 μL of a 50% slurry of Protein-G Sepharose is added to each tube. Tubes are then incubated for 2 hours at 4° C., mixing gently. The tubes are then centrifuged for 15 min at 4000 RPM (3297×G) to pellet the protein-G sepharose. The supernatants are carefully removed and discarded. After washing 3 times with 1 mL of 4° C. assay buffer, the pellets are counted in a Wallac Wizard gamma counter. Results are then analyzed and the dilution required to reach 50% of the maximum binding value is calculated.

C. $IC_{50}$ Determination for Peptide

To determine the $IC_{50}$ of Peptide I, 100 μL serial dilutions of the peptide are combined with 100 μL of recombinant erythropoietin receptor (100 pg/tube) in 12×75 mm polypropylene test tubes. Then 100 μL of iodinated recombinant human Erythropoietin ($^{125}$I-EPO) is added to each tube and the tubes are capped and mixed gently at 4° C. overnight.

The next day, bound $^{125}$I-EPO is quantitated as described above. The results are analyzed and the $IC_{50}$ value calculated using Graphpad Prism version 4.0, from GraphPad Software, Inc. (San Diego, Calif.). The assay is repeated two or more times for each peptide tested, for a total of 3 or more replicate $IC_{50}$ determinations.

TABLE 2

In vitro activity assays for peptide dimers

| Compound designation | Peptide dimer | Reporter EC50 (pM) | Proliferation EC50 (nM) | IC50 (pM) | C/BFU-e EC90 (nM) |
|---|---|---|---|---|---|
| AF35645 | 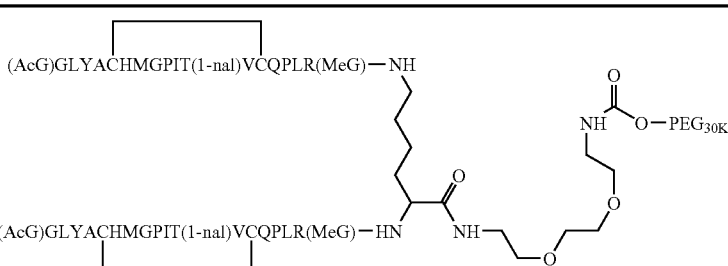 | . . . | . . . | 110 | 2.2 |
| AF35527 | 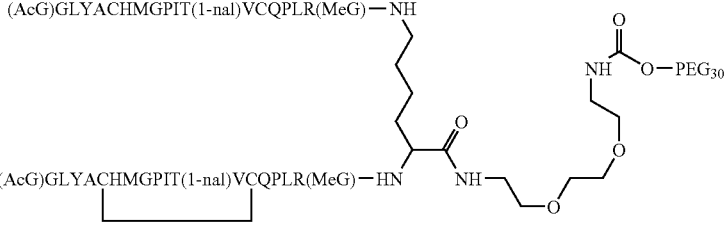 | 150 | 72 | . . . | 2.7 |

Example 4

In Vivo Activity Assays

This example describes various in vivo assays that are useful in evaluating the activity and potency of EPO-R agonist peptides of the invention. EPO-R agonist peptide dimers are prepared according to the methods provided in Example 1 or Example 2. The in vivo activity of these peptide monomers and dimers is evaluated using a series assays, including a polycythemic exhypoxic mouse bioassay and a reticulocyte assay. These two assays are described in further detail below.

1. Polycythemic Exhypoxic Mouse Bioassay

Test peptides are assayed for in vivo activity in the polycythemic exhypoxic mouse bioassay adapted from the method described by Cotes and Bangham (1961), Nature 191: 1065–1067. This assay examines the ability of a test peptide to function as an EPO mimetic: i.e., to activate EPO-R and induce new red blood cell synthesis. Red blood cell synthesis is quantitated based upon incorporation of radiolabeled iron into hemoglobin of the synthesized red blood cells.

BDF1 mice are allowed to acclimate to ambient conditions for 7–10 days. Body weights are determined for all animals, and low weight animals (<15 grams) are not used. Mice are subjected to successive conditioning cycles in a hypobaric chamber for a total of 14 days. Each 24 hour cycle consista of 18 hr at 0.40±0.02% atmospheric pressure and 6 hr at ambient pressure. After conditioning the mice are maintained at ambient pressure for an additional 72 hr prior to dosing.

Test peptides, or recombinant human EPO standards, are diluted in PBS+0.1% BSA vehicle (PBS/BSA). Peptide monomer stock solutions are first solubilized in dimethyl sulfoxide (DMSO). Negative control groups include one group of mice injected with PBS/BSA alone, and one group injected with 1% DMSO. Each dose group containa 10 mice. Mice are injected subcutaneously (scruff of neck) with 0.5 mL of the appropriate sample.

Forty eight hours following sample injection, the mice are administered an intraperitoneal injection of 0.2 ml of $Fe^{59}$ (Dupont, NEN), for a dose of approximately 0.75 μCuries/mouse. Mouse body weights are determined 24 hr after $Fe^{59}$ administration, and the mice are sacrificed 48 hr after $Fe^{59}$ administration. Blood is collected from each animal by cardiac puncture and hematocrits are determined (heparin was used as the anticoagulant). Each blood sample (0.2 ml) is analyzed for $Fe^{59}$ incorporation using a Packard gamma counter. Non-responder mice (i.e., those mice with radioactive incorporation less than the negative control group) are eliminated from the appropriate data set. Mice that have hematocrit values less than 53% of the negative control group are also eliminated.

Results are derived from sets of 10 animals for each experimental dose. The average amount of radioactivity incorporated [counts per minute (CPM)] into blood samples from each group is calculated.

2. Reticulocyte Assay

Normal BDF1 mice are dosed (0.5 mL, injected subcutaneously) on three consecutive days with either EPO control or test peptide. At day three, mice are also dosed (0.1 mL, injected intraperitoneally) with iron dextran (100 mg/ml). At day five, mice are anesthetized with $CO_2$ and bled by cardiac puncture. The percent (%) reticulocytes for each blood sample is determined by thiazole orange staining and flow cytometer analysis (retic-count program). Hematocrits are manually determined. The corrected percent of reticulocytes is determined using the following formula:

$$\% \text{ RETIC}_{CORRECTED} = \% \text{ RETIC}_{OBSERVED} \times (\text{Hematocrit}_{INDIVIDUAL}/\text{Hematocrit}_{NORMAL})$$

3. Hematological Assay

Normal CD1 mice are dosed with four weekly bolus intravenous injections of either EPO positive control, test peptide, or vehicle. A range of positive control and test peptide doses, expressed as mg/kg, are tested by varying the active compound concentration in the formulation. Volumes injected are 5 ml/kg. The vehicle control group is comprised twelve animals, while 8 animals are in each of the remaining dose groups. Daily viability and weekly body weights are recorded.

The dosed mice are mice are fasted and then anesthetized with inhaled isoflurane and terminal blood samples are collected via cardiac or abdominal aorta puncture on Day 1 (for vehicle control mice) and on Days 15 and 29 (4 mice/group/day). The blood is transferred to Vacutainer® brand tubes. Preferred anticoagulant is ethylenediaminetetraacetic acid (EDTA).

Blood samples are evaluated for endpoints measuring red blood synthesis and physiology such as hematocrit (Hct), hemoglobin (Hgb) and total erythrocyte count (RBC) using automated clinical analysers well known in the art (e.g., those made by Coulter, Inc.).

Example 5

Synthesis of EPO-R Agonist Peptide Homodimers of Peptide Monomers Having the Amino Acid Sequence (AcG)GLYACHMGPIT(1-nal)VCQPLRK (SEQ ID NO: 1)

Step 1—Synthesis of peptide monomers: Peptide monomers are synthesized using standard Fmoc chemistry on an ABI 431A peptide synthesizer, using TG-RAM resin (0.18 mmol/g Rapp Polymere, Germany). For the synthesis of peptide monomers with an amidated carboxy terminus, the fully assembled peptide is cleaved from the resin with 82.5% TFA, 5% water, 6.25% anisole, 6.25% ethanedithiol. The deprotected product is filtered from the resin and precipitated with diethyl ether. After thorough drying, the product is purified by C18 reverse phase high performance liquid chromatography with a gradient of acetonitrile/water in 0.1% trifluoroacetic acid. The structure of the peptide is confirmed by electospray mass spectrometry. The peptide is dissolved in a 1:1 solution of DMSO:water at a concentration of 1 mg/mL to affect disulfide formation. The product is purified by C18 reverse phase high performance liquid chromatography with a gradient of acetonitrile/water in 0.1% trifluoroacetic acid. The peptide monomers may be illustrated as follows:

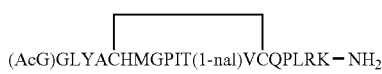

Step 2—Synthesis of the trifunctional linker: To a solution of diethyl iminoacetate (10.0 g, 52.8 mmol) and Boc-beta-alanine (10.0 g, 52.8 mmol) in 100 mL of DCM was added diisopropylcarbodiimide (8.0 mL, 51.1 mmol) over 10 minutes at room temperture. The reaction mixture warmed to ~10 degrees during the addition, then cooled back to room temperature over 20 minutes. The reaction mixture was allowed to stir overnight and the precepitated diisopropylurea was filtered off. The solvent was removed under reduced pressure to afford a gum, and the residue dissolved in ethyl acetate and again filtered to remove the additional precipatated urea. The organic phase was placed into a separtory funnel, washed (sat. NaHCO$_3$, brine, 0.5 N HCl, brine), dried (MgSO$_4$), filtered and concentrated under reduced pressure to afford the diester product as a colorless oil. The diester was taken up in a 1:1 mixture of MeOH:THF (100 mL) and to this was added water (25 mL), and then NaOH (5 g, 125 mmol). The pH was measured to be >10. The reaction mixture was stirred at room temperature for 2 h, and then acidified to pH 1 with 6N HCl. The aq. Phase was staurated with NaCl and extracted 4 times with ethyl acetate. The combined organic phase was washed (brine), dried (MgSO$_4$), and concentrated under reduced pressure to give a white semi-solid. The solid was dissolved in 50 mL of DCM and to this was added 300 mL hexane to create a white slurry. The solvent was removed under reduced pressure to afford the diacid as a white solid (14.7 g, 91.5% yield for 2 steps). To a solution of the diacid (1 g, 3.29 mmol) in 20 mL of DMF was added N-hydroxysuccinimide (770 mg, 6.69 mmol) and diisopropylcarbodiimide (1.00 mL, 6.38 mmol) and 4-dimethylaminopyridine (3 mg, 0.02 mmol). The reaction mixture was stirred overnight and the solvent removed under reduced pressure. The residue was taken up in ethyl acetate and filtered to remove the precpitated urea. The organic phase was placed into a separtory funnel, washed (sat. NaHCO$_3$, brine, 0.5 N HCl, brine), dried (MgSO$_4$), filtered and concentrated under reduced pressure to afford the di-NHS ester product as a white solid (1.12 g, 68% yield).

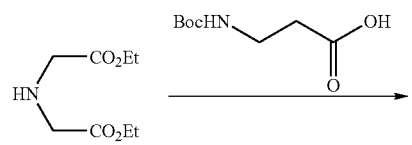

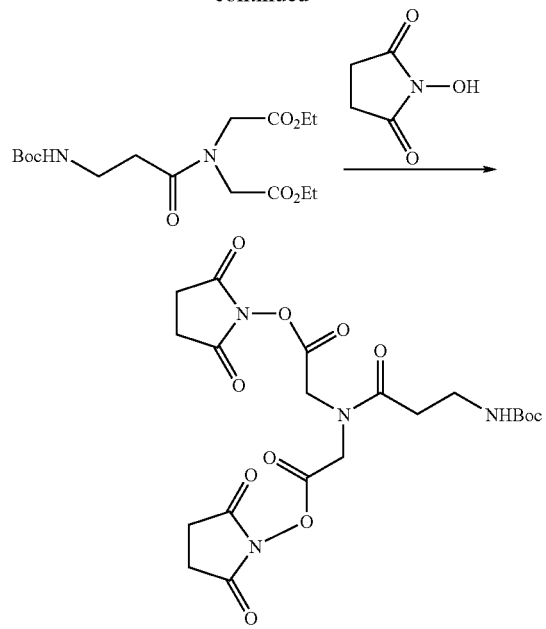

Step 3—Coupling of the trifunctional linker to the peptide monomers: For coupling to the linker, 2 eq peptide is mixed with 1 eq of trifunctional linker in dry DMF to give clear solution, 5 eq of DIEA is added after 2 minutes. The mixture is stirred at ambient temperature for 14 h. The solvent is removed under reduced pressure and the crude product is dissolved in 80% TFA in DCM for 30 min to remove the Boc group, followed by purification with C18 reverse phase HPLC. The structure of the dimer is confirmed by electrospray mass spectrometry. This coupling reaction attaches the linker to the nitrogen atom of the ε-amino group of the lysine residue of each monomer. The process is shown below with SEQ ID NO: 1.

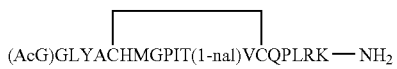

(AcG)GLYACHMGPIT(1-nal)VCQPLRK—NH$_2$

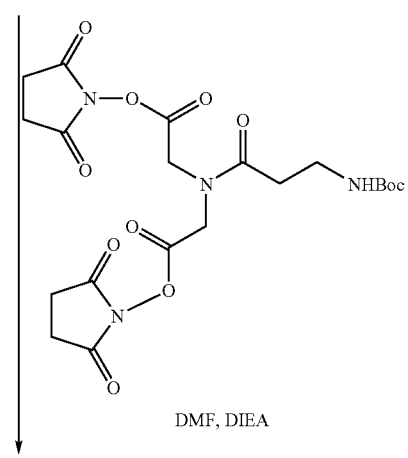

DMF, DIEA

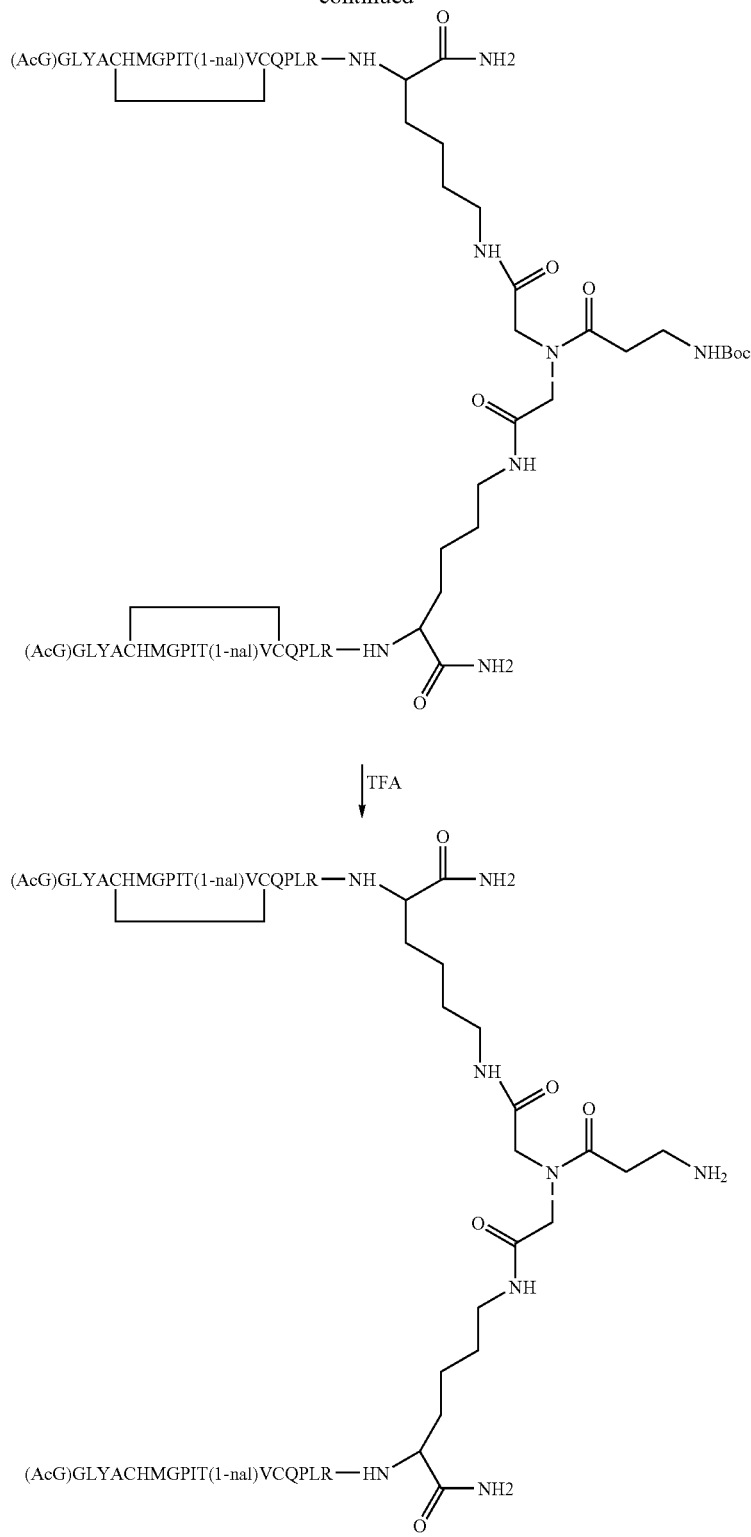

Step 4—PEGylation of the Peptide Dimer:

PEGylation via a carbamate bond: The peptide dimer is mixed with an equal amount (mole basis) of activated PEG species (MPEG-NPC from NOF Corp. Japan) in dry DMF to afford a clear solution. After 5 minutes 4 eq of DIEA is added to above solution. The mixture is stirred at ambient temperature 14 h, followed by purification with C18 reverse phase HPLC. The structure of PEGylated peptide is confirmed by MALDI mass. The purified peptide was also subjected to purification via cation ion exchange chromatography as outlined below. The mPEG-NPC PEGylation is shown below using SEQ ID NO: 1.

added to above solution. The mixture is stirred at ambient temperature 2 h, followed by purification with C18 reverse phase HPLC. The structure of PEGylated peptide was con-

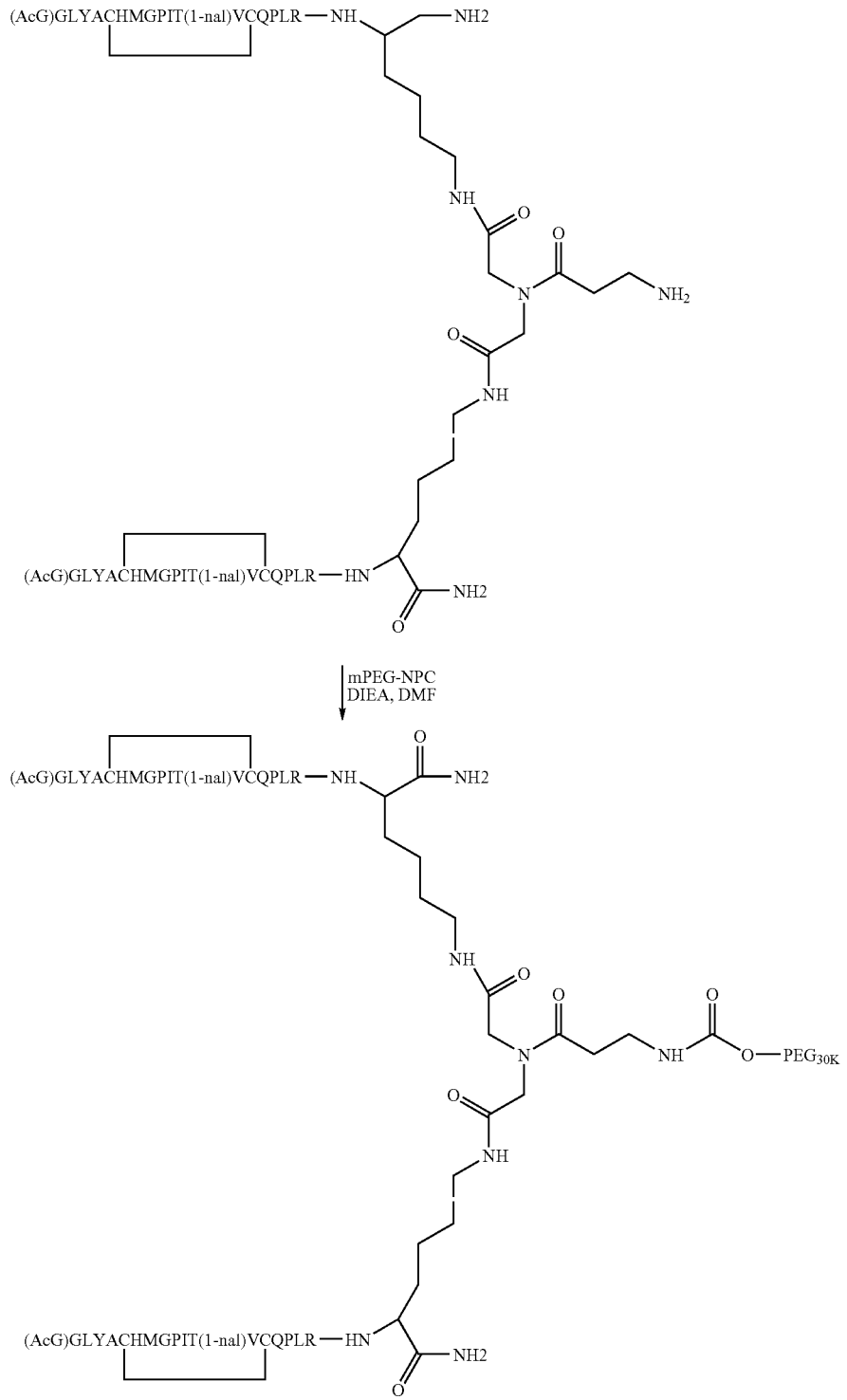

PEGylation via an amide bond: The peptide dimer is mixed with an equal amount (mole basis) of activated PEG species (PEG-SPA-NHS from Shearwater Corp, USA) in dry DMF to afford a clear solution. After 5 minutes 10 eq of DIEA is firmed by MALDI mass. The purified peptide was also subjected to purification via cation ion exchange chromatography as outlined below. The PEG-SPA-NHS PEGylation is shown below using SEQ ID NO: 1.

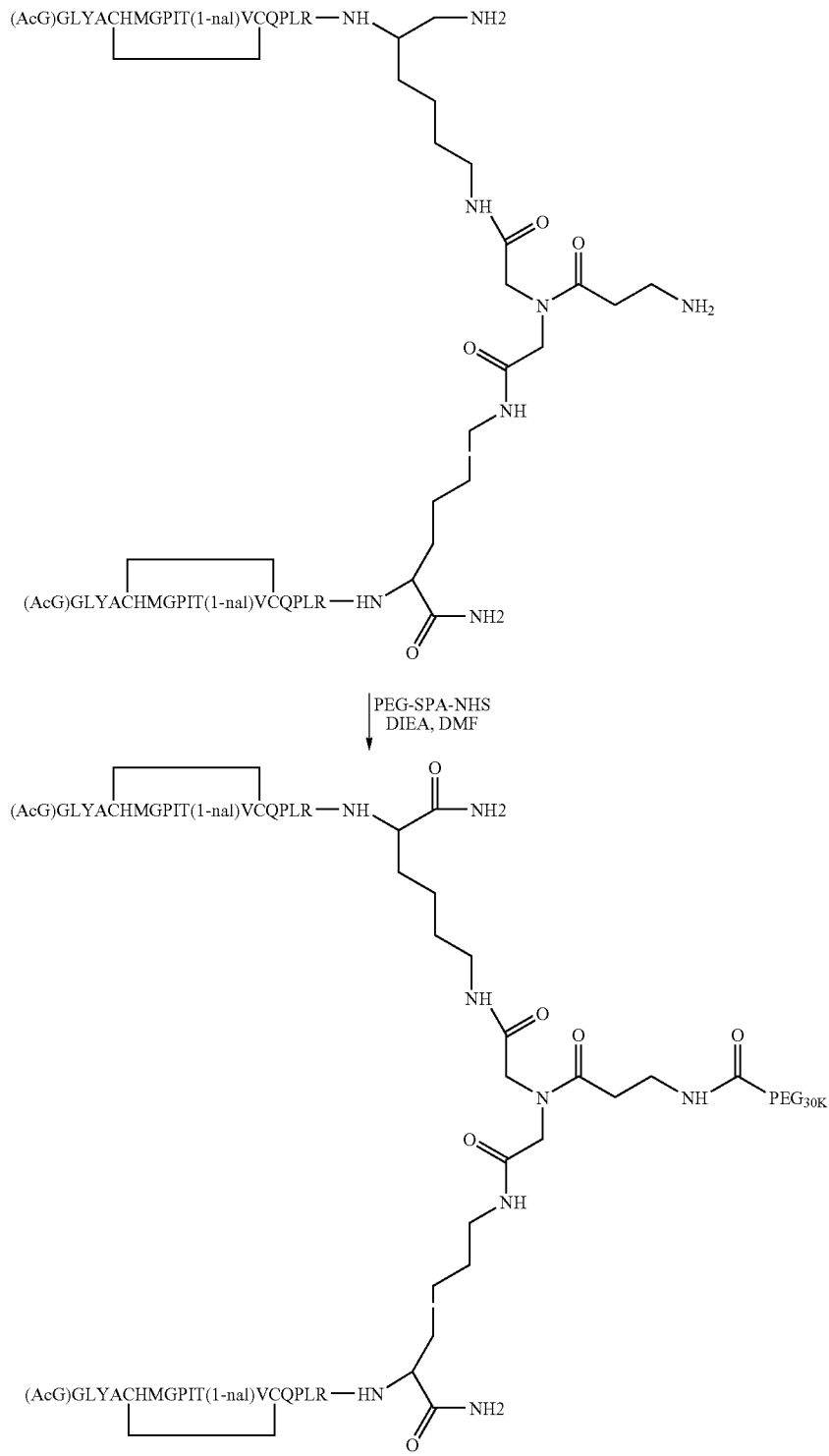

Step 5: —Ion exchange purification of peptides: Several exchange supports were surveyed for their ability to separate the above peptide-PEG conjugate from unreacted (or hydrolyzed) PEG, in addition to their ability to retain the starting dimeric peptides. The ion exchange resin (2–3 g) was loaded into a 1 cm column, followed by conversion to the sodium form (0.2 N NaOH loaded onto column until elutant was pH 14, ca. 5 column volumes), and than to the hydrogen form (eluted with either 0.1 N HCl or 0.1 M HOAc until elutant matched load pH, ca. 5 column volumes), followed by washing with 25% ACN/water until pH 6. Either the peptide prior to conjugation or the peptide-PEG conjugate was dissolved in 25% ACN/water (10 mg/mL) and the pH adjusted to <3 with TFA, then loaded on the column. After washing with 2–3 column volumes of 25% ACN/water and collecting 5 mL fractions, the peptide was released from the column by elution with 0.1 M NH$_4$OAc in 25% ACN/water, again collecting 5 mL fractions. Analysis via HPLC revealed which fractions contained the desired peptide. Analysis with an Evaporative Light-Scattering Detector (ELSD) indicated that when the peptide was retained on the column and was eluted with the NH$_4$OAc solution (generally between fractions 4 and 10), no non-conjugated PEG was observed as a contaminant. When the peptide eluted in the initial wash buffer (generally the first 2 fractions), no separation of desired PEG-conjugate and excess PEG was observed.

The following columns successfully retained both the peptide and the peptide-PEG conjugate, and successfully purified the peptide-PEG conjugate from the unconjugates peptide:

TABLE 3

| Ion Exhange Resins | |
|---|---|
| Support | Source |
| Mono S HR 5/5 strong cation exchange pre-loaded column | Amersham Biosciences |
| SE53 Cellulose, microgranular strong cation exchange support | Whatman |
| SP Sepharose Fast Flow strong cation exchange support | Amersham Biosciences |

TABLE 3-continued

Example 6

Synthesis of EPO-R Agonist Peptide Homodimers of Peptide Monomers Having the Amino Acid Sequence (AcG)GLYACHMGPIT(1-nal)VCQPLR(MeG)K (SEQ ID NO: 2)

EPO-R agonist peptide homodimers of peptide monomers having the amino acid sequence (AcG)GLYACHMGPIT(1-nal)VCQPLR(MeG)K (SEQ ID NO: 2) are synthesized as described in Example 1, except that in Step 1 the synthesized peptide monomers are:

(AcG)GLYACHMGPIT(1-nal)VCQPLR(MeG)K

Where the PEG is attached to the linker via a carbamate linkage, the final product of this synthesis using SEQ ID NO: 2 may by illustrated structurally as follows:

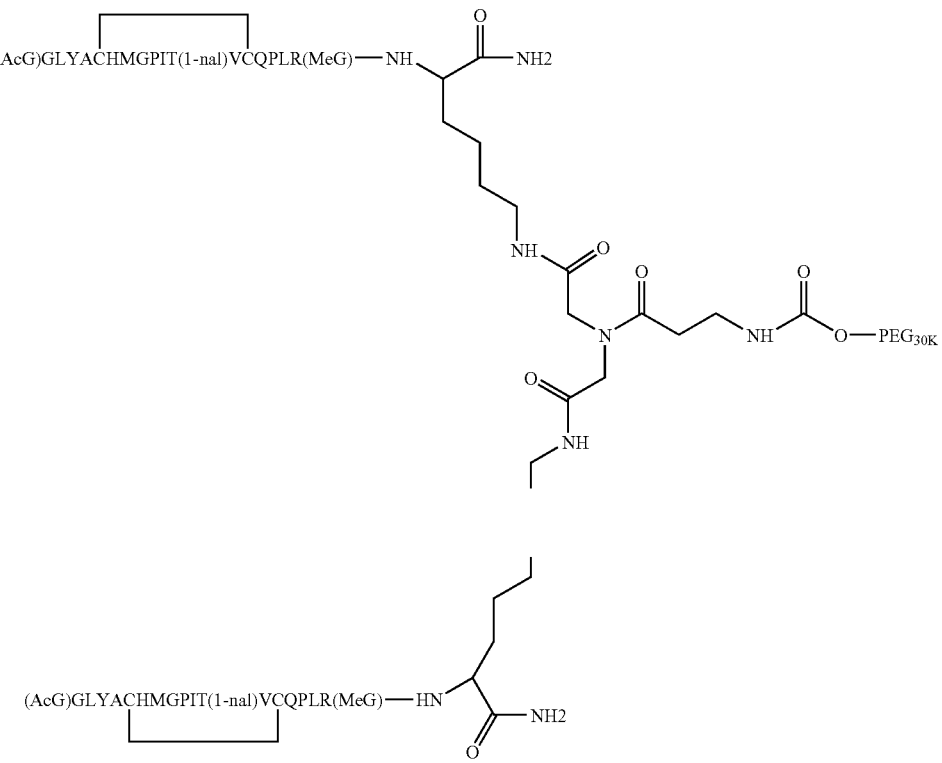

Where the PEG is attached to the linker via an amide linkage, the final product of this synthesis using SEQ ID NO: 2 may by illustrated structurally as follows:

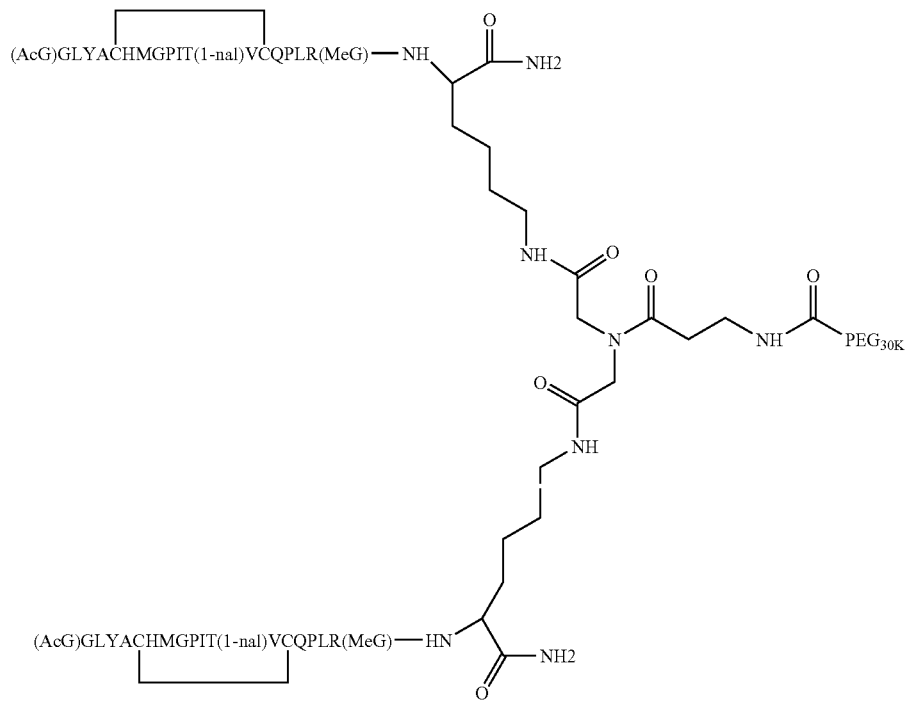

Example 7

In vitro Activity Assays

This example describes various in vitro assays that are useful in evaluating the activity and potency of EPO-R agonist peptides of the invention. The results for these assays demonstrate that the novel peptides of this invention bind to EPO-R and activate EPO-R signaling. Moreover, the results for these assays show that the novel peptide compositions exhibit a surprising increase in EPO-R binding affinity and biological activity compared to EPO mimetic peptides that have been previously described.

EPO-R agonist peptide monomers and dimers are prepared according to the methods provided in Example 1 or Example 2. The potency of these peptide dimers is evaluated using a series of in vitro activity assays, including: a reporter assay, a proliferation assay, a competitive binding assay, and a C/BFU-e assay. These four assays are described in further detail below.

The results of these in vitro activity assays are summarized in Table 2.

1. Reporter Assay

This assay is based upon a on a murine pre-B-cell lin derived reporter cell, Baf3/EpoR/GCSFR fos/lux. This reporter cell line expresses a chimeric receptor comprising the extra-cellular portion of the human EPO receptor to the intra-cellular portion of the human GCSF receptor. This cell line is further transfected with a fos promoter-driven luciferase reporter gene construct. Activation of this chimeric receptor through addition of erythropoietic agent results in the expression of the luciferase reporter gene, and therefore the production of light upon addition of the luciferase substrate luciferin. Thus, the level of EPO-R activation in such cells may be quantitated via measurement of luciferase activity.

The Baf3/EpoRIGCSFR fos/lux cells are cultured in DMEM/F12 medium (Gibco) supplemented with 10% fetal bovine serum (FBS; Hyclone), 10% WEHI-3 supernatant (the supernatant from a culture of WEHI-3 cells, ATCC # TIB-68), and penicillin/streptomycin. Approximately 18 h before the assay, cells are starved by transferring them to DMEM/F12 medium supplemented with 10% FBS and 0.1% WEHI-3 supernatant. On the day of assay, cells are washed once with DMEM/F12 medium supplemented with 10% FBS (no WEHI-3 supernatant), then $1 \times 10^6$ cells/mL are cultured in the presence of a known concentration of test peptide, or with EPO(R & D Systems Inc., Minneapolis, Minn.) as a positive control, in DMEM/F12 medium supplemented with 10% FBS (no WEHI-3 supernatant). Serial dilutions of the test peptide are concurrently tested in this assay. Assay plates are incubated for 4 h at 37° C. in a 5% $CO_2$ atmosphere, after which luciferin (Steady-Glo; Promega, Madison, Wis.) is added to each well. Following a 5-minute incubation, light emission is measured on a Packard Topcount Luminometer (Packard Instrument Co., Downers Grove, Ill.). Light counts are plotted relative to test peptide concentration and analysed using Graph Pad software. The concentration of test peptide that results in a half-maximal emission of light is recorded as the EC50.

2. Proliferation Assay

This assay is based upon a murine pre-B-cell line, Ba3, transfected to express human EPO-R. Proliferation of the resulting cell line, BaF3/Gal4/Elk/EPOR, is dependent on EPO-R activation. The degree of cell proliferation is quantitated using MTT, where the signal in the MTT assay is proportional to the number of viable cells.

The BaF3/Gal4/Elk/EPOR cells are cultured in spinner flasks in DMEM/F12 medium (Gibco) supplemented with 10% FBS (Hyclone) and 2% WEHI-3 supernatant (ATCC # TIB-68). Cultured cells are starved overnight, in a spinner flask at a cell density of $1\times10^6$ cells/ml, in DMEM/F12 medium supplemented with 10% FBS and 0.1% WEHI-3 supernatant. The starved cells are then washed twice with Dulbecco's PBS (Gibco), and resuspended to a density of $1\times10^6$ cells/ml in DMEM/F12 supplemented with 10% FBS (no WEHI-3 supernatant). 50 µL aliquots (~50,000 cells) of the cell suspension are then plated, in triplicate, in 96 well assay plates. 50 µL aliquots of dilution series of test EPO mimetic peptides, or 50 µL EPO(R & D Systems Inc., Minneapolis, Minn.) or Aranesp™ (darbepoeitin alpha, an ERO-R agonist commerically available from Amgen) in DMEM/F12 media supplemented with 10% FBS (no WEHI-3 supernatant 1) are added to the 96 well assay plates (final well volume of 100 µL). For example, 12 different dilutions may be tested where the final concentration of test peptide (or control EPO peptide) ranges from 810 pM to 0.0045 pM. The plated cells are then incubated for 48 h at 37° C. Next, 10 µL of MTT (Roche Diagnostics) is added to each culture dish well, and then allowed to incubate for 4 h. The reaction is then stopped by adding 10% SDS+0.01N HCl. The plates are then incubated overnight at 37° C. Absorbance of each well at a wavelenght of 595 nm is then measured by spectrophotometry. Plots of the absorbance readings versus test peptide concentration are constructed and the EC50 calculated using Graph Pad software. The concentration of test peptide that results in a half-maximal absorbance is recorded as the EC50.

3. Competitive Binding Assay

Competitive binding calculations are made using an assay in which a light signal is generated as a function of the proximity of two beads: a streptavidin donor bead bearing a biotinylated EPO-R-binding peptide tracer and an acceptor bead to which is bound EPO-R. Light is generated by non-radiative energy transfer, during which a singlet oxygen is released from a first bead upon illumination, and contact with the released singlet oxygen causes the second bead to emit light. These bead sets are commercially available (Packard). Bead proximity is generated by the binding of the EPO-R-binding peptide tracer to the EPO-R. A test peptide that competes with the EPO-R-binding peptide tracer for binding to EPO-R will prevent this binding, causing a decrease in light emission.

In more detail the method is as follows: Add 4 µL of serial dilutions of the test EPO-R agonist peptide, or positive or negative controls, to wells of a 384 well plate. Thereafter, add 2 µL/well of receptor/bead cocktail. Receptor bead cocktail consists of: 15 µL of 5 mg/ml streptavidin donor beads (Packard), 15 µL of 5 mg/ml monoclonal antibody ab179 (this antibody recognizes the portion of the human placental alkaline phosphatase protein contained in the recombinant EPO-R), protein A-coated acceptor beads (protein A will bind to the ab179 antibody; Packard), 112.5 µL of a 1:6.6 dilution of recombinant EPO-R (produced in Chinese Hamster Ovary cells as a fusion protein to a portion of the human placental alkaline phosphatase protein which contains the ab179 target epitope) and 607.51 µL of Alphaquest buffer (40 mM HEPES, pH 7.4; 1 mM $MgCl_2$; 0.1% BSA, 0.05% Tween 20). Tap to mix. Add 2 µL/well of the biotinylated EPO-R-binding peptide tracer, (30 nM final concentration). The peptide, trace, an EPO-R binding peptide, is made according to the methods described in Example 1, using SEQ ID NO: 4.

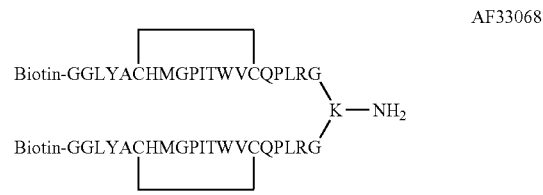

Centrifuge 1 min to mix. Seal plate with Packard Top Seal and wrap in foil. Incubate overnight at room temperature. After 18 hours read light emission using an AlphaQuest reader (Packard). Plot light emission vs concentration of peptide and analyse with Graph Pad or Excel.

The concentration of test peptide that results in a 50% decrease in light emission, relative to that observed without test peptide, is recorded as the IC50.

4. C/BFU-e Assay

EPO-R signaling stimulates the differentiation of bone marrow stem cells into proliferating red blood cell presursors. This assay measures the ability of test peptides to stimulate the proliferation and differentiation of red blood cell precursors from primary human bone marrow pluripotent stem cells.

For this assay, serial dilutions of test peptide are made in IMDM medium (Gibco) supplemented with 10% FBS (Hyclone). These serial dilutions, or positive control EPO peptide, are then added to methylcellulose to give a final volume of 1.5 mL. The methylcellulose and peptide mixture is then vortexed thoroughly. Aliquots (100,000 cells/mL) of human, bone marrow derived CD34+ cells (Poietics/Cambrex) are thawed. The thawed cells are gently added to 0.1 mL of 1 mg/ml DNAse (Stem Cells) in a 50 mL tube. Next, 40–50 mL IMDM medium is added gently to cells: the medium is added drop by drop along the side of the 50 mL tube for the first 10 mL, and then the remaining volume of medium is slowly dispensed along the side of the tube. The cells are then spun at 900 rpm for 20 min, and the media removed carefully by gentle aspiration. The cells are resuspended in 1 ml of IMDM medium and the cell density per mL is counted on hemacytometer slide (10 µL aliquot of cell suspension on slide, and cell density is the average count ×10,000 cells/ml). The cells are then diluted in IMDM medium to a cell density of 15,000 cells/mL. A 100 µL of diluted cells is then added to each 1.5 mL methyl cellulose plus peptide sample (final cell concentration in assay media is 1000 cells/mL), and the mixture is vortexed. Allow the bubbles in the mixture to disappear, and then aspirate 1 mL using blunt-end needle. Add 0.25 mL aspirated mixture from each sample into each of 4 wells of a 24-well plate (Falcon brand). Incubate the plated mixtures at 37° C. under 5% $CO_2$ in a humid incubator for 14 days. Score for the presence of erythroid colonies using a phase microscope (5×–10× objective, final magnification of 100×). The concentration of test peptide at which the numer of formed colonies is 90% of maximum, relative to that observed with the EPO positive control, is recorded as the EC90 [See Table 2: C/BFU-e EC90].

TABLE 4

In vitro activity assays for peptide dimers

| Compound designation | Peptide dimer | Reporter EC50 (pM) | Proliferation EC50 (pM) | AQ IC50 (nM) | C/BFU-e EC90 (nM) |
|---|---|---|---|---|---|
| AF36205 | | ... | ... | ... | 6.2 |

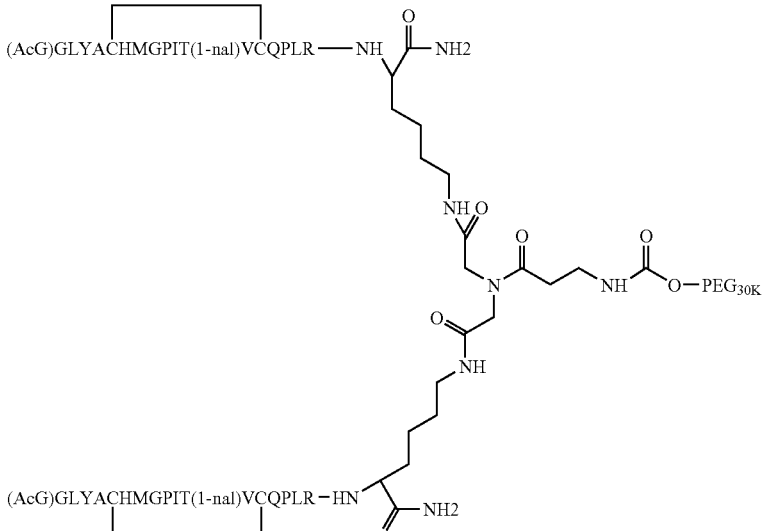

Example 8

In Vivo Activity Assays

This example describes various in, vivo assays that are useful in evaluating the activity and potency of EPO-R agonist peptides of the invention. EPO-R agonist peptide monomers and dimers are prepared according to the methods provided in Example 1. The in vivo activity of these peptide monomers and dimers is evaluated using a series assays, including a polycythemic exhypoxic mouse bioassay and a reticulocyte assay. These two assays are described in further detail below.

1. Polycythemic Exhypoxic Mouse Bioassay

Test peptides are assayed for in vivo activity in the polycythemic exhypoxic mouse bioassay adapted from the method described by Cotes and Bangham (1961), Nature 191: 1065–1067. This assay examines the ability of a test peptide to function as an EPO mimetic: i.e., to activate EPO-R and induce new red blood cell synthesis. Red blood cell synthesis is quantitated based upon incorporation of radiolabeled iron into hemoglobin of the synthesized red blood cells.

BDF1 mice are allowed to acclimate to ambient conditions for 7–10 days. Body weights are determined for all animals, and low weight animals (<15 grams) are not used. Mice are subjected to successive conditioning cycles in a hypobaric chamber for a total of 14 days. Each 24 hour cycle consista of 18 hr at 0.40±0.02% atmospheric pressure and 6 hr at ambient pressure. After conditioning the mice are maintained at ambient pressure for an additional 72 hr prior to dosing.

Test peptides, or recombinant human EPO standards, are diluted in PBS+0.1% BSA vehicle (PBS/BSA). Peptide monomer stock solutions are first solubilized in dimethyl sulfoxide (DMSO). Negative control groups include one group of mice injected with PBS/BSA alone, and one group injected with 1% DMSO. Each dose group containa 10 mice. Mice are injected subcutaneously (scruff of neck) with 0.5 mL of the appropriate sample.

Forty eight hours following sample injection, the mice are administered an intraperitoneal injection of 0.2 ml of $Fe^{59}$ (Dupont, NEN), for a dose of approximately 0.75 μCuries/mouse. Mouse body weights are determined 24 hr after $Fe^{59}$ administration, and the mice are sacrificed 48 hr after $Fe^{59}$ administration. Blood is collected from each animal by cardiac puncture and hematocrits are determined (heparin was used as the anticoagulant). Each blood sample (0.2 ml) is analyzed for $Fe^{59}$ incorporation using a Packard gamma counter. Non-responder mice (i.e., those mice with radioactive incorporation less than the negative control group) are eliminated from the appropriate data set. Mice that have hematocrit values less than 53% of the negative control group are also eliminated.

Results are derived from sets of 10 animals for each experimental dose. The average amount of radioactivity incorporated [counts per minute (CPM)] into blood samples from each group is calculated.

2. Reticulocyte Assay

Normal BDF1 mice are dosed (0.5 mL, injected subcutaneously) on three consecutive days with either EPO control or test peptide. At day three, mice are also dosed (0.1 mL, injected intraperitoneally) with iron dextran (100 mg/ml). At day five, mice are anesthetized with $CO_2$ and bled by cardiac puncture. The percent (%) reticulocytes for each blood sample is determined by thiazole orange staining and flow cytometer analysis (retic-count program). Hemat ocrits are manually determined. The corrected percent of reticulocytes is determined using the following formula:

% RETIC$_{CORRECTED}$=% RETIC$_{OBSERVED}$×(Hematocrit$_{INDIVIDUAL}$/Hematocrit$_{NORMAL}$)

3. Hematological Assay

Normal CD1 mice are dosed with four weekly bolus intravenous injections of either EPO positive control, test peptide, or vehicle. A range of positive control and test peptide doses, expressed as mg/kg, are tested by varying the active compound concentration in the formulation. Volumes injected are 5 ml/kg. The vehicle control group is comprised twelve animals, while 8 animals are in each of the remaining dose groups. Daily viability and weekly body weights are recorded.

The dosed mice are mice are fasted and then anesthetized with inhaled isoflurane and terminal blood samples are collected via cardiac or abdominal aorta puncture on Day 1 (for vehicle control mice) and on Days 15 and 29 (4 mice/group/day). The blood is transferred to Vacutainer™ brand tubes. Preferred anticoagulant is ethylenediaminetetraacetic acid (EDTA).

Blood samples are evaluated for endpoints measuring red blood synthesis and physiology such as hematocrit (Hct), hemoglobin (Hgb) and total erythrocyte count (RBC) using automated clinical analysers well known in the art (e.g., those made by Coulter, Inc.).

Example 9

Synthesis of EPO-R Agonist Peptide Homodimers of Peptide Monomers Having the Amino Acid Sequence (AcG)GLYACEMGPIT(1-nal)VCQPLRK (SEQ ID NO: 1)

Step 1—Synthesis of peptide monomers: Peptide monomers are synthesized using standard Fmoc chemistry on an ABI 431A peptide synthesizer, using TG-RAM resin (0.18 mmol/g Rapp Polymere, Germany). For the synthesis of peptide monomers with an amidated carboxy terminus, the fully assembled peptide is cleaved from the resin with 82.5% TFA, 5% water, 6.25% anisole, 6.25% ethanedithiol. The deprotected product is filtered from the resin and precipitated with diethyl ether. After thorough drying the product is purified by C18 reverse phase high performance liquid chromatography with a gradient of acetonitrile/water in 0.1% trifluoroacetic acid. The structure of the peptide is confirmed by electrospray mass spectrometry. The peptide monomers may be illustrated as follows:

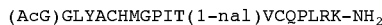
(AcG)GLYACHMGPIT(1-nal)VCQPLRK-NH$_2$

Step 2—Synthesis of the Trifunctional Linker:

To a solution of diethyl iminoacetate (10.0 g, 52.8 mmol) and Boc-beta-alanine (10.0 g, 52.8 mmol) in 100 mL of DCM was added diisopropylcarbodiimide (8.0 mL, 51.1 mmol) over 10 minutes at room temperture. The reaction mixture warmed to ~10 degrees during the addition, then cooled back to room temperature over 20 minutes. The reaction mixture was allowed to stir overnight and the precepitated diisopropylurea was filtered off. The solvent was removed under reduced pressure to afford a gum, and the residue dissolved in ethyl acetate and again filtered to remove the additional precipatated urea. The organic phase was placed into a separtory funnel, washed (sat. NaHCO$_3$, brine, 0.5 N HCl, brine), dried (MgSO$_4$), filtered and concentrated under reduced pressure to afford the diester product as a colorless oil. The diester was taken up in a 1:1 mixture of MeOH:THF (100 mL) and to this was added water (25 mL), and then NaOH (5 g, 125 mmol). The pH was measured to be >10. The reaction mixture was stirred at room temperature for 2 h, and then acidified to pH 1 with 6N HCl. The aq. Phase was saturated with NaCl and extracted 4 times with ethyl acetate. The combined organic phase was washed (brine), dried (MgSO$_4$), and concentrated under reduced pressure to give a white semi-solid. The solid was dissolved in 50 mL of DCM and to this was added 300 mL hexane to create a white slurry. The solvent was removed under reduced pressure to afford the diacid as a white solid (14.7 g, 91.5% yield for 2 steps). To a solution of the diacid (1 g, 3.29 mmol) in 20 mL of DMF was added N-hydroxysuccinimide (770 mg, 6.69 mmol) and diisopropylcarbodiimide (1.00 mL, 6.38 mmol) and 4-dimethylaminopyridine (3 mg, 0.02 mmol). The reaction mixture was stirred overnight and the solvent removed under reduced pressure. The residue was taken up in ethyl acetate and filtered to remove the precipitated urea. The organic phase was placed into a separtory funnel, washed (sat. NaHCO$_3$, brine, 0.5 N HCl, brine), dried (MgSO$_4$), filtered and concentrated under reduced pressure to afford the di-NHS ester product as a white solid (1.12 g, 68% yield).

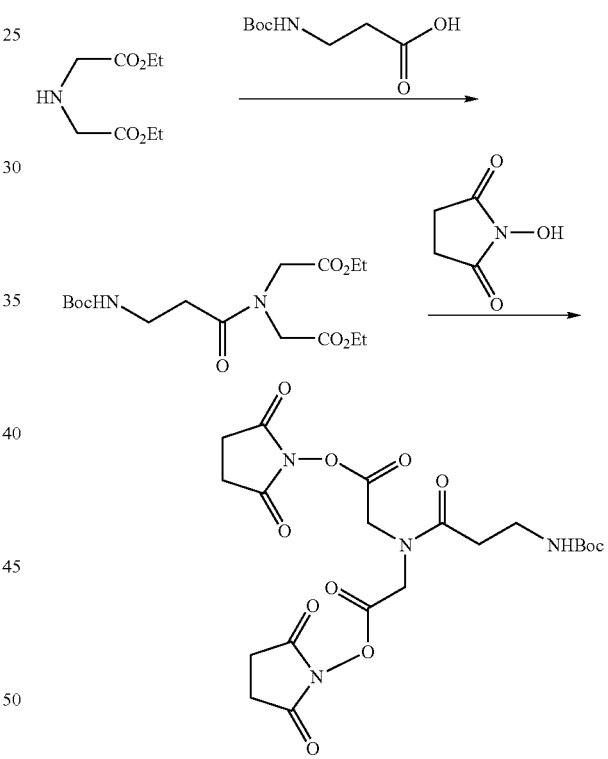

Step 3—Coupling of the Trifunctional Linker to the Peptide Monomers:

For coupling to the linker, 2 eq peptide is mixed with 1 eq of trifunctional linker in dry DMF to give a clear solution, and 5 eq of DIEA is added after 2 minutes. The mixture is stirred at ambient temperature for 14 h. The solvent is removed under reduced pressure and the crude product is dissolved in 80% TFA in DCM for 30 min to remove the Boc group, followed by purification with C18 reverse phase HPLC. The structure of the dimer is confirmed by electrospray mass spectrometry. This coupling reaction attaches the linker to the nitrogen atom of the ε-amino group of the lysine residue of each monomer. Coupling using SEQ ID NO: 1 is shown below.

(AcG)GLYACHMGPIT(1-nal)VCQPLRK—NH₂
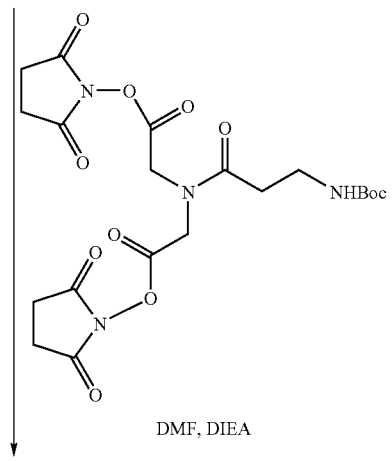
DMF, DIEA
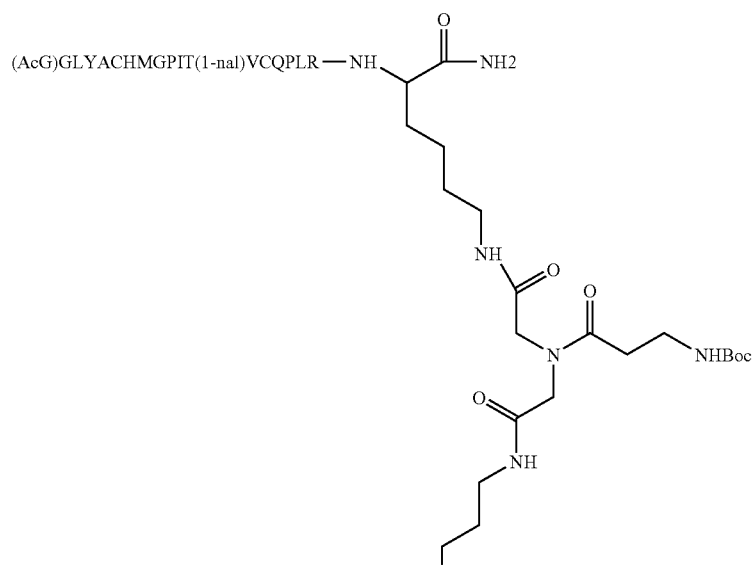
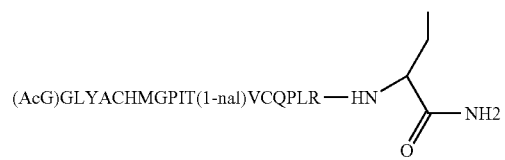
TFA -continued

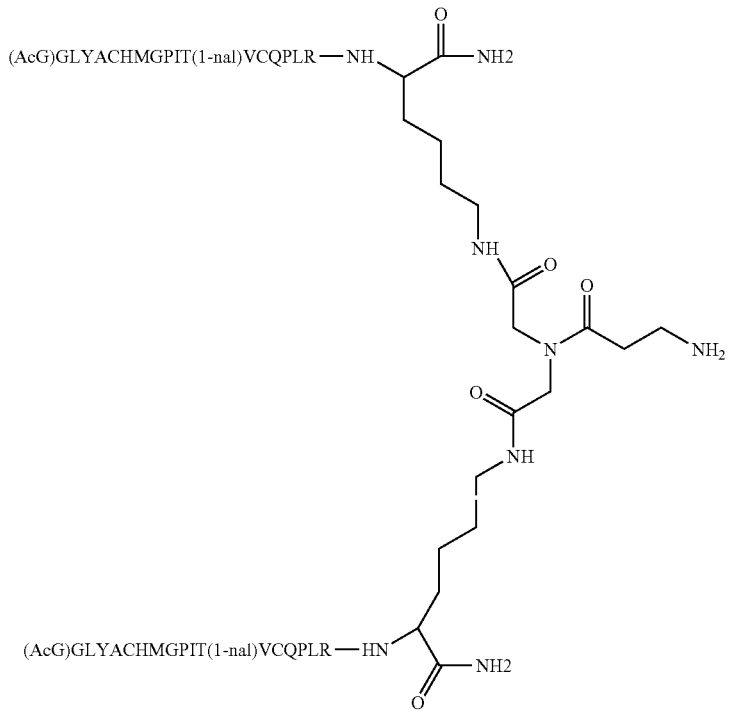

Step 4—Synthesis of PEG Moiety Comprising Two Linear PEGS Chains Linked By Lysine mPEG2-Lysinol-NPC Lysinol, which may be obtained commercially, is treated with an excess of mPEG2-NPC to obtain MPEG2-lysinol, which is then reacted with NPC to form mPEG2-lysinol-NPC.

mPEG2-Lys-NHS

This product may be obtained commercially, for example, from the Molecular Engineering catalog (2003) of Nektar Therapeutics (490 Discovery Drive, Huntsville, Ala. 35806), item no. 2Z3X0T01.

Step 5—PEGylation of the Peptide Dimer:

PEGylation Via a Carbamate Bond:

The peptide dimer and the PEG species (mPEG$_2$-Lysinol-NPC) are mixed in a 1:2 molar ratio in dry DMF to afford a clear solution. After 5 minutes 4 eq of DIEA is added to above solution. The mixture is stirred at ambient temperature 14 h, followed by purification with C18 reverse phase HPLC. The structure of PEGylated peptide is confirmed by MALDI mass. The purified peptide was also subjected to purification via cation ion exchange chromatography as outlined below. PEGylation using mPEG-Lysinol-NPC is shown below using SEQ ID NO: 1.

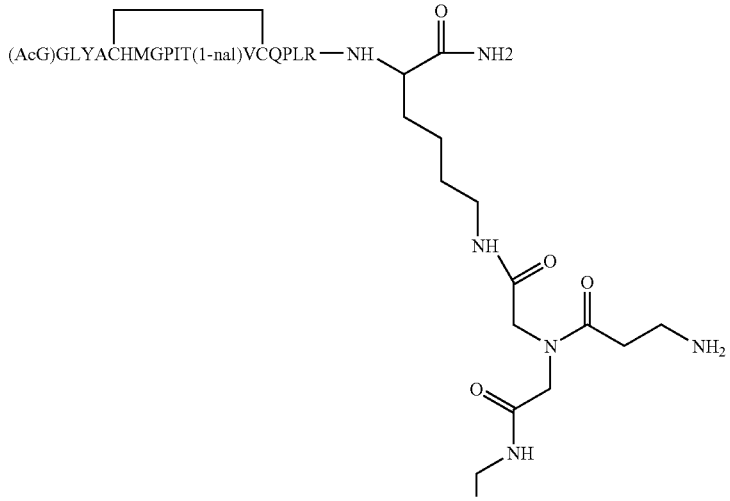

-continued

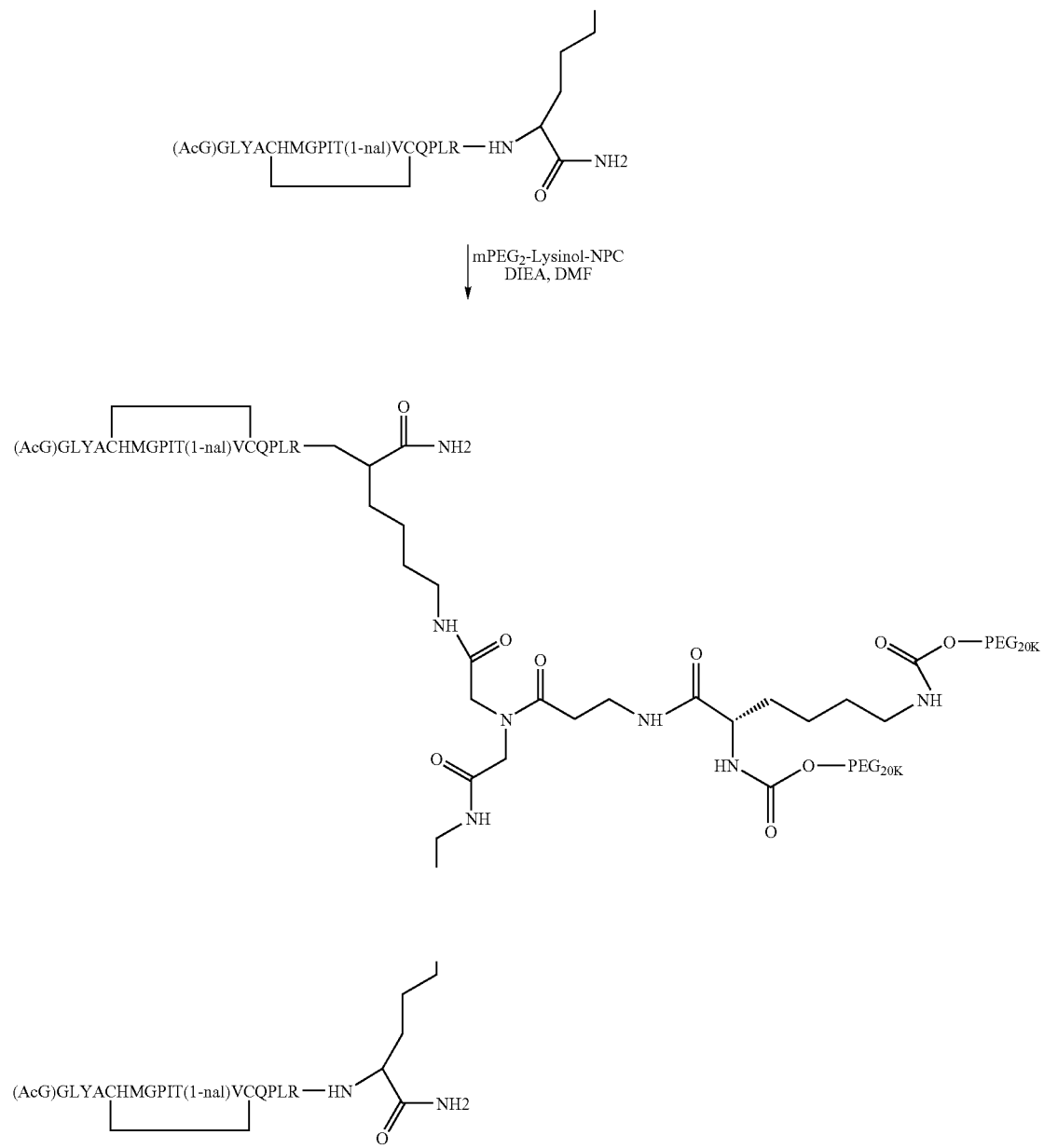

PEGylation Via an Amide Bond:

The peptide dimer and PEG species (mPEG$_2$-Lys-NHS from Shearwater Corp, USA) are mixed in a 1:2 molar ratio in dry DMF to afford a clear solution. After 5 minutes 10 eq of DIEA is added to above solution. The mixture is stirred at ambient temperature 2 h, followed by purification with C18 reverse phase HPLC. The structure of PEGylated peptide was confirmed by MALDI mass. The purified peptide was also subjected to purification via cation ion exchange chromatography as outlined below. PEGylation using mPEG$_2$-Lys-NHS using SEQ ID NO: 1 is shown below.

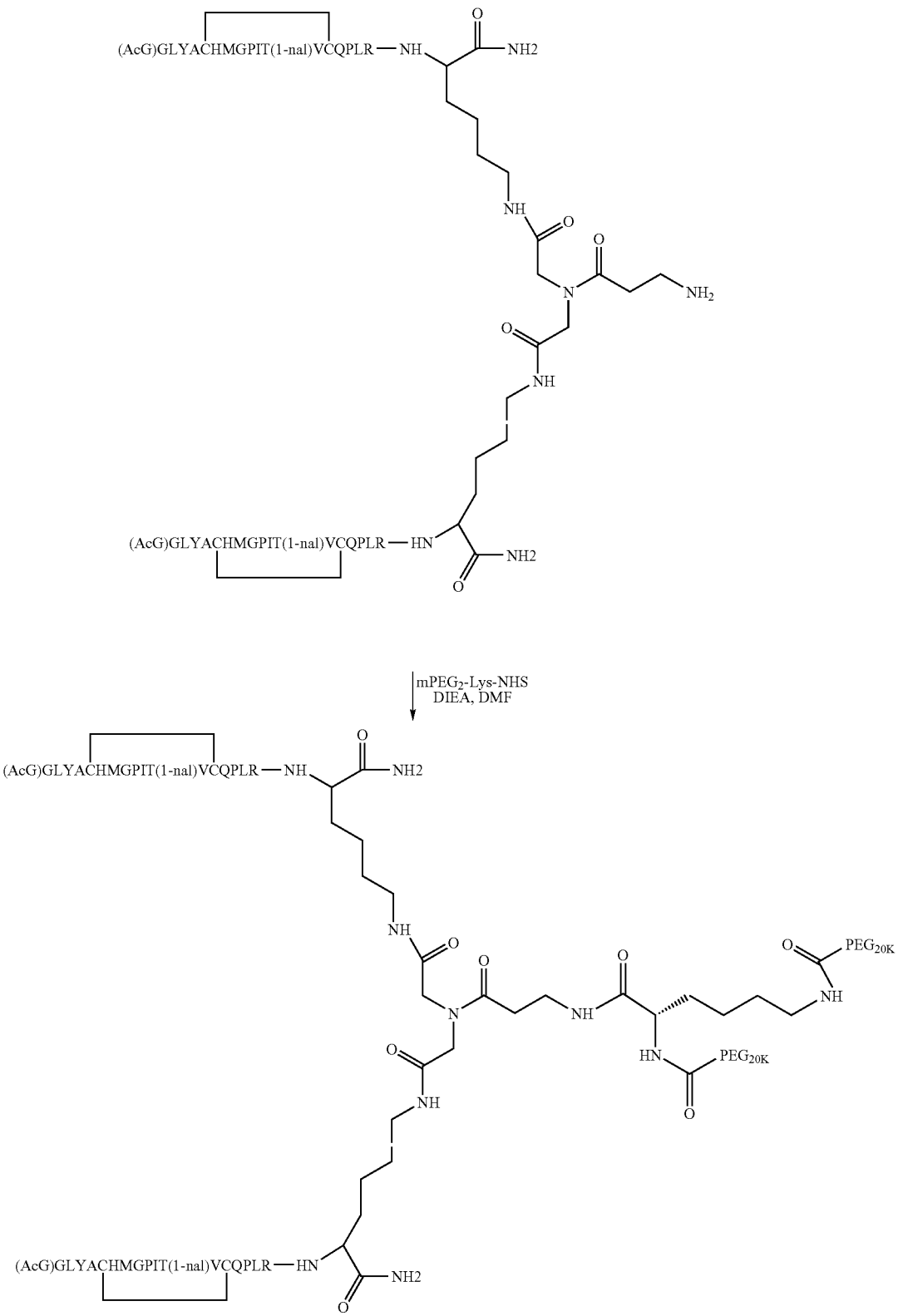
Step 6:—Ion exchange purification of peptides: Several exchange supports were surveyed for their ability to separate the above peptide-PEG conjugate from unreacted (or hydrolyzed) PEG, in addition to their ability to retain the starting dimeric peptides. The ion exchange resin (2–3 g) was loaded into a 1 cm column, followed by conversion to the sodium form (0.2 N NaOH loaded onto column until elutant was pH 14, ca. 5 column volumes), and than to the hydrogen form (eluted with either 0.1 N HCl or 0.1 M HOAc until elutant matched load pH, ca. 5 column volumes), followed by washing with 25% ACN/water until pH 6. Either the peptide prior to conjugation or the peptide-PEG conjugate was dissolved in 25% ACN/water (10 mg/mL) and the pH adjusted to <3 with TFA, then loaded on the column. After washing with 2–3 column volumes of 25% ACN/water and collecting 5 mL fractions, the peptide was released from the column by elution with 0.1 M $NH_4OAc$ in 25% ACN/water, again collecting 5 mL fractions. Analysis via HPLC revealed which fractions contained the desired peptide. Analysis with an Evaporative Light-Scattering Detector (ELSD) indicated that when the peptide was retained on the column and was eluted with the $NH_4OAc$ solution (generally between fractions 4 and 10), no non-conjugated PEG was observed as a contaminant. When the peptide eluted in the initial wash buffer (generally the first 2 fractions), no separation of desired PEG-conjugate and excess PEG was observed.

The following columns successfully retained both the peptide and the peptide-PEG conjugate, and successfully purified the peptide-PEG conjugate from the unconjugates peptide:

TABLE 5

| Ion Exhange Resins | |
|---|---|
| Support | Source |
| Mono S HR 5/5 strong cation exchange pre-loaded column | Amersham Biosciences |
| SE53 Cellulose, microgranular strong cation exchange support | Whatman |
| SP Sepharose Fast Flow strong cation exchange support | Amersham Biosciences |

Example 10

Synthesis of EPO-R Agonist Peptide Homodimers of Peptide Monomers Having the Amino Acid Sequence (AcG)GLYACHMGPIT(1-nal)VCQPLR(MeG)K (SEQ ID NO: 2)

EPO-R agonist peptide homodimers of peptide monomers having the amino acid sequence (AcG)GLYACHMGPIT(1-nal)VCQPLR(MeG)K (SEQ ID NO: 2) are synthesized as described in Example 1, except that in Step 1 the synthesized peptide monomers are:

(AcG)GLYACHMGPIT(1-nal)VCQPLR(MeG)K

Where the PEG is attached to the spacer via carbamate linkages, the final product of this synthesis using SEQ ID NO: 2 may by illustrated structurally as follows:

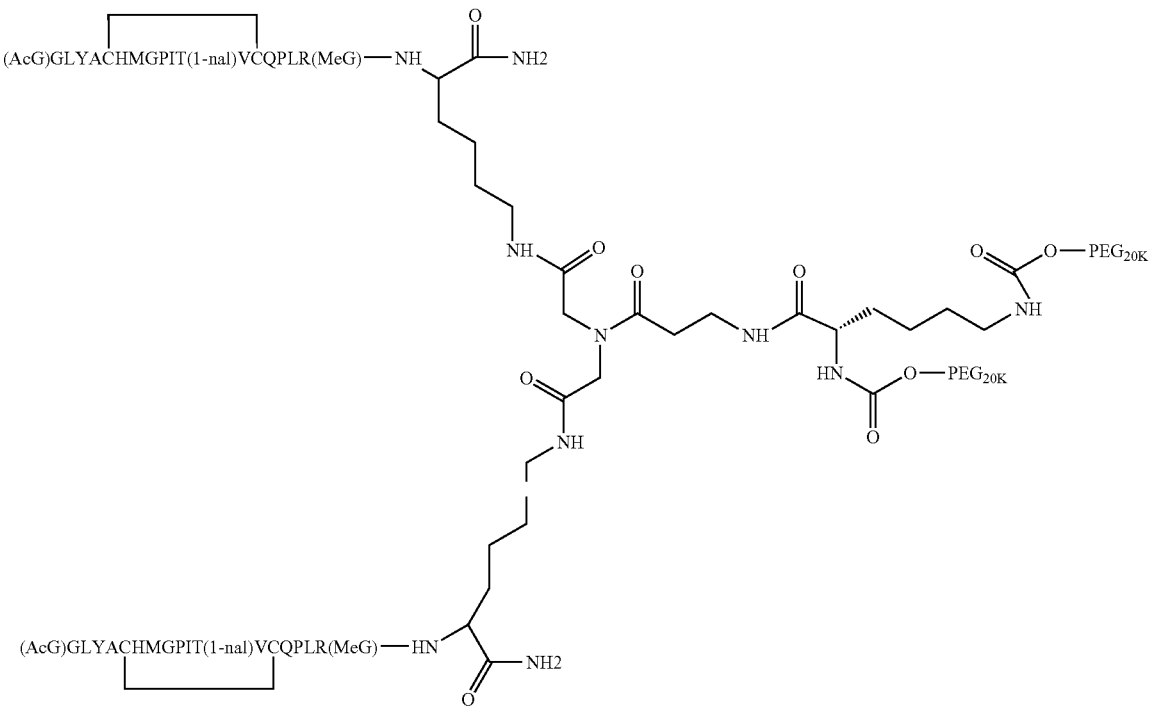

Where the PEG is attached to the spacer via amide linkages, the final product of this synthesis using SEQ ID NO: 2 may by illustrated structurally as follows:

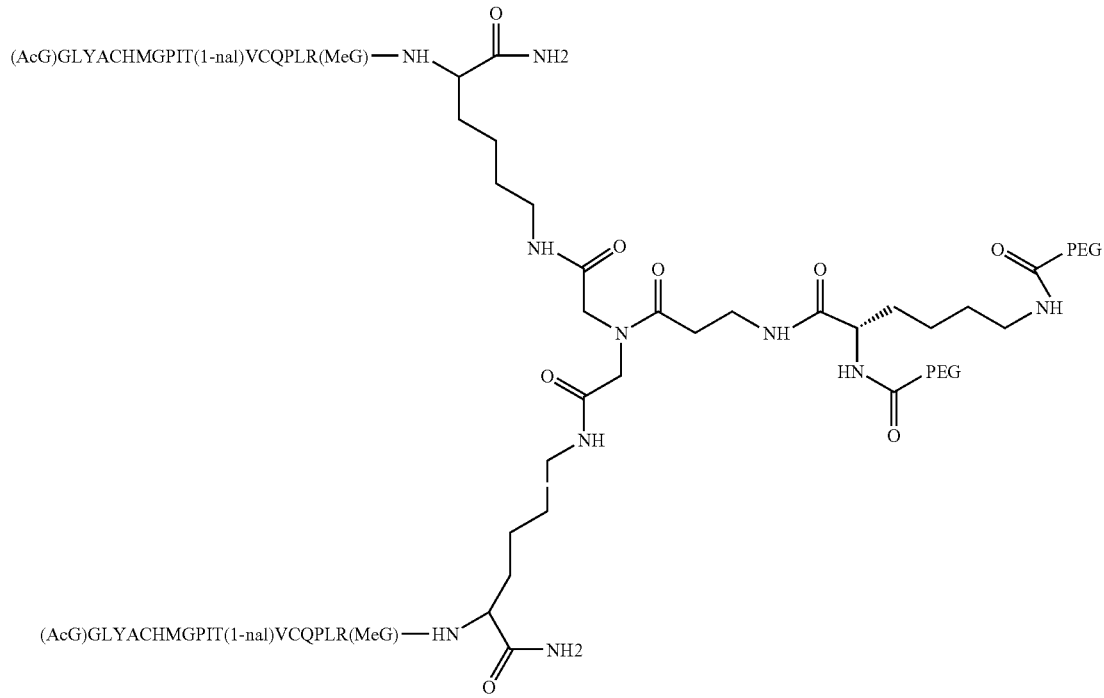

Example 11

In vitro Activity Assays

This example describes various in vitro assays that are useful in evaluating the activity and potency of EPO-R agonist peptides of the invention. The results for these assays demonstrate that the novel peptides of this invention bind to EPO-R and activate EPO-R signaling. Moreover, the results for these assays show that the novel peptide compositions exhibit a surprising increase in EPO-R binding affinity and biological activity compared to EPO mimetic peptides that have been previously described.

EPO-R agonist peptide monomers and dimers are prepared according to the methods provided in Example 1 or Example 2. The potency of these peptide dimers is evaluated using a series of in vitro activity assays, including: a reporter assay, a proliferation assay, a competitive binding assay, and a C/BFU-e assay. These four assays are described in further detail below.

The results of these in vitro activity assays are summarized in Table 2.

1. Reporter Assay

This assay is based upon a on a murine pre-B-cell lin derived reporter cell, Baf3/EpoR/GCSFR fos/lux. This reporter cell line expresses a chimeric receptor comprising the extra-cellular portion of the human EPO receptor to the intra-cellular portion of the human GCSF receptor. This cell line is further transfected with a fos promoter-driven luciferase reporter gene construct. Activation of this chimeric receptor through addition of erythropoietic agent results in the expression of the luciferase reporter gene, and therefore the production of light upon addition of the luciferase substrate luciferin. Thus, the level of EPO-R activation in such cells may be quantitated via measurement of luciferase activity.

The Baf3/EpoR/GCSFR fos/lux cells are cultured in DMEM/F12 medium (Gibco) supplemented with 10% fetal bovine serum (FBS; Hyclone), 10% WEHI-3 supernatant (the supernatant from a culture of WEHI-3 cells, ATCC # TIB-68), and penicillin/streptomycin. Approximately 18 h before the assay, cells are starved by transferring them to DMEM/F12 medium supplemented with 10% FBS and 0.1% WEHI-3 supernatant. On the day of assay, cells are washed once with DMEM/F12 medium supplemented with 10% FBS (no WEHI-3 supernatant), then $1 \times 10^6$ cells/mL are cultured in the presence of a known concentration of test peptide, or with EPO(R & D Systems Inc., Minneapolis, Minn.) as a positive control, in DMEM/F12 medium supplemented with 10% FBS (no WEHI-3 supernatant). Serial dilutions of the test peptide are concurrently tested in this assay. Assay plates are incubated for 4 h at 37° C. in a 5% $CO_2$ atmosphere, after which luciferin (Steady-Glo; Promega, Madison, Wis.) is added to each well. Following a 5-minute incubation, light emission is measured on a Packard Topcount Luminometer (Packard Instrument Co., Downers Grove, Ill.). Light counts are plotted relative to test peptide concentration and analysed using Graph Pad software. The concentration of test peptide that results in a half-maximal emission of light is recorded as the EC50.

2. Proliferation Assay

This assay is based upon a murine pre-B-cell line, Baf3, transfected to express human EPO-R. Proliferation of the resulting cell line, BaF3/Gal4/Elk/EPOR, is dependent on EPO-R activation. The degree of cell proliferation is quantitated using MTT, where the signal in the MTT assay is proportional to the number of viable cells.

The BaF3/Gal4/Elk/EPOR cells are cultured in spinner flasks in DMEM/F12 medium (Gibco) supplemented with 10% FBS (Hyclone) and 2% WEHI-3 supernatant (ATCC # TIB-68). Cultured cells are starved overnight, in a spinner flask at a cell density of 1×10⁶ cells/ml, in DMEM/F12 medium supplemented with 10% FBS and 0.1% WEHI-3 supernatant. The starved cells are then washed twice with Dulbecco's PBS (Gibco), and resuspended to a density of 1×10⁶ cells/ml in DMEM/F12 supplemented with 10% FBS (no WEHI-3 supernatant). 50 µL aliquots (~50,000 cells) of the cell suspension are then plated, in triplicate, in 96 well assay plates. 50 µL aliquots of dilution series of test EPO mimetic peptides, or 50 µL EPO(R & D Systems Inc., Minneapolis, Minn.) or Aranesp™ (darbepoeitin alpha, an ERO-R agonist commercially available from Amgen) in DMEM/F12 media supplemented with 10% FBS (no WEHI-3 supernatant 1) are added to the 96 well assay plates (final well volume of 100 µL). For example, 12 different dilutions may be tested where the final concentration of test peptide (or control EPO peptide) ranges from 810 pM to 0.0045 pM. The plated cells are then incubated for 48 h at 37° C. Next, 10 µL of MTT (Roche Diagnostics) is added to each culture dish well, and then allowed to incubate for 4 h. The reaction is then stopped by adding 10% SDS+0.01N HCl. The plates are then incubated overnight at 37° C. Absorbance of each well at a wavelength of 595 nm is then measured by spectrophotometry. Plots of the absorbance readings versus test peptide concentration are constructed and the EC50 calculated using Graph Pad software. The concentration of test peptide that results in a half-maximal absorbance is recorded as the EC50.

3. Competitive Binding Assay

Competitive binding calculations are made using an assay in which a light signal is generated as a function of the proximity of two beads: a streptavidin donor bead bearing a biotinylated EPO-R-binding peptide tracer and an acceptor bead to which is bound EPO-R. Light is generated by non-radiative energy transfer, during which a singlet oxygen is released from a first bead upon illumination, and contact with the released singlet oxygen causes the second bead to emit light. These bead sets are commercially available (Packard). Bead proximity is generated by the binding of the EPO-R-binding peptide tracer to the EPO-R. A test peptide that competes with the EPO-R-binding peptide tracer for binding to EPO-R will prevent this binding, causing a decrease in light emission.

In more detail the method is as follows: Add 4 µL of serial dilutions of the test EPO-R agonist peptide, or positive or negative controls, to wells of a 384 well plate. Thereafter, add 2 µL/well of receptor/bead cocktail. Receptor bead cocktail consists of: 15 µL of 5 mg/ml streptavidin donor beads (Packard), 15 µL of 5 mg/ml monoclonal antibody ab179 (this antibody recognizes the portion of the human placental alkaline phosphatase protein contained in the recombinant EPO-R), protein A-coated acceptor beads (protein A will bind to the ab179 antibody; Packard), 112.5 µL of a 1:6.6 dilution of recombinant EPO-R (produced in Chinese Hamster Ovary cells as a fusion protein to a portion of the human placental alkaline phosphatase protein which contains the ab179 target epitope) and 607.5 µL of Alphaquest buffer (40 mM HEPES, pH 7.4; 1 mM MgCl₂; 0.1% BSA, 0.05% Tween 20). Tap to mix. Add 2 µL/well of the biotinylated EPO-R-binding peptide tracer, (30 nM final concentration). The peptide tracer, an EPO-R binding peptide is made according to the methods described in Example 1, using SEQ ID NO: 4.

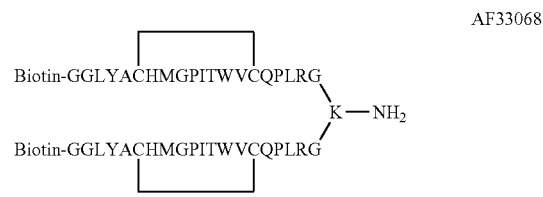

Centrifuge 1 min to mix. Seal plate with Packard Top Seal and wrap in foil. Incubate overnight at room temperature. After 18 hours read light emission using an AlphaQuest reader (Packard). Plot light emission vs concentration of peptide and analyse with Graph Pad or Excel.

The concentration of test peptide that results in a 50% decrease in light emission, relative to that observed without test peptide, is recorded as the IC50.

4. C/BFU-e Assay

EPO-R signaling stimulates the differentiation of bone marrow stem cells into proliferating red blood cell precursors. This assay measures the ability of test peptides to stimulate the proliferation and differentiation of red blood cell precursors from primary human bone marrow pluripotent stem cells.

For this assay, serial dilutions of test peptide are made in IMDM medium (Gibco) supplemented with 10% FBS (Hyclone). These serial dilutions, or positive control EPO peptide, are then added to methylcellulose to give a final volume of 1.5 mL. The methylcellulose and peptide mixture is then vortexed thoroughly. Aliquots (100,000 cells/mL) of human, bone marrow derived CD34+ cells (Poietics/Cambrex) are thawed. The thawed cells are gently added to 0.1 mL of 1 mg/ml DNAse (Stem Cells) in a 50 mL tube. Next, 40–50 mL IMDM medium is added gently to cells: the medium is added drop by drop along the side of the 50 mL tube for the first 10 mL, and then the remaining volume of medium is slowly dispensed along the side of the tube. The cells are then spun at 900 rpm for 20 min, and the media removed carefully by gentle aspiration. The cells are resuspended in 1 ml of IMDM medium and the cell density per mL is counted on hemacytometer slide (10 µL aliquot of cell suspension on slide, and cell density is the average count ×10,000 cells/ml). The cells are then diluted in IMDM medium to a cell density of 15,000 cells/mL. A 100 µL of diluted cells is then added to each 1.5 mL methyl cellulose plus peptide sample (final cell concentration in assay media is 1000 cells/mL), and the mixture is vortexed. Allow the bubbles in the mixture to disappear, and then aspirate 1 mL using blunt-end needle. Add 0.25 mL aspirated mixture from each sample into each of 4 wells of a 24-well plate (Falcon brand). Incubate the plated mixtures at 37° C. under 5% CO₂ in a humid incubator for 14 days. Score for the presence of erythroid colonies using a phase microscope (5×–10× objective, final magnification of 100×). The concentration of test peptide at which the number of formed colonies is 90% of maximum, relative to that observed with the EPO positive control, is recorded as the EC90 [See Table 2: C/BFU-e EC90].

TABLE 6

In vitro activity assays for peptide dimers

| Compound designation | Peptide dimer | Reporter EC50 (pM) |
|---|---|---|
| AF37702 | (AcG)GLYACHMGPIT(1-nal)VCQPLR(MEG)—NH—C(O)—NH2 ... cross-linked dimer with second chain (AcG)GLYACHMGPIT(1-nal)VCQPLR(MEG)—HN—, bearing two O-PEG$_{20K}$ groups | 195 |

| Compound designation | Proliferation EC50 (pM) | Radioligand IC50 (pM) | C/BFU-e EC90 (nM) |
|---|---|---|---|
| AF37702 | 165 | 111 | 3 |

Example 12

In Vivo Activity Assays

This example describes various in vivo assays that are useful in evaluating the activity and potency of EPO-R agonist peptides of the invention. EPO-R agonist peptide monomers and dimers are prepared according to the methods provided in Example 1. The in vivo activity of these peptide monomers and dimers is evaluated using a series assays, including a polycythemic exhypoxic mouse bioassay and a reticulocyte assay. These two assays are described in further detail below.

1. Polycythemic Exhypoxic Mouse Bioassay

Test peptides are assayed for in vivo activity in the polycythemic exhypoxic mouse bioassay adapted from the method described by Cotes and Bangham (1961), Nature 191: 1065–1067. This assay examines the ability of a test peptide to function as an EPO mimetic: i.e., to activate EPO-R and induce new red blood cell synthesis. Red blood cell synthesis is quantitated based upon incorporation of radiolabeled iron into hemoglobin of the synthesized red blood cells.

BDF1 mice are allowed to acclimate to ambient conditions for 7–10 days. Body weights are determined for all animals, and low weight animals (<15 grams) are not used. Mice are subjected to successive conditioning cycles in a hypobaric chamber for a total of 14 days. Each 24 hour cycle consists of 18 hr at 0.40±0.02% atmospheric pressure and 6 hr at ambient pressure. After conditioning the mice are maintained at ambient pressure for an additional 72 hr prior to dosing.

Test peptides, or recombinant human EPO standards, are diluted in PBS+0.1% BSA vehicle (PBS/BSA). Peptide monomer stock solutions are first solubilized in dimethyl sulfoxide (DMSO). Negative control groups include one group of mice injected with PBS/BSA alone, and one group injected with 1% DMSO. Each dose group contains 10 mice. Mice are injected subcutaneously (scruff of neck) with 0.5 mL of the appropriate sample.

Forty eight hours following sample injection, the mice are administered an intraperitoneal injection of 0.2 ml of $Fe^{59}$ (Dupont, NEN), for a dose of approximately 0.75 µCuries/mouse. Mouse body weights are determined 24 hr after $Fe^{59}$ administration, and the mice are sacrificed 48 hr after $Fe^{59}$ administration. Blood is collected from each animal by cardiac puncture and hematocrits are determined (heparin was used as the anticoagulant). Each blood sample (0.2 ml) is analyzed for $Fe^{59}$ incorporation using a Packard gamma counter. Non-responder mice (i.e., those mice with radioactive incorporation less than the negative control group) are eliminated from the appropriate data set. Mice that have hematocrit values less than 53% of the negative control group are also eliminated.

Results are derived from sets of 10 animals for each experimental dose. The average amount of radioactivity incorporated [counts per minute (CPM)] into blood samples from each group is calculated.

2. Reticulocyte Assay

Normal BDF1 mice are dosed (0.5 mL, injected subcutaneously) on three consecutive days with either EPO control or test peptide. At day three, mice are also dosed (0.1 mL, injected intraperitoneally) with iron dextran (100 mg/ml). At day five, mice are anesthetized with $CO_2$ and bled by cardiac puncture. The percent (%) reticulocytes for each blood sample is determined by thiazole orange staining and flow cytometer analysis (retic-count program). Hematocrits are manually determined. The corrected percent of reticulocytes is determined using the following formula:

$$\% \text{ RETIC}_{CORRECTED} = \% \text{ RETIC}_{OBSERVED} \times (\text{Hematocrit}_{INDIVIDUAL}/\text{Hematocrit}_{NORMAL})$$

3. Hematological Assay

Normal CD1 mice are dosed with four weekly bolus intravenous injections of either EPO positive control, test peptide, or vehicle. A range of positive control and test peptide doses, expressed as mg/kg, are tested by varying the active compound concentration in the formulation. Volumes injected are 5 ml/kg. The vehicle control group is comprised twelve animals, while 8 animals are in each of the remaining dose groups. Daily viability and weekly body weights are recorded.

The dosed mice are mice are fasted and then anesthetized with inhaled isoflurane and terminal blood samples are collected via cardiac or abdominal aorta puncture on Day 1 (for vehicle control mice) and on Days 15 and 29 (4 mice/group/day). The blood is transferred to Vacutainer® brand tubes. Preferred anticoagulant is ethylenediaminetetraacetic acid (EDTA).

Blood samples are evaluated for endpoints measuring red blood synthesis and physiology such as hematocrit (Hct), hemoglobin (Hgb) and total erythrocyte count (RBC) using automated clinical analyzers well known in the art (e.g., those made by Coulter, Inc.).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Numerous references, including patents, patent applications, and various publications are cited and discussed in the description of this invention. The citation and/or discussion of such references is provided merely to clarify the description of the present invention and is not an admission that any such reference is "prior art" to the present invention. All references cited and discussed in this specification are incorporated herein by reference in their entirety and to the same extent as if each reference was individually incorporated by reference.

What is claimed is:

1. A compound that binds to and activates the erythropoietin receptor (EPO-R), which compound comprises a peptide dimer having the formula:

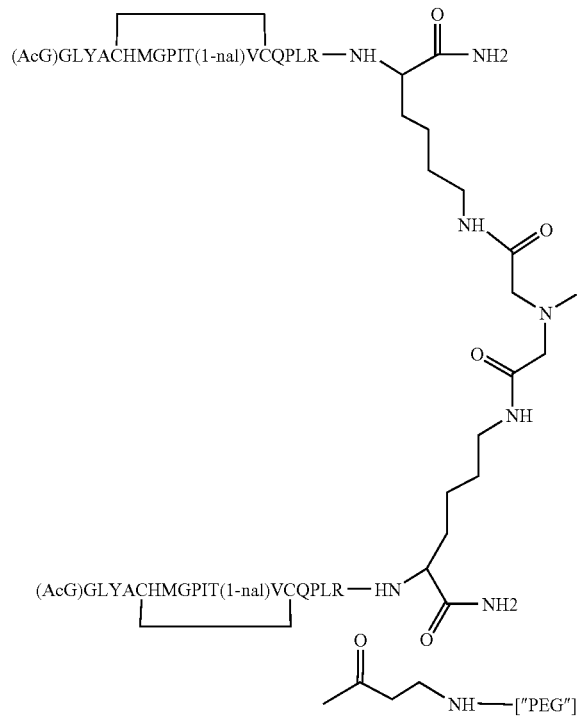

wherein
(i) in each peptide monomer of the peptide dimer, each amino acid is indicated by standard one letter abbreviation, AcG is N-acetylglycine, and 1-nal is 1-naphthylalanine;

(ii) each peptide monomer of the peptide dimer contains an intramolecular disulfide bond between the two cysteine (C) residues of each monomer (iii) ["PEG"] comprises at least one linear polyethylene glycol (PEG) moiety, each PEG moiety having a molecular weight of about 20,000 to about 40,000 Daltons.

2. A compound according to claim 1, wherein each PEG has a molecular weight of about 30,000 Daltons.

3. A method for treating a patient having a disorder characterized by a deficiency of erythropoietin or a low or defective red blood cell population, which method comprises administering to the patient a therapeutically effective amount of the compound of claim 1.

4. A method according to claim 3 wherein the disorder is selected from the group consisting of end stage renal failure or dialysis; anemia associated with AIDS, auto immune disease or a malignancy; beta-thalassemia; cystic fibrosis; early anemia of prematurity; anemia associated with chronic inflammatory disease; spinal cord injury; acute blood loss; aging; and neoplastic disease states accompanied by abnormal erythropoiesis.

5. A method according to claim 3, wherein each PEG has a molecular weight of about 30,000 Daltons.

6. A pharmaceutical composition comprising the compound of claim 1 and a pharmaceutically acceptable carrier.

7. A pharmaceutical composition according to claim 6, wherein each PEG has a molecular weight of about 30,000 Daltons.

8. A compound that binds to and activates the erythropoietin receptor (EPO-R), which compound comprises a peptide dimer having the formula:

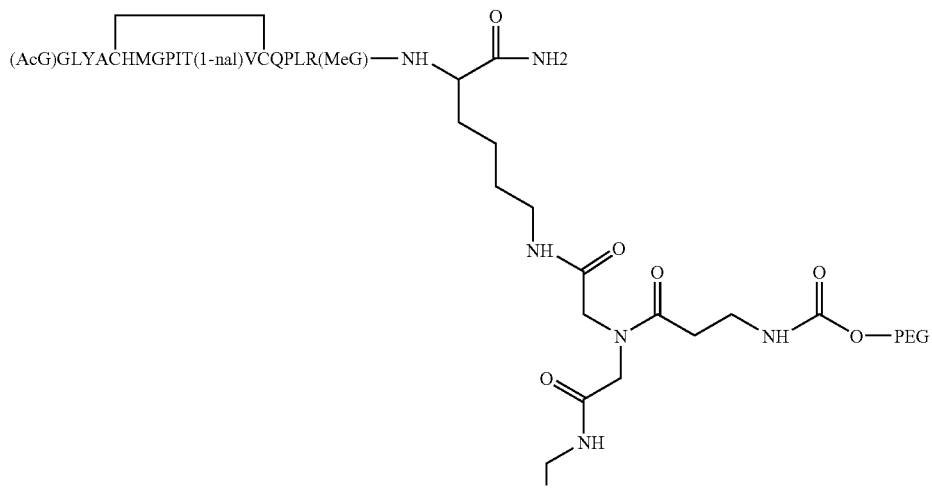

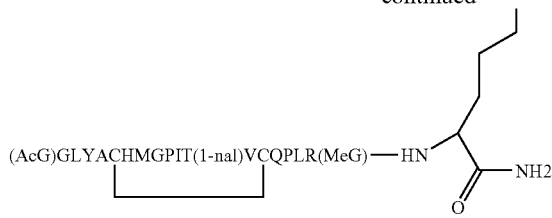

where
- (i) in each peptide monomer of the peptide dimer, each amino acid is indicated by standard one letter abbreviation, AcG is N-acetylglycine, 1-nal is 1-naphthylalanine, and MeG is N-methylglycine;
- (ii) each peptide monomer of the peptide dimer contains an intramolecular disulfide bond between the two cysteine (C) residues of each monomer
- (iii) PEG comprises a linear unbranched polyethylene glycol molecule having a molecular weight of about 20,000 to about 40,000 Daltons.

9. A compound according to claim 8, wherein the PEG has a molecular weight of about 30,000 Daltons.

10. A method for treating a patient having a disorder characterized by a deficiency of erythropoietin or a low or defective red blood cell population, which method comprises administering to the patient a therapeutically effective amount of the compound of claim 8.

11. A method according to claim 10 wherein the disorder is selected from the group consisting of end stage renal failure or dialysis; anemia associated with AIDS, auto immune disease or a malignancy; beta-thalassemia; cystic fibrosis; early anemia of prematurity; anemia associated with chronic inflammatory disease; spinal cord injury; acute blood loss; aging; and neoplastic disease states accompanied by abnormal erythropoiesis.

12. A method according to claim 10, wherein the PEG has a molecular weight of about 30,000 Daltons.

13. A pharmaceutical composition comprising the compound of claim 8 and a pharmaceutically acceptable carrier.

14. A pharmaceutical composition according to claim 13, wherein the PEG has a molecular weight of about 30,000 Daltons.

15. A compound that binds to and activates the erythropoietin receptor (EPO-R), which compound comprises a peptide dimer having the formula:

where
- (i) in each peptide monomer of the peptide dimer, each amino acid is indicated by standard one letter abbreviation, AcG is N-acetylglycine, and 1-nal is 1-naphthylalanine;
- (ii) each peptide monomer of the peptide dimer contains an intramolecular disulfide bond between the two cysteine (C) residues of each monomer (iii) PEG comprises a linear unbranched polyethylene glycol molecule having a molecular weight of about 20,000 to about 40,000 Daltons.

16. A compound according to claim 15, wherein the PEG has a molecular weight of about 30,000 Daltons.

17. A method for treating a patient having a disorder characterized by a deficiency of erythropoietin or a low or defective red blood cell population, which method comprises administering to the patient a therapeutically effective amount of the compound of claim 15.

18. A method according to claim 17 wherein the disorder is selected from the group consisting of end stage renal failure or dialysis; anemia associated with AIDS, auto immune disease or a malignancy; beta-thalassemia; cystic fibrosis; early anemia of prematurity; anemia associated with chronic inflammatory disease; spinal cord injury; acute blood loss; aging; and neoplastic disease states accompanied by abnormal erythropoiesis.

19. A method according to claim 17, wherein the PEG has a molecular weight of about 30,000 Daltons.

20. A pharmaceutical composition comprising the compound of claim 15 and a pharmaceutically acceptable carrier.

21. A pharmaceutical composition according to claim 20, wherein the PEG has a molecular weight of about 30,000 Daltons.

22. A compound that binds to and activates the erythropoietin receptor (EPO-R), which compound comprises a peptide dimer having the formula:

(ii) each peptide monomer of the peptide dimer contains an intramolecular disulfide bond between the two cysteine (C) residues of each monomer (iii) PEG comprises a linear unbranched polyethylene glycol molecule having a molecular weight of about 20,000 to about 40,000 Daltons.

23. A compound according to claim 22, wherein the PEG has a molecular weight of about 30,000 Daltons.

24. A method for treating a patient having a disorder characterized by a deficiency of erythropoietin or a low or defective red blood cell population, which method comprises administering to the patient a therapeutically effective amount of the compound of claim 22.

25. A method according to claim 24 wherein the disorder is selected from the group consisting of end stage renal failure or dialysis; anemia associated with AIDS, auto immune disease or a malignancy; beta-thalassemia; cystic fibrosis; early anemia of prematurity; anemia associated with chronic inflammatory disease; spinal cord injury; acute blood loss; aging; and neoplastic disease states accompanied by abnormal erythropoiesis.

26. A method according to claim 24, wherein the PEG has a molecular weight of about 30,000 Daltons.

27. A pharmaceutical composition comprising the compound of claim 22 and a pharmaceutically acceptable carrier.

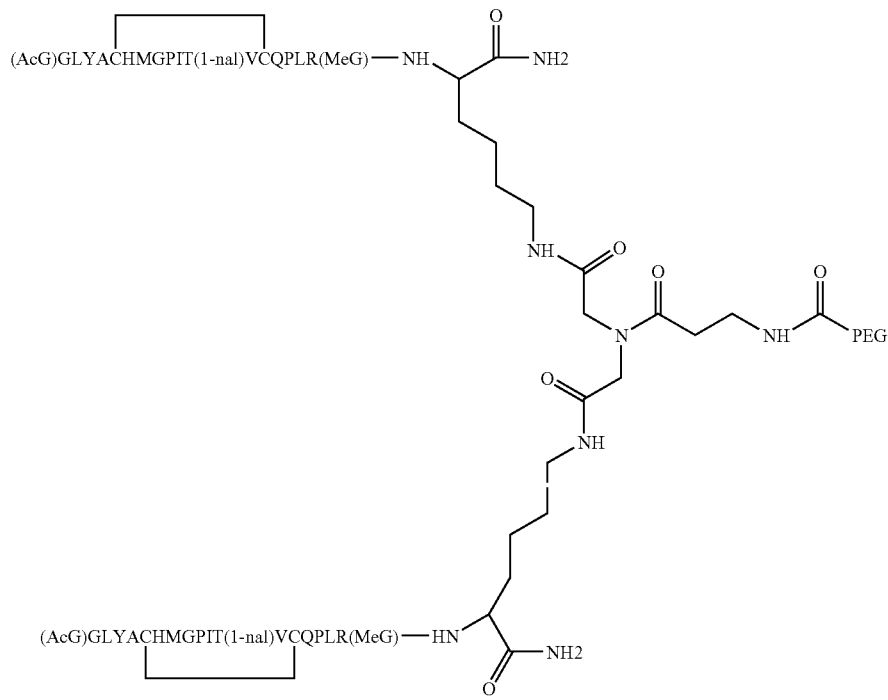

where
(i) in each peptide monomer of the peptide dimer, each amino acid is indicated by standard one letter abbreviation, AcG is N-acetylglycine, 1-nal is 1-naphthylalanine, and MeG is N-methylglycine;

28. A pharmaceutical composition according to claim 27, wherein the PEG has a molecular weight of about 30,000 Daltons.

29. A compound that binds to and activates the erythropoietin receptor (EPO-R), which compound comprises a peptide dimer having the formula:

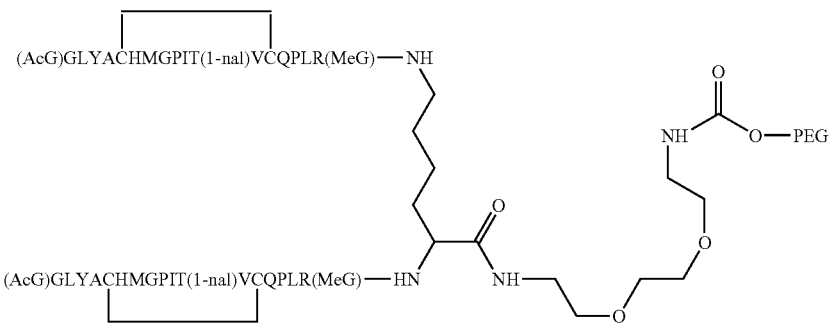

where
(i) in each peptide monomer of the peptide dimer, each amino acid is indicated by standard one letter abbreviation, AcG is N-acetylglycine, 1-nal is 1-naphthylalanine, and MeG is N-methylglycine;
(ii) each peptide monomer of the peptide dimer contains an intramolecular disulfide bond between the two cysteine (C) residues of each monomer
(iii) PEG comprises a linear unbranched polyethylene glycol molecule having a molecular weight of about 20,000 to about 40,000 Daltons.

30. A compound according to claim 29, wherein the PEG has a molecular weight of about 30,000 Daltons.

31. A method for treating a patient having a disorder characterized by a deficiency of erythropoietin or a low or defective red blood cell population, which method comprises administering to the patient a therapeutically effective amount of the compound of claim 29.

32. A method according to claim 31 wherein the disorder is selected from the group consisting of end stage renal failure or dialysis; anemia associated with AIDS, auto immune disease or a malignancy; beta-thalassemia; cystic fibrosis; early anemia of prematurity; anemia associated with chronic inflammatory disease; spinal cord injury; acute blood loss; aging; and neoplastic disease states accompanied by abnormal erythropoiesis.

33. A method according to claim 31, wherein the PEG has a molecular weight of about 30,000 Daltons.

34. A pharmaceutical composition comprising the compound of claim 29 and a pharmaceutically acceptable carrier.

35. A pharmaceutical composition according to claim 34, wherein the PEG has a molecular weight of about 30,000 Daltons.

36. A compound that binds to and activates the erythropoietin receptor (EPO-R), which compound comprises a peptide dimer having the formula:

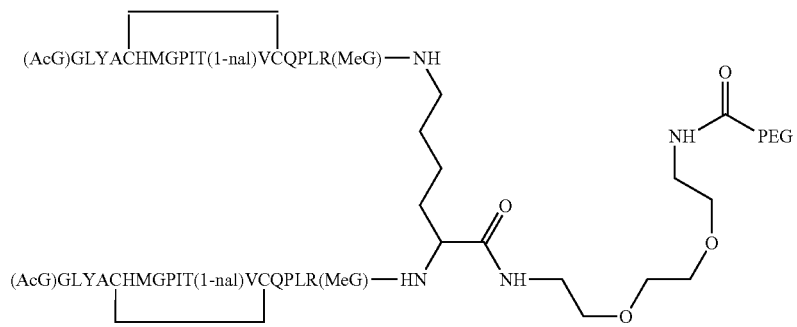

where
(i) in each peptide monomer of the peptide dimer, each amino acid is indicated by standard one letter abbreviation, AcG is N-acetylglycine, 1-nal is 1-naphthylalanine, and MeG is N-methylglycine;
(ii) each peptide monomer of the peptide dimer contains an intramolecular disulfide bond between the two cysteine (C) residues of each monomer
(iii) PEG comprises a linear unbranched polyethylene glycol molecule having a molecular weight of about 20,000 to about 40,000 Daltons.

37. A compound according to claim 36, wherein the PEG has a molecular weight of about 20,000 Daltons.

38. A method for treating a patient having a disorder characterized by a deficiency of erythropoietin or a low or defective red blood cell population, which method comprises administering to the patient a therapeutically effective amount of the compound of claim 36.

39. A method according to claim 38 wherein the disorder is selected from the group consisting of end stage renal failure or dialysis; anemia associated with AIDS, auto immune disease or a malignancy; beta-thalassemia; cystic fibrosis; early anemia of prematurity; anemia associated with chronic inflammatory disease; spinal cord injury; acute blood loss; aging; and neoplastic disease states accompanied by abnormal erythropoiesis.

40. A method according to claim 38, wherein the PEG has a molecular weight of about 20,000 Daltons.

41. A pharmaceutical composition comprising the compound of claim 36 and a pharmaceutically acceptable carrier.

42. A pharmaceutical composition according to claim 41, wherein the PEG has a molecular weight of about 20,000 Daltons.

43. A compound that binds to and activates the erythropoietin receptor (EPO-R), which compound comprises a peptide dimer having the formula:

44. A compound according to claim 43, wherein each PEG has a molecular weight of about 20,000 Daltons.

45. A method for treating a patient having a disorder characterized by a deficiency of erythropoietin or a low or defective red blood cell population, which method comprises administering to the patient a therapeutically effective amount of the compound of claim 43.

46. A method according to claim 45 wherein the disorder is selected from the group consisting of end stage renal failure or dialysis; anemia associated with AIDS, auto immune disease or a malignancy; beta-thalassemia; cystic fibrosis; early anemia of prematurity; anemia associated

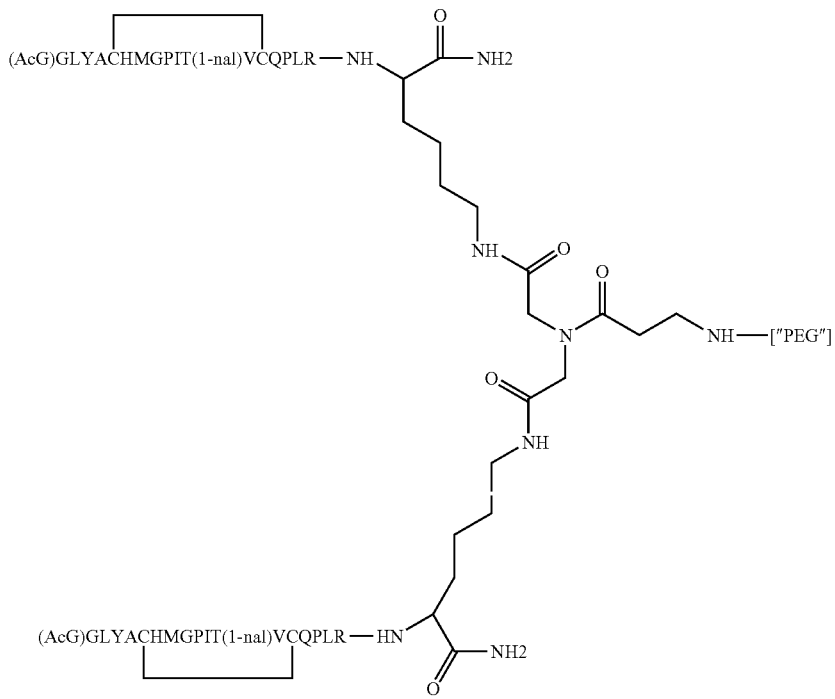

wherein
(i) in each peptide monomer of the peptide dimer, each amino acid is indicated by standard one letter abbreviation, AcG is N-acetylglycine, and 1-nal is 1-naphthylalanine;

(ii) each peptide monomer of the peptide dimer contains an intramolecular disulfide bond between the two cysteine (C) residues of each monomer (iii) ["PEG"] comprises at least two linear polyethylene glycol (PEG) moieties linked at a single point of attachment and having a combined molecular weight of about 10,000 to about 60,000 Daltons.

with chronic inflammatory disease; spinal cord injury; acute blood loss; aging; and neoplastic disease states accompanied by abnormal erythropoiesis.

47. A method according to claim 45, wherein each PEG has a molecular weight of about 20,000 Daltons.

48. A pharmaceutical composition comprising the compound of claim 43 and a pharmaceutically acceptable carrier.

49. A pharmaceutical composition according to claim 48, wherein each PEG has a molecular weight of about 20,000 Daltons.

50. A compound that binds to and activates the erythropoietin receptor (EPO-R), which compound comprises a peptide dimer having the formula:

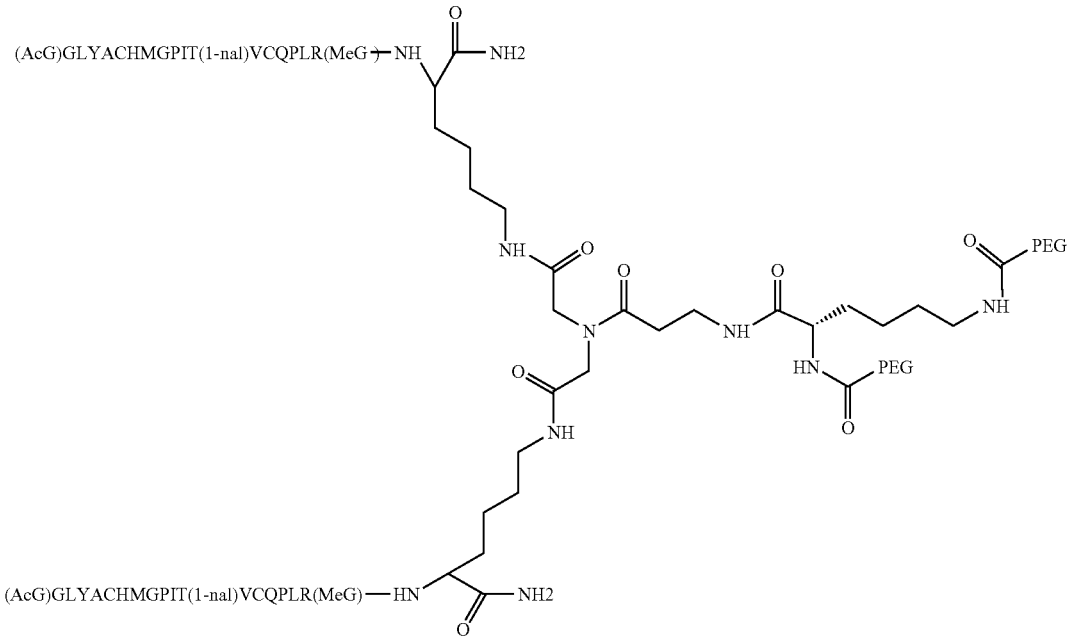

where
- (i) in each peptide monomer of the peptide dimer, each amino acid is indicated by standard one letter abbreviation, AcG is N-acetylglycine, 1-nal is 1-naphthylalanine, and MeG is N-methylglycine;
- (ii) each peptide monomer of the peptide dimer contains an intramolecular disulfide bond between the two cysteine (C) residues of each monomer
- (iii) PEG comprises two linear polyethylene glycol (PEG) moieties having a combined molecular weight of about 10,000 to about 30,000 Daltons.

51. A compound according to claim 50, wherein each PEG has a molecular weight of about 20,000 Daltons.

52. A method for treating a patient having a disorder characterized by a deficiency of erythropoietin or a low or defective red blood cell population, which method comprises administering to the patient a therapeutically effective amount of the compound of claim 50.

53. A method according to claim 52 wherein the disorder is selected from the group consisting of end stage renal failure or dialysis; anemia associated with AIDS, auto immune disease or a malignancy; beta-thalassemia; cystic fibrosis; early anemia of prematurity; anemia associated with chronic inflammatory disease; spinal cord injury; acute blood loss; aging; and neoplastic disease states accompanied by abnormal erythropoiesis.

54. A method according to claim 52, wherein each PEG has a molecular weight of about 20,000 Daltons.

55. A pharmaceutical composition comprising the compound of claim 50 and a pharmaceutically acceptable carrier.

56. A pharmaceutical composition according to claim 55, wherein each PEG has a molecular weight of about 20,000 Daltons.

57. A compound that binds to and activates the erythropoietin receptor (EPO-R), which compound comprises a peptide dimer having the formula:

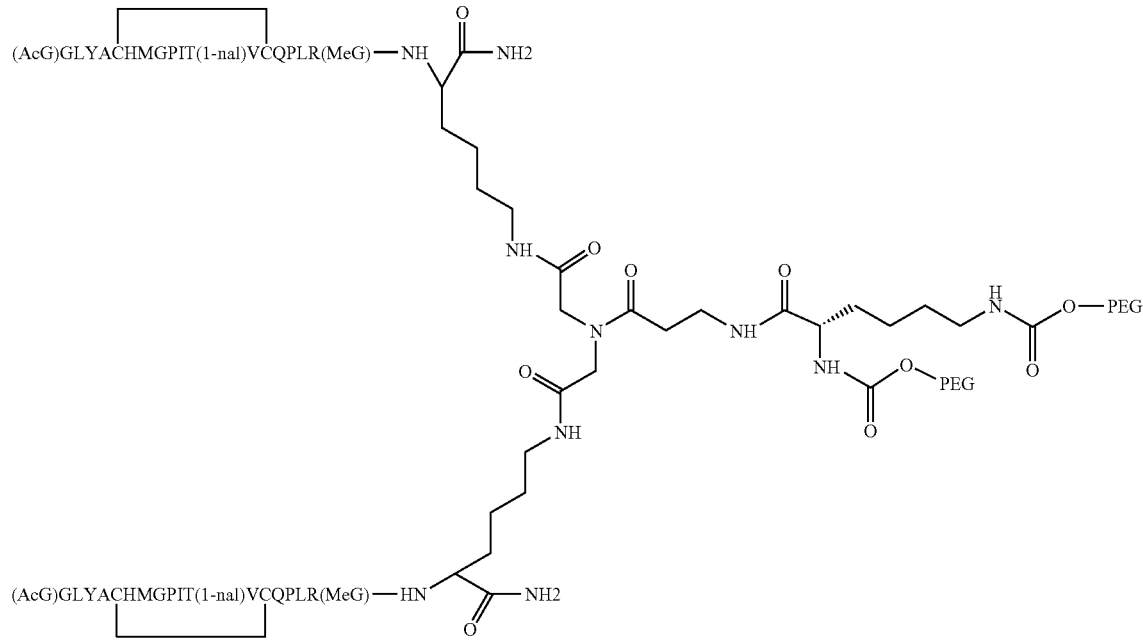

wherein
- (i) in each peptide monomer of the peptide dimer, each amino acid is indicated by standard one letter abbreviation, AcG is N-acetylglycine, and 1-nal is 1-naphthylalanine;
- (ii) each peptide monomer of the peptide dimer contains an intramolecular disulfide bond between the two cysteine (C) residues of each monomer
- (iii) PEG comprises two linear polyethylene glycol (PEG) moieties having a combined molecular weight of about 10,000 to about 30,000 Daltons.

58. A compound according to claim 57, wherein the PEG has a molecular weight of about 20,000 Daltons.

59. A method for treating a patient having a disorder characterized by a deficiency of erythropoietin or a low or defective red blood cell population, which method comprises administering to the patient a therapeutically effective amount of the compound of claim 57.

60. A method according to claim 59 wherein the disorder is selected from the group consisting of end stage renal failure or dialysis; anemia associated with AIDS, auto immune disease or a malignancy; beta-thalassemia; cystic fibrosis; early anemia of prematurity; anemia associated with chronic inflammatory disease; spinal cord injury; acute blood loss; aging; and neoplastic disease states accompanied by abnormal erythropoiesis.

61. A method according to claim 59, wherein each PEG has a molecular weight of about 20,000 Daltons.

62. A pharmaceutical composition comprising the compound of claim 57 and a pharmaceutically acceptable carrier.

63. A pharmaceutical composition according to claim 62, wherein each PEG has a molecular weight of about 20,000 Daltons.

64. A compound that binds to and activates the erythropoietin receptor (EPO-R), which compound comprises a peptide dimer having the formula:

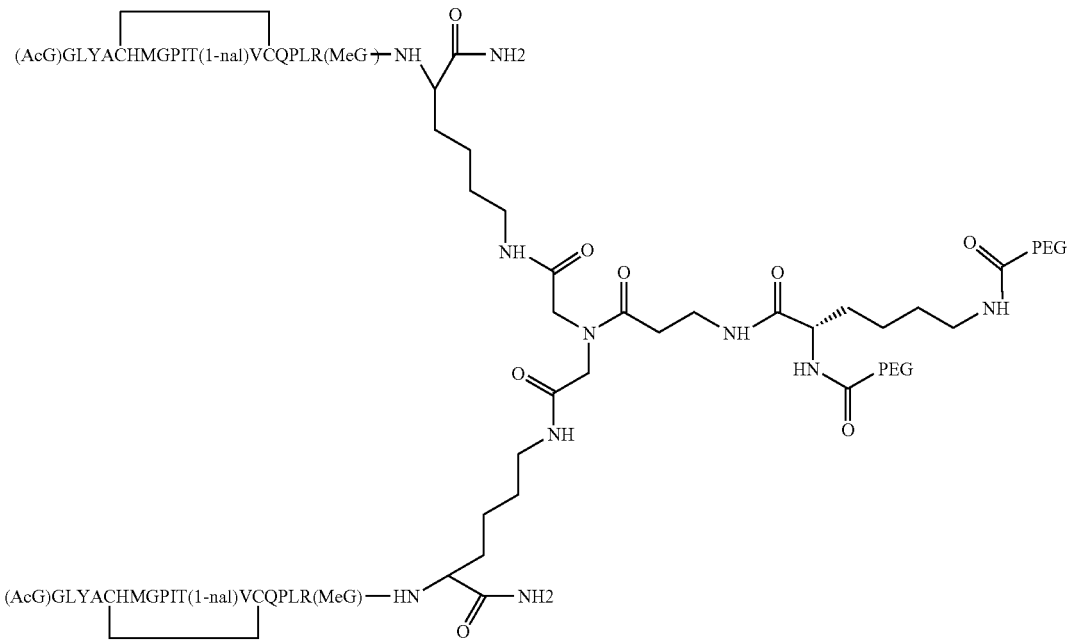

wherein
  (i) in each peptide monomer of the peptide dimer, each amino acid is indicated by standard one letter abbreviation, AcG is N-acetylglycine, 1-nal is 1-naphthylalanine, and MeG is N-methylglycine;
  (ii) each peptide monomer of the peptide dimer contains an intramolecular disulfide bond between the two cysteine (C) residues of each monomer
  (iii) PEG comprises two linear polyethylene glycol (PEG) moieties having a combined molecular weight of about 10,000 to about 30,000 Daltons.

65. A compound according to claim 64, wherein each PEG has a molecular weight of about 20,000 Daltons.

66. A method for treating a patient having a disorder characterized by a deficiency of erythropoietin or a low or defective red blood cell population, which method comprises administering to the patient a therapeutically effective amount of the compound of claim 64.

67. A method according to claim 66 wherein the disorder is selected from the group consisting of end stage renal failure or dialysis; anemia associated with AIDS, auto immune disease or a malignancy; beta-thalassemia; cystic fibrosis; early anemia of prematurity; anemia associated with chronic inflammatory disease; spinal cord injury; acute blood loss; aging; and neoplastic disease states accompanied by abnormal erythropoiesis.

68. A method according to claim 66, wherein each PEG has a molecular weight of about 20,000 Daltons.

69. A pharmaceutical composition comprising the compound of claim 64 and a pharmaceutically acceptable carrier.

70. A pharmaceutical composition according to claim 69, wherein each PEG has a molecular weight of about 20,000 Daltons.

71. A compound that binds to and activates the erythropoietin receptor (EPO-R), which compound comprises a peptide dimer having the formula:

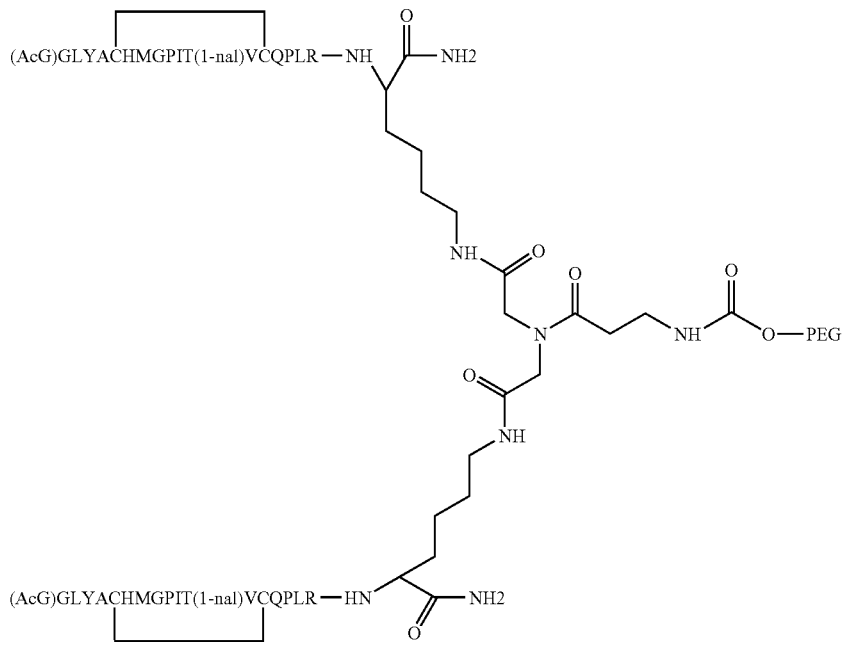

wherein
(i) in each peptide monomer of the peptide dimer, each amino acid is indicated by standard one letter abbreviation, AcG is N-acetylglycine, and 1-nal is 1-naphthylalanine;
(ii) each peptide monomer of the peptide dimer contains an intramolecular disulfide bond between the two cysteine (C) residues of each monomer (iii) PEG comprises a linear unbranched polyethylene glycol (PEG) moiety having a molecular weight of about 20,000 to about 40,000 Daltons.

72. A compound that binds to and activates the erythropoietin receptor (EPO-R), which compound comprises a peptide dimer having the formula:

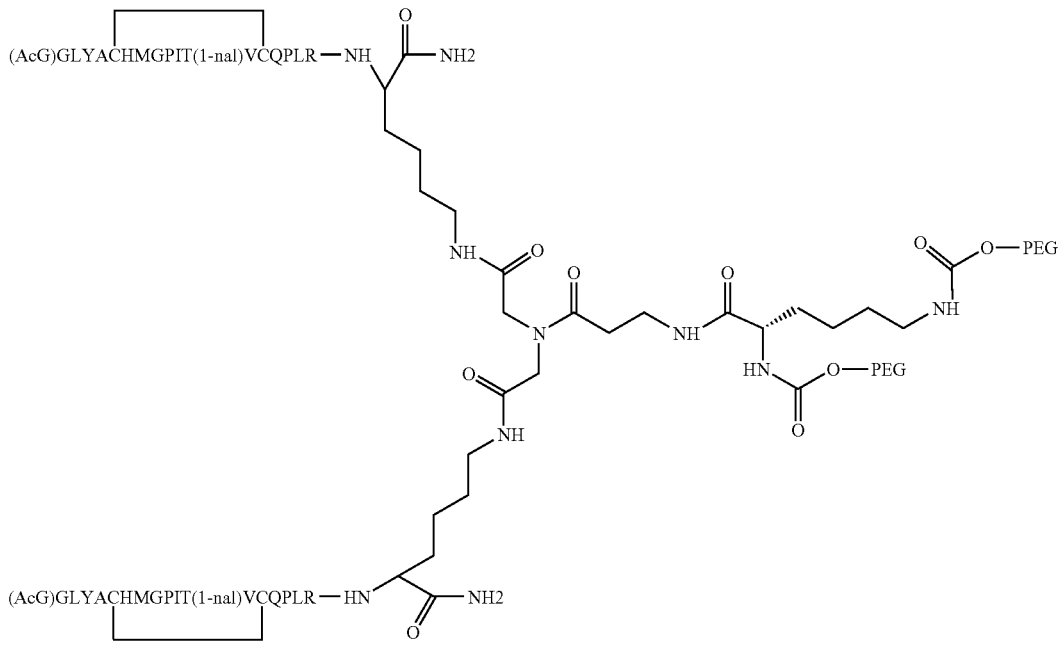

wherein
  (i) in each peptide monomer of the peptide dimer, each amino acid is indicated by standard one letter abbreviation, AcG is N-acetylglycine, and 1-nal is 1-naphthylalanine;
  (ii) each peptide monomer of the peptide dimer contains an intramolecular disulfide bond between the two cysteine (C) residues of each monomer
  (iii) PEG comprises two linear polyethylene glycol (PEG) moities having a combined molecular weight of about 10,000 to about 60,000 Daltons.

* * * * *

UNITED STATES PATENT AND TRADEMARK OFFICE
CERTIFICATE OF CORRECTION

| | | |
|---|---|---|
| PATENT NO. | : 7,084,245 B2 | Page 1 of 1 |
| APPLICATION NO. | : 10/844968 | |
| DATED | : August 1, 2006 | |
| INVENTOR(S) | : Christopher P. Holmes et al. | |

It is certified that error appears in the above-identified patent and that said Letters Patent is hereby corrected as shown below:

Col. 166, line 59, Thur 168, line 48, delete claims 50 - 56.

Signed and Sealed this

Tenth Day of April, 2007

JON W. DUDAS
*Director of the United States Patent and Trademark Office*

```
                        SEQUENCE LISTING

<160> NUMBER OF SEQ ID NOS: 13

<210> SEQ ID NO 1
<211> LENGTH: 20
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-acetylglycine
<220> FEATURE:
<221> NAME/KEY: MISC_FEATURE
<222> LOCATION: (13)..(13)
<223> OTHER INFORMATION: Xaa is 1-naphthylalanine

<400> SEQUENCE: 1

Xaa Gly Leu Tyr Ala Cys His Met Gly Pro Ile Thr Xaa Val Cys Gln
1               5                   10                  15

Pro Leu Arg Lys
            20

<210> SEQ ID NO 2
<211> LENGTH: 21
<212> TYPE: PRT
<213> ORGANISM: artificial
<220> FEATURE:
<223> OTHER INFORMATION: synthetic protein
<220> FEATURE:
<221> NAME/KEY: MISC_FEATURE
<222> LOCATION: (1)..(1)
<223> OTHER INFORMATION: Xaa is N-acetylglycine
<220> FEATURE:
<221> NAME/KEY: MISC_FEATURE
<222> LOCATION: (13)..(13)
<223> OTHER INFORMATION: Xaa is 1-naphthylalanine
<220> FEATURE:
<221> NAME/KEY: MISC_FEATURE
<222> LOCATION: (20)..(20)
<223> OTHER INFORMATION: Xaa is N-methylglycine

<400> SEQUENCE: 2

Xaa Gly Leu Tyr Ala Cys His Met Gly Pro Ile Thr Xaa Val Cys Gln
1               5                   10                  15
```

Pro Leu Arg Xaa Lys
            20

<210> SEQ ID NO 3
<211> LENGTH: 20
<212> TYPE: PRT
<213> ORGANISM: artificial
<220> FEATURE:
<223> OTHER INFORMATION: synthetic protein
<220> FEATURE:
<221> NAME/KEY: MISC_FEATURE
<222> LOCATION: (1)..(1)
<223> OTHER INFORMATION: Xaa is N-acetylglycine
<220> FEATURE:
<221> NAME/KEY: MISC_FEATURE
<222> LOCATION: (13)..(13)
<223> OTHER INFORMATION: Xaa is 1-naphthylalanine
<220> FEATURE:
<221> NAME/KEY: MISC_FEATURE
<222> LOCATION: (20)..(20)
<223> OTHER INFORMATION: Xaa is N-methylglycine

<400> SEQUENCE: 3

Xaa Gly Leu Tyr Ala Cys His Met Gly Pro Ile Thr Xaa Val Cys Gln
1               5                   10                  15

Pro Leu Arg Xaa
            20

<210> SEQ ID NO 4
<211> LENGTH: 20
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: biotinylated

<400> SEQUENCE: 4

Gly Gly Leu Tyr Ala Cys His Met Gly Pro Ile Thr Trp Val Cys Gln
1               5                   10                  15

Pro Leu Arg Gly
            20

<210> SEQ ID NO 5
<211> LENGTH: 5
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-acetylglycine
<220> FEATURE:
<221> NAME/KEY: MISC_FEATURE
<222> LOCATION: (4)..(4)
<223> OTHER INFORMATION: Y side chain tBu protected

<400> SEQUENCE: 5

Xaa Gly Leu Tyr Ala
1               5

<210> SEQ ID NO 6
<211> LENGTH: 4
<212> TYPE: PRT
<213> ORGANISM: artificial
<220> FEATURE:

```
<223> OTHER INFORMATION: synthetic peptide
<220> FEATURE:
<221> NAME/KEY: MISC_FEATURE
<222> LOCATION: (1)..(1)
<223> OTHER INFORMATION: NH2 protected by Fmoc
<220> FEATURE:
<221> NAME/KEY: MISC_FEATURE
<222> LOCATION: (1)..(1)
<223> OTHER INFORMATION: side chain Acm protected
<220> FEATURE:
<221> NAME/KEY: MISC_FEATURE
<222> LOCATION: (2)..(2)
<223> OTHER INFORMATION: side chain Trt protected

<400> SEQUENCE: 6

Cys His Met Gly
1

<210> SEQ ID NO 7
<211> LENGTH: 8
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: NH2 protected by Fmoc
<220> FEATURE:
<221> NAME/KEY: MISC_FEATURE
<222> LOCATION: (3)..(3)
<223> OTHER INFORMATION: side chain tBu protected
<220> FEATURE:
<221> NAME/KEY: MISC_FEATURE
<222> LOCATION: (4)..(4)
<223> OTHER INFORMATION: Xaa is 1-naphthylalanine
<220> FEATURE:
<221> NAME/KEY: MISC_FEATURE
<222> LOCATION: (6)..(6)
<223> OTHER INFORMATION: side chain Acm protected
<220> FEATURE:
<221> NAME/KEY: MISC_FEATURE
<222> LOCATION: (7)..(7)
<223> OTHER INFORMATION: side chain Trt protected

<400> SEQUENCE: 7

Pro Ile Thr Xaa Val Cys Gln Pro
1               5

<210> SEQ ID NO 8
<211> LENGTH: 3
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: side chain Pbf protected
<220> FEATURE:
<221> NAME/KEY: MISC_FEATURE
<222> LOCATION: (3)..(3)
<223> OTHER INFORMATION: Xaa is N-methylglycine
<220> FEATURE:
<221> NAME/KEY: MISC_FEATURE
<222> LOCATION: (3)..(3)
<223> OTHER INFORMATION: COOH Bn protected

<400> SEQUENCE: 8

Leu Arg Xaa
1

<210> SEQ ID NO 9
```

```
<211> LENGTH: 9
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-acetylglycine
<220> FEATURE:
<221> NAME/KEY: MISC_FEATURE
<222> LOCATION: (4)..(4)
<223> OTHER INFORMATION: side chain tBu protected
<220> FEATURE:
<221> NAME/KEY: MISC_FEATURE
<222> LOCATION: (6)..(6)
<223> OTHER INFORMATION: side chain Acm protected
<220> FEATURE:
<221> NAME/KEY: MISC_FEATURE
<222> LOCATION: (7)..(7)
<223> OTHER INFORMATION: side chain Trt protected

<400> SEQUENCE: 9

Xaa Gly Leu Tyr Ala Cys His Met Gly
1               5

<210> SEQ ID NO 10
<211> LENGTH: 11
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: NH2 protected by Fmoc
<220> FEATURE:
<221> NAME/KEY: MISC_FEATURE
<222> LOCATION: (3)..(3)
<223> OTHER INFORMATION: side chain tBu protected
<220> FEATURE:
<221> NAME/KEY: MISC_FEATURE
<222> LOCATION: (4)..(4)
<223> OTHER INFORMATION: Xaa is 1-naphthylalanine
<220> FEATURE:
<221> NAME/KEY: MISC_FEATURE
<222> LOCATION: (6)..(6)
<223> OTHER INFORMATION: side chain Acm protected
<220> FEATURE:
<221> NAME/KEY: MISC_FEATURE
<222> LOCATION: (7)..(7)
<223> OTHER INFORMATION: side chain Trt protected
<220> FEATURE:
<221> NAME/KEY: MISC_FEATURE
<222> LOCATION: (10)..(10)
<223> OTHER INFORMATION: side chain Pbf protected
<220> FEATURE:
<221> NAME/KEY: MISC_FEATURE
<222> LOCATION: (11)..(11)
<223> OTHER INFORMATION: Xaa is N-methylglycine
<220> FEATURE:
<221> NAME/KEY: MISC_FEATURE
<222> LOCATION: (11)..(11)
<223> OTHER INFORMATION: COOH Bn protected

<400> SEQUENCE: 10

Pro Ile Thr Xaa Val Cys Gln Pro Leu Arg Xaa
1               5                   10

<210> SEQ ID NO 11
<211> LENGTH: 20
<212> TYPE: PRT
<213> ORGANISM: artificial
<220> FEATURE:
<223> OTHER INFORMATION: synthetic peptide
```

```
<220> FEATURE:
<221> NAME/KEY: MISC_FEATURE
<222> LOCATION: (1)..(1)
<223> OTHER INFORMATION: Xaa is N-acetylglycine
<220> FEATURE:
<221> NAME/KEY: MISC_FEATURE
<222> LOCATION: (4)..(4)
<223> OTHER INFORMATION: side chain tBu protected
<220> FEATURE:
<221> NAME/KEY: MISC_FEATURE
<222> LOCATION: (6)..(6)
<223> OTHER INFORMATION: side chain Acm protected
<220> FEATURE:
<221> NAME/KEY: MISC_FEATURE
<222> LOCATION: (7)..(7)
<223> OTHER INFORMATION: side chain Trt protected
<220> FEATURE:
<221> NAME/KEY: MISC_FEATURE
<222> LOCATION: (12)..(12)
<223> OTHER INFORMATION: side chain tBu protected
<220> FEATURE:
<221> NAME/KEY: MISC_FEATURE
<222> LOCATION: (13)..(13)
<223> OTHER INFORMATION: Xaa is 1-naphthylalanine
<220> FEATURE:
<221> NAME/KEY: MISC_FEATURE
<222> LOCATION: (15)..(15)
<223> OTHER INFORMATION: side chain Acm protected
<220> FEATURE:
<221> NAME/KEY: MISC_FEATURE
<222> LOCATION: (16)..(16)
<223> OTHER INFORMATION: side chain Trt protected
<220> FEATURE:
<221> NAME/KEY: MISC_FEATURE
<222> LOCATION: (19)..(19)
<223> OTHER INFORMATION: side chain Pbf protected
<220> FEATURE:
<221> NAME/KEY: MISC_FEATURE
<222> LOCATION: (20)..(20)
<223> OTHER INFORMATION: Xaa is N-methylglycine
<220> FEATURE:
<221> NAME/KEY: MISC_FEATURE
<222> LOCATION: (20)..(20)
<223> OTHER INFORMATION: COOH Bn protected

<400> SEQUENCE: 11

Xaa Gly Leu Tyr Ala Cys His Met Gly Pro Ile Thr Xaa Val Cys Gln
1               5                   10                  15

Pro Leu Arg Xaa
            20

<210> SEQ ID NO 12
<211> LENGTH: 20
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-acetylglycine
<220> FEATURE:
<221> NAME/KEY: MISC_FEATURE
<222> LOCATION: (4)..(4)
<223> OTHER INFORMATION: side chain tBu protected
<220> FEATURE:
<221> NAME/KEY: MISC_FEATURE
<222> LOCATION: (6)..(6)
<223> OTHER INFORMATION: side chain Acm protected
<220> FEATURE:
<221> NAME/KEY: MISC_FEATURE
<222> LOCATION: (7)..(7)
<223> OTHER INFORMATION: side chain Trt protected
<220> FEATURE:
<221> NAME/KEY: MISC_FEATURE
<222> LOCATION: (12)..(12)
```

```
<223> OTHER INFORMATION: side chain tBu protected
<220> FEATURE:
<221> NAME/KEY: MISC_FEATURE
<222> LOCATION: (13)..(13)
<223> OTHER INFORMATION: Xaa is 1-naphthylalanine
<220> FEATURE:
<221> NAME/KEY: MISC_FEATURE
<222> LOCATION: (15)..(15)
<223> OTHER INFORMATION: side chain Acm protected
<220> FEATURE:
<221> NAME/KEY: MISC_FEATURE
<222> LOCATION: (16)..(16)
<223> OTHER INFORMATION: side chain Trt protected
<220> FEATURE:
<221> NAME/KEY: MISC_FEATURE
<222> LOCATION: (19)..(19)
<223> OTHER INFORMATION: side chain Pbf protected
<220> FEATURE:
<221> NAME/KEY: MISC_FEATURE
<222> LOCATION: (20)..(20)
<223> OTHER INFORMATION: Xaa is N-methylglycine

<400> SEQUENCE: 12

Xaa Gly Leu Tyr Ala Cys His Met Gly Pro Ile Thr Xaa Val Cys Gln
1               5                   10                  15

Pro Leu Arg Xaa
            20

<210> SEQ ID NO 13
<211> LENGTH: 20
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa is N-acetylglycine
<220> FEATURE:
<221> NAME/KEY: MISC_FEATURE
<222> LOCATION: (4)..(4)
<223> OTHER INFORMATION: side chain tBu protected
<220> FEATURE:
<221> NAME/KEY: MISC_FEATURE
<222> LOCATION: (7)..(7)
<223> OTHER INFORMATION: side chain Trt protected
<220> FEATURE:
<221> NAME/KEY: MISC_FEATURE
<222> LOCATION: (12)..(12)
<223> OTHER INFORMATION: side chain tBu protected
<220> FEATURE:
<221> NAME/KEY: MISC_FEATURE
<222> LOCATION: (13)..(13)
<223> OTHER INFORMATION: Xaa is 1-naphthylalanine
<220> FEATURE:
<221> NAME/KEY: MISC_FEATURE
<222> LOCATION: (16)..(16)
<223> OTHER INFORMATION: side chain Trt protected
<220> FEATURE:
<221> NAME/KEY: MISC_FEATURE
<222> LOCATION: (19)..(19)
<223> OTHER INFORMATION: side chain Pbf protected
<220> FEATURE:
<221> NAME/KEY: MISC_FEATURE
<222> LOCATION: (20)..(20)
<223> OTHER INFORMATION: Xaa is N-methylglycine

<400> SEQUENCE: 13

Xaa Gly Leu Tyr Ala Cys His Met Gly Pro Ile Thr Xaa Val Cys Gln
1               5                   10                  15

Pro Leu Arg Xaa
            20
```